(12) United States Patent
Shoseyov et al.

(10) Patent No.: US 12,115,276 B2
(45) Date of Patent: Oct. 15, 2024

(54) ADDITIVE MANUFACTURING USING RECOMBINANT COLLAGEN-CONTAINING FORMULATION

(71) Applicant: CollPlant Ltd., Rehovot (IL)

(72) Inventors: Oded Shoseyov, Shoham (IL); Nadav Orr, Mazkeret Batya (IL); Jasmine Seror Maknouz, Tel-Aviv (IL); Revital Zarka, Mazkeret Batya (IL)

(73) Assignee: CollPlant Ltd., Rehovot (IL)

( * ) Notice: Subject to any disclaimer, the term of this patent is extended or adjusted under 35 U.S.C. 154(b) by 603 days.

(21) Appl. No.: 16/620,556

(22) PCT Filed: Jun. 8, 2018

(86) PCT No.: PCT/IL2018/050627
§ 371 (c)(1),
(2) Date: Dec. 9, 2019

(87) PCT Pub. No.: WO2018/225076
PCT Pub. Date: Dec. 13, 2018

(65) Prior Publication Data
US 2020/0179562 A1     Jun. 11, 2020

Related U.S. Application Data

(60) Provisional application No. 62/517,179, filed on Jun. 9, 2017.

(51) Int. Cl.
*B33Y 70/00* (2020.01)
*A61L 27/24* (2006.01)
(Continued)

(52) U.S. Cl.
CPC ............ *A61L 27/24* (2013.01); *B29C 64/106* (2017.08); *B33Y 70/00* (2014.12); *B33Y 10/00* (2014.12)

(58) Field of Classification Search
CPC .... B29C 64/106–118; B33Y 70/00–10; B33Y 10/00
See application file for complete search history.

(56) References Cited

U.S. PATENT DOCUMENTS

| 10,597,289 B1 | 3/2020 | Woolley et al. |
| 2013/0304233 A1 | 11/2013 | Dean et al. |

(Continued)

FOREIGN PATENT DOCUMENTS

| CN | 114958079 | 8/2022 |
| JP | 2020-522357 | 7/2020 |

(Continued)

OTHER PUBLICATIONS

Kathryn E. Drzewiecki, Avanish S. Parmar, Ian D. Gaudet, Jonathan R. Branch, Douglas H. Pike, Vikas Nanda, and David I. Shreiber, Methacrylation Induces Rapid, Temperature-Dependent, Reversible Self-Assembly of Type-I Collagen, Langmuir 2014 30 (37), 11204-11211, DOI: 10.1021/la502418s (Year: 2014).*

(Continued)

*Primary Examiner* — Philip C Tucker
*Assistant Examiner* — Andrew L Swanson

(57) ABSTRACT

Compositions containing curable recombinant human collagen, and kits comprising same, which are usable in preparing modeling material formulations for additive manufacturing (e.g., 3D bioprinting) of 3D objects are provided. Methods utilizing such modeling material formulations in additive manufacturing of 3D objects having a collagen-based material in at least a portion thereof, are also provided. The formulations feature a desired viscosity at a temperature higher than 10° C. (e.g., room temperature or 37° C.) and allow performing the additive manufacturing without cooling the system or a part thereof.

20 Claims, 10 Drawing Sheets

Figure 1:
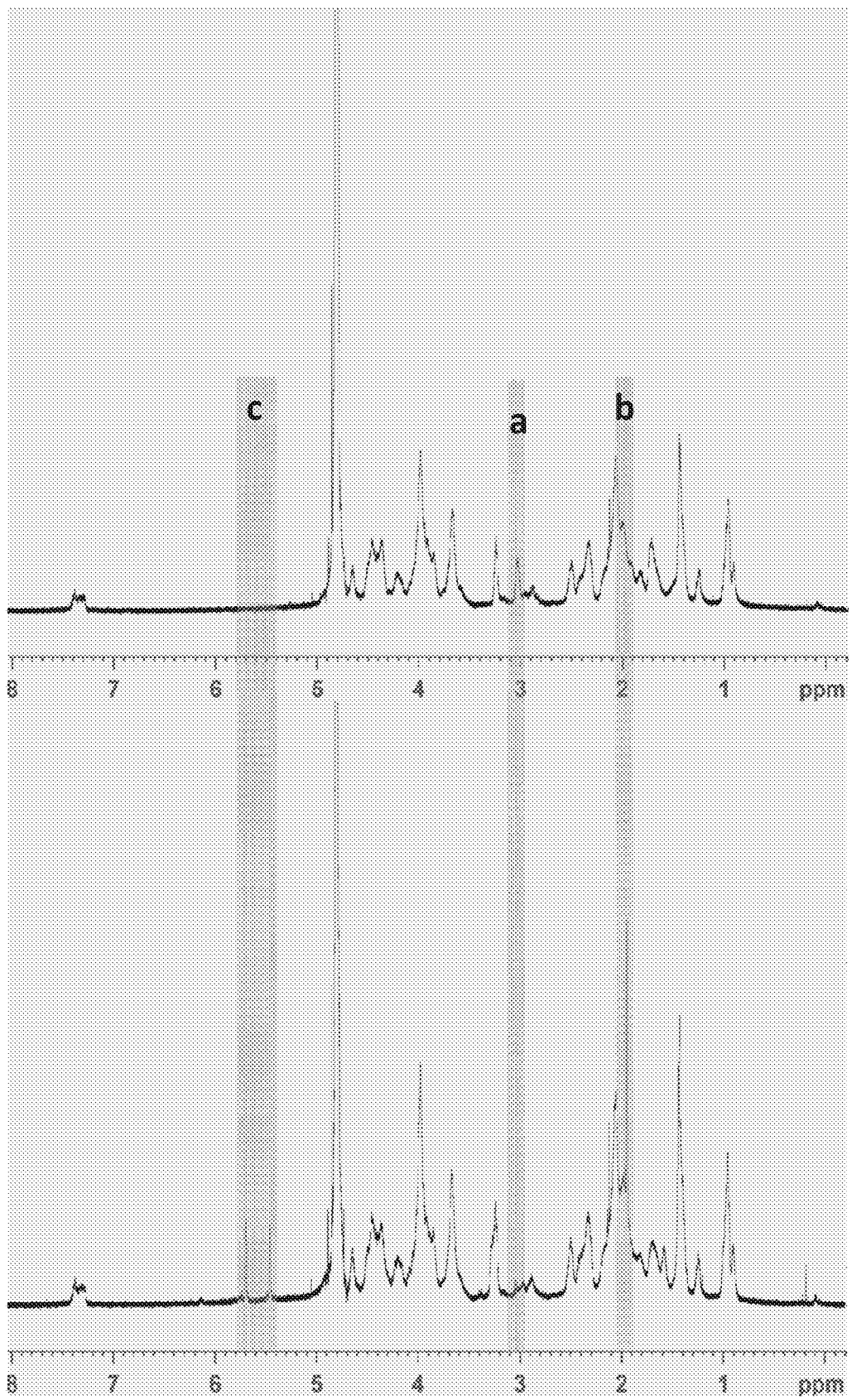

Specification includes a Sequence Listing.

(51) Int. Cl.
*B29C 64/106* (2017.01)
*B33Y 10/00* (2015.01)

(56) References Cited

U.S. PATENT DOCUMENTS

| | | | | |
|---|---|---|---|---|
| 2016/0046832 | A1* | 2/2016 | Wroblesky | B33Y 70/00 425/375 |
| 2016/0120955 | A1* | 5/2016 | Gueta | A61K 35/19 424/530 |
| 2016/0193384 | A1* | 7/2016 | Phopase | C08F 290/06 514/772.4 |
| 2017/0143831 | A1 | 5/2017 | Varanasi et al. | |
| 2018/0193524 | A1 | 7/2018 | Shoseyov et al. | |
| 2018/0303616 | A1* | 10/2018 | Bhattacharyya | A61L 27/56 |
| 2020/0061239 | A1 | 2/2020 | Petrak et al. | |
| 2020/0179563 | A1* | 6/2020 | Bagley | B29C 64/40 |
| 2020/0339925 | A1 | 10/2020 | Miller et al. | |
| 2021/0229364 | A1 | 7/2021 | McLeod et al. | |

FOREIGN PATENT DOCUMENTS

| | | | |
|---|---|---|---|
| WO | WO 2006/035442 | | 4/2006 |
| WO | WO 2009/053985 | | 4/2009 |
| WO | WO 2011/064773 | | 6/2011 |
| WO | WO 2013/093921 | | 6/2013 |
| WO | WO 2014/14762 | | 1/2014 |
| WO | WO 2014/147622 | | 9/2014 |
| WO | WO-2014147622 | A1 * 9/2014 | A61K 33/14 |
| WO | WO 2015/032985 | | 3/2015 |
| WO | WO 2015/055656 | | 4/2015 |
| WO | WO 2016/154070 | | 9/2016 |
| WO | WO 2018/225076 | | 12/2018 |
| WO | WO 2018/225076 | A8 | 12/2018 |
| WO | WO 2020/028720 | | 2/2020 |
| WO | WO 2022/093236 | | 5/2022 |
| WO | WO 2023/073711 | | 5/2023 |

OTHER PUBLICATIONS

Wlodarczyk-Biegun, 3D bioprinting of structural proteins, Biomaterials, vol. 134, Apr. 12, 2017, pp. 180-201, ISSN 0142-9612, https://doi.org/10.1016/j.biomaterials.2017.04.019. (https://www.sciencedirect.com/science/article/pii/S0142961217302478) (Year: 2017).*

Stein H, et al. Production of bioactive, post-translationally modified, heterotrimeric, human recombinant type-I collagen in transgenic tobacco. Biomacromolecules. Sep. 14, 2009;10(9): https://pubs.acs.org/doi/10.1021/bm900571b (Year: 2009).*

Yoon, Development of cell-laden 3D scaffolds for efficient engineered skin substitutes by collagen gelation, Jan. 21, 2016, RSC Advances, Issue 26, p. 21439-21447 (Year: 2016).*

Shoseyov O, Posen Y, Grynspan F. Human recombinant type I collagen produced in plants. Tissue Eng Part A. Jul. 2013; 19(13-14): 1527-33. doi: 10.1089/ten.TEA.2012.0347. Epub Feb. 19, 2013. PMID: 23252967. (Year: 2013).*

Supplementary European Search Report and the European Search Opinion Dated Mar. 16, 2021 From the European Patent Office Re. Application No. 18813255.9. (8 Pages).

Willard et al. "Plant-Derived Human Collagen Scaffolds for Skin Tissue Engineering", Tissue Engineering Part A, XP055782194, 19(13-14): 1507-1518, Published Online Feb. 19, 2013.

Wlodarczyk-Biegun et al. "3D Bioprinting of Structural Proteins", Biomaterials, XP085004461, 134: 180-201, Available Online Apr. 12, 2017.

International Preliminary Report on Patentability Dated Dec. 19, 2019 From the International Bureau of WIPO Re. Application No. PCT/IL2018/050627. (7 Pages).

International Search Report and the Written Opinion Dated Aug. 29, 2018 From the International Searching Authority Re. Application No. PCT/IL2018/050627. (12 Pages).

Drzewiecki et al. "A Thermoreversible, Photocrosslinkable Collagen Bio-Ink for Free-Form Fabrication of Scaffolds for Regenerative Medicine", Technology, 5(3): 1-11, Sep. 2017.

Drzewiecki et al. "Methacrylation Induces Rapid, Temperature-Dependent, Reversible Self-Assembly of Type I Collagen", Langmuir, 30(37): 11204-11211, Aug. 28, 2014. P.11205, 1-h col. Third Para.

Gaudet et al. "Characterization of Methacrylated Type-I Collagen as A Dynamic, Photoactive Hydrogel", Biointerphases, 7(1-4): 25-1-25-9, Published Online Mar. 10, 2012. Abstract, Chap.2.1, Fig.4.

Isaacson et al. "3D Bioprinting of A Corneal Stroma Equivalent", Experimental Eye Research, 173: 188-193, Published Online May 30, 2018.

Miller et al. "Editorial: Special Issue on 3D Printing of Biomaterials", ACS Biomaterials Science & Engineering, 2(10): 1658-1661, Oct. 10, 2016.

Murphy et al. "3D Bioprinting of Tissues and Organs", Nature Biotechnology, 32(8): 773-785, Published Online Aug. 5, 2014.

Ravichandran et al. "Functionalised Type-I Collagen as A Hydrogel Building Block for Bio-Orthogonal Tissue Engineering Applications", Journal of Materials Chemistry B, 4(2): 318-326, Nov. 23, 2015. Suppl. Material Para 2.11, p. 8, fig.8, Suppl. Information, Para 2.5.

Stein et al. "Production of Bioactive, Post-Translationally Modified, Heterotrimeric, Human Recombinant Type-I Collagen in Transgenic Tobacco", Biomacromolecules, 10(9): 2640-2645, Published Online Aug. 14, 2009.

Zhang et al. "Nerve Transfer With 3D-Printed Branch Nerve Conduits", Burns & Trauma, 10: tkac010-1-tkac010-12, Published Online Apr. 15, 2022.

Notice of Reasons for Rejection Dated Aug. 9, 2022 From the Japan Patent Office Re. Application No. 2019-567638 and Its Translation Into English. (10 Pages).

International Search Report and the Written Opinion Dated Jan. 12, 2023 in the International Searching Authority Re. Application No. PCT/IL2022/051143. (10 Pages).

Browning et al. "Bioactive Hydrogels With Enhanced Initial and Sustained Cell Interactions", Biomacromolecules, 14(7): 2225-2233, Published Online Jun. 24, 2013.

Fairbanks et al. "Photoinitiated Polymerization of PEG-Diacrylate with Lithium Phenyl-2,4,6-Trimethylbenzoylphosphinate: Polymerization Rate and Cytocompatibility", Biomaterials, 30(35): 6702-6707, Dec. 2009.

Majima et al. "Phenyl-2,4,6-Trimethylbenzoylphosphinates as Water-Soluble Photoinitiators. Generation and Reactivity of O=b(C6Hs)(O-) Radical Anions", Die Makromolekulare Chemie, 192(10): 2307-2315, Oct. 1991.

Decision of Rejection Dated Feb. 21, 2023 From the Japan Patent Office Re. Application No. 2019-567638 and Its Translation Into English. (14 Pages).

Examination Report Dated May 12, 2023 From the Australian Government, IP Australia Re. Application No. 2018282131. (5 Pages).

Drzewiecki et al. "Methacrylation Induces Rapid, Temperature-Dependent, Reversible Self-Assembly of Type—I Collagen", American Chemical Society Publications, Langmuir 30: 11204-11211, Aug. 28, 2014.

Matthyssen et al. "Cellularization of 3D Printed Recombinant Human Collagen Type III Scaffolds Using Corneal Mesenchymal Stem Cells", ARVO Annual Meeting Abstract, 57(12): Abstract, Sep. 2016.

Requisition by the Examiner Dated Oct. 17, 2023 From the Innovation, Science and Economic Development Canada, Canadian Intellectual Property Office Re. Application No. 3,065,481. (4 Pages).

International Search Report and the Written Opinion Dated Jan. 16, 2024 From the International Searching Authority Re. Application No. PCT/IL2023/051112 (13 Pages).

Examination Report Dated Mar. 21, 2024 From the Australian Government, IP Australia Re. Application No. 2018282131. (2 Pages).

International Preliminary Report on Patentability Dated May 10, 2024 From the International Bureau of WIPO Re. Application No. PCT/IL2022/051143 (6 Pages).

(56) References Cited

OTHER PUBLICATIONS

Communication Pursuant to Article 94(3) EPC Dated Jul. 2, 2024 From the European Patent Office Re. Application No. 18813255.9. (6 Pages).
Notice of Reason(s) for Rejection Dated Aug. 6, 2024 From the Japan Patent Office Re. Application No. 2023-101072 and Its Translation Into English. (10 Pages).

* cited by examiner

ADDITIVE MANUFACTURING USING RECOMBINANT COLLAGEN-CONTAINING FORMULATION

RELATED APPLICATION

This application is a National Phase of PCT Patent Application No. PCT/IL2018/050627 having International filing date of Jun. 8, 2018, which claims the benefit of priority under 35 USC § 119(e) of U.S. Provisional Patent Application No. 62/517,179 filed on Jul. 9, 2017. The contents of which the above applications are all incorporated by reference as if fully set forth herein in their entirety.

SEQUENCE LISTING STATEMENT

The ASCII file, entitled 80341SequenceListing.txt, created on Dec. 9, 2019, comprising 129,346 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to additive manufacturing and, more particularly, but not exclusively, to three-dimensional (3D) bioprinting of 3D objects using a collagen-based building material.

Collagen comprises the main component of connective tissue and is the most abundant protein in mammals, comprising approximately 30% of the proteins found in the body. Collagen serves as the predominant component and primary structural-mechanical determinant of most tissue extracellular matrix (ECM) [see, for example, Kadler K. Birth Defects Res C Embryo Today. 2004; 72:1-11; Kadler K E, Baldock C, Bella J, Boot-Handford R P. J Cell Sci. 2007; 120:1955-1958.; Kreger S T. Biopolymers. 2010 93(8): 690-707].

Due to its unique characteristics and diverse profile in human body functions, collagen is frequently selected from a variety of biocompatible materials for use in tissue repair to support structural integrity, induce cellular infiltration and promote tissue regeneration. Among the 5 major collagen types, Type I collagen is the most abundant form of in the human body. Collagen's unique properties make it a favorite choice for regenerative medicine products.

Additive manufacturing (AM) is generally a process in which a three-dimensional (3D) object is manufactured utilizing a computer model of the objects. The basic operation of any AM system consists of slicing a three-dimensional computer model into thin cross sections, translating the result into two-dimensional position data and feeding the data to control equipment which manufacture a three-dimensional structure in a layerwise manner.

Various AM technologies exist, amongst which are stereolithography, digital light processing (DLP), and three-dimensional (3D) printing such as 3D inkjet printing. Such techniques are generally performed by layer by layer deposition and hardening (e.g., solidification) of one or more building materials, which typically include photopolymerizable (photocurable) materials.

Stereolithography, for example, is an additive manufacturing process which employs a liquid ultraviolet (UV)-curable building material and a UV laser. In such a process, for each dispensed layer of the building material, the laser beam traces a cross-section of the part pattern on the surface of the dispensed liquid building material. Exposure to the UV laser light cures and solidifies the pattern traced on the building material and joins it to the layer below. After being built, the formed parts are immersed in a chemical bath in order to be cleaned of excess building material and are subsequently cured in an UV oven.

In three-dimensional printing processes, for example, a building material is dispensed from a dispensing head having a set of nozzles to deposit layers on a supporting structure. Depending on the building material, the layers may then be cured or solidify using a suitable device.

The building materials may include modeling material formulation(s) and support material formulation(s), which form, upon hardening, the object and the temporary support constructions supporting the object as it is being built, respectively.

The modeling material formulation(s) is/are deposited to produce the desired object and the support material formulation(s) is/are used, with or without modeling material elements, to provide support structures for specific areas of the object during building and assure adequate vertical placement of subsequent object layers, e.g., in cases where objects include overhanging features or shapes such as curved geometries, negative angles, voids, and so on.

Both the modeling and support materials are preferably liquid at the working temperature at which they are dispensed, and subsequently hardened, typically upon exposure to hardening or curing condition such as curing energy (e.g., UV curing), to form the required layer shape. After printing completion, support structures, if present, are removed to reveal the final shape of the fabricated 3D object. The hardening (curing) of the dispensed materials typically involves polymerization (e.g., photopolymerization) and/or crosslinking (e.g., photocrosslinking).

Additive manufacturing has been first used in biological applications for forming three-dimensional sacrificial resin molds in which 3D scaffolds from biological materials were created.

3D bioprinting is an additive manufacturing methodology which uses biological materials, optionally in combination with chemicals and/or cells, that are printed layer-by-layer with a precise positioning and a tight control of functional components placement to create a 3D structure.

Three dimensional (3D) bioprinting is gaining momentum in many medicinal applications, especially in regenerative medicine, to address the need for complex scaffolds, tissues and organs suitable for transplantation.

Inherent to 3D printing in general is that the mechanical properties of the printing media (the dispensed building material) are very different from the post-printed cured (hardened) material.

To allow tight control on the curing (e.g., polymerization) after printing, the building material commonly includes polymerizable (e.g., photopolymerizable) moieties or groups that polymerize (e.g., by chain elongation and/or cross-linking) upon being dispensed, to preserve the geometric shape and provide the necessary physical properties of the final product.

Different technologies have been developed for 3D bioprinting, including 3D Inkjet printing, Extrusion printing, Laser-assisted printing and Projection stereolithography [see, for example, Murphy S V, Atala A, Nature Biotechnology. 2014 32(8).; Miller J S, Burdick J. ACS Biomater. Sci. Eng. 2016, 2, 1658-1661]. Each technology has its different requirements for the dispensed building material (also referred to herein as printing media), which is derived from the specific application mechanism and the curing/gelation process required to maintain the 3D structure of the scaffold post printing.

For all technologies, the most important parameter determining the accuracy and efficiency of the printing is the static and dynamic physical properties of the dispensed building material, including viscosity, shear thinning and thixotropic properties. The static and dynamic properties of the building material are important not only for the printing technology but also when considering cell-laden printing, i.e. including cells in the building material dispensed during printing. In this case, the shearing forces applied to the building material during printing (dispensing) have a significant effect on the survival of the cells. Therefore, it is desirable to have good control on the specific properties of the printing media over a wide range of conditions, i.e. concentration, temperature, ionic strength and pH.

Type I collagen is considered a perfect candidate for use as a major component of a building material in 3D-bioprinting.

Collagen methacrylate can be used as a rapidly self-assembling type I collagen to form cross-linked hydrogels for tissue engineering [see, for example, Isaacson et al., Experimental Eye Research 173, 188-193 (2018)]. It has been used with mesenchymal stem cells [Kathryn E. Drzewiecki et al., A thermoreversible, photocrosslinkable collagen bio-ink for free-form fabrication of scaffolds for regenerative medicine, TECHNOLOGY (2017)], fibroblasts, adipose derived stem cells, epithelial cells, and many more. Collagen methacrylate is useful for forming scaffolds with varying degree of stiffness, by altering collagen concentration or the curing conditions (e.g., intensity and duration of irradiation).

Collagen methacrylate extracted from tissues has been extensively characterized for its usefulness in 3D-bioprinting (extrusion, inkjet, and photolithographic [Drzewiecki, K. E. et al. Langmuir 30, 11204-11211 (2014); Gaudet, I. D. & Shreiber, D. I. Biointerphases 7, 25 (2012)].

Despite the significant advantages offered by this natural polymer, a number of factors hinder its use for 3D bioprinting. The use of tissue extracted collagen for this purpose is limited due to its sensitivity to temperature and ionic strength, which leads to spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity during printing. Keeping the printing media at low temperature until application is a possible solution for this phenomena but implies a serious technical limitation. Another solution is the use of gelatin, the denatured form of collagen which does not become gel-like under these conditions. However, gelatin lacks the genuine tissue and cell interactions of native collagen and thus crucial biological functions are lost.

The present assignee has developed a technology that allows the purification of naïve human Type I collagen (rhCollagen) by introducing into tobacco plants, five human genes encoding heterotrimeric type I collagen [see, for example, Stein H. (2009) Biomacromolecules; 10:2640-5]. The protein is purified to homogeneity through a cost-effective industrial process taking advantage of collagen's unique properties. See also WO 2006/035442, WO 2009/053985, WO 2011/064773, WO 2013/093921, WO 2014/147622, and patents and patent applications deriving therefrom, all of which are incorporated by reference as if fully set forth herein. Additional background art includes U.S. patent application Ser. No. 15/867,783.

SUMMARY OF THE INVENTION

According to an aspect of some embodiments of the present invention there is provided a formulation for use, or usable, in additive manufacturing of a three-dimensional object that comprises, in at least a portion thereof, a collagen-based material, the formulation comprising a recombinant human collagen featuring at least one curable group.

According to some of any of the embodiments of the present invention, the at least one curable group is a photocurable group.

According to some of any of the embodiments of the present invention, the recombinant human collagen is a recombinant human Type I collagen.

According to some of any of the embodiments of the present invention, the recombinant human collagen is a plant-derived recombinant collagen.

According to some of any of the embodiments of the present invention, the formulation further comprises and an aqueous carrier.

According to some of any of the embodiments of the present invention, the formulation features a pH that ranges from about 6 to about 8.

According to some of any of the embodiments of the present invention, the aqueous carrier comprises a phosphate buffer.

According to some of any of the embodiments of the present invention, the aqueous carrier comprises an acid.

According to some of any of the embodiments of the present invention, the aqueous carrier comprises a culturing medium.

According to some of any of the embodiments of the present invention, a concentration of the recombinant human collagen in the modeling material formulation ranges from 0.5 mg/mL to 50 mg/mL, or from 0.5 mg/mL to 20 mg/mL.

According to some of any of the embodiments of the present invention, the formulation further comprises at least one curable material other than the recombinant human collagen featuring the curable group.

According to some of any of the embodiments of the present invention, a weight ratio of the recombinant human collagen featuring the curable group and the at least one curable material ranges from 10:1 to 1:2, or from 10:1 to 1:1, or from 5:1 to 2:1.

According to some of any of the embodiments of the present invention, the formulation further comprises an agent that modifies a mechanical and/or rheological and/or physical property of the formulation and/or of a respective portion of the object.

According to some of any of the embodiments of the present invention, the formulation further comprises a biological material other than the human recombinant collagen.

According to some of any of the embodiments of the present invention, the formulation is a shear-thinning formulation.

According to some of any of the embodiments of the present invention, the formulation is a thermal-thinning formulation.

According to some of any of the embodiments of the present invention, the formulation features a viscosity of no more than 2,000 centipoises, or no more than 1,500 centipoises, at a zero shear strain rate, at 37° C., wherein a concentration of the recombinant human collagen featuring a curable group is at least 3 mg/mL.

According to some of any of the embodiments of the present invention, the modeling material formulation features a viscosity of no more than 2000 centipoises, or no more than 1,500 centipoises, at a shear strain rate of 5 1/sec, at room temperature, wherein a concentration of the recombinant human collagen featuring a curable group is at least 3 mg/mL.

According to some of any of the embodiments of the present invention, the formulation features, when hardened, storage modulus (G') of at least 1,000 Pa.

According to some of any of the embodiments of the present invention, the formulation features, when hardened, an increase of at least 10-folds of its storage modulus (G').

According to an aspect of some embodiments of the present invention there is provided a process or a method of additive manufacturing of a three-dimensional object featuring, in at least a portion thereof, a collagen-based material, the process comprising dispensing at least one modeling material formulation to sequentially form a plurality of layers in a configured pattern corresponding to a shape of the object, wherein for at least a portion of the layers, the dispensing is of a modeling material formulation that comprises a recombinant human collagen featuring at least one curable group, as described herein in any of the respective embodiments and any combination thereof, thereby manufacturing the three-dimensional object.

According to some of any of the embodiments described herein, the process further comprises exposing the portion of the layers to a curing condition suitable for hardening the recombinant human collagen featuring the at least one curable group.

According to some of any of the embodiments described herein, the at least one curable group is a photocurable group.

According to some of any of the embodiments described herein, the process further comprises exposing the portion of the layers to irradiation.

According to some of any of the embodiments described herein, the recombinant human collagen is a recombinant human Type I collagen.

According to some of any of the embodiments described herein, for at least a portion of the layers, the dispensing is further of a modeling material formulation that comprises at least one curable material other than the recombinant human collagen featuring the curable group.

According to some of any of the embodiments described herein, the dispensing is of a modeling material formulation that comprises the recombinant human collagen featuring the curable group and the at least one curable material.

According to some of any of the embodiments described herein, a weight ratio of the recombinant human collagen featuring the curable group and the at least one curable material ranges from 10:1 to 1:2, or from 10:1 to 1:1, or from 5:1 to 2:1.

According to some of any of the embodiments described herein, the at least one curable material comprises a hyaluronic acid featuring at least one curable group.

According to some of any of the embodiments described herein, the modeling material formulation further comprises an agent that modifies a mechanical and/or rheological and/or physical property of the formulation and/or of a respective portion of the object.

According to some of any of the embodiments described herein, for at least a portion of the layers, the dispensing is further of a modeling material formulation that comprises an agent that modifies a mechanical and/or rheological and/or physical property of the formulation and/or of a respective portion of the object.

According to some of any of the embodiments described herein, the agent is a thixotropic agent.

According to some of any of the embodiments described herein, the agent is a gel-forming agent.

According to some of any of the embodiments described herein, the modeling material formulation further comprises a biological material other than the human recombinant collagen.

According to some of any of the embodiments described herein, for at least a portion of the layers, the dispensing is further of a modeling material formulation that comprises a biological material other than the human recombinant collagen.

According to some of any of the embodiments described herein, the modeling material formulation that comprises the human recombinant collagen further comprises the biological material.

According to some of any of the embodiments of the present invention, the dispensing is at a temperature of at least 10° C., or of at least 20° C., or of 37° C.

According to an aspect of some embodiments of the present invention there is provided a three-dimensional biological object obtainable by the process of AM as described herein in any of the respective embodiments and any combination thereof.

According to some of any of the embodiments of the present invention, the object further comprises a biological material other than the collagen-based material in or on at least a portion thereof.

According to some of any of the embodiments of the present invention, the object is for use, or is usable in, repairing a damaged tissue.

According to some of any of the embodiments of the present invention, the object is an artificial tissue or organ, or is usable, or for use, in constructing an artificial organ or tissue.

According to an aspect of some embodiments of the present invention there is provided a composition comprising a recombinant human collagen featuring at least one curable group, as described herein in any of the respective embodiments and any combination thereof.

According to some of any of the embodiments of the present invention, the composition is for use, or is usable, in preparing a modeling material formulation usable in additive manufacturing of a three-dimensional object that comprises, in at least a portion thereof, a collagen-based material.

According to some of any of the embodiments of the present invention, the composition further comprises an aqueous solution of the recombinant human collagen featuring at least one curable group.

According to an aspect of some embodiments of the present invention there is provided a kit comprising the composition described herein packaged therein, the kit being identified for use in preparing a modeling material formulation usable in additive manufacturing of a three-dimensional object that comprises, in at least a portion thereof, a collagen-based material.

According to some of any of the embodiments of the present invention, the modeling material formulation further comprises an aqueous carrier, and the kit further comprises the aqueous carrier or instructions to prepare the formulation with the aqueous carrier.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents $^1$H nuclear magnetic resonance (NMR) spectra of rhCollagen (top) and of rhCollagen methacrylate (bottom), as recorded in quantitative analysis using 500 MHz spectrometer. The signals of the methyl function and acrylic protons of the methacrylate introduced in rhCollagen methacrylate are indicated as (b) and (c), respectively, and the lysine methylene signals of the rhCollagen as indicated as (a).

Figure 2:
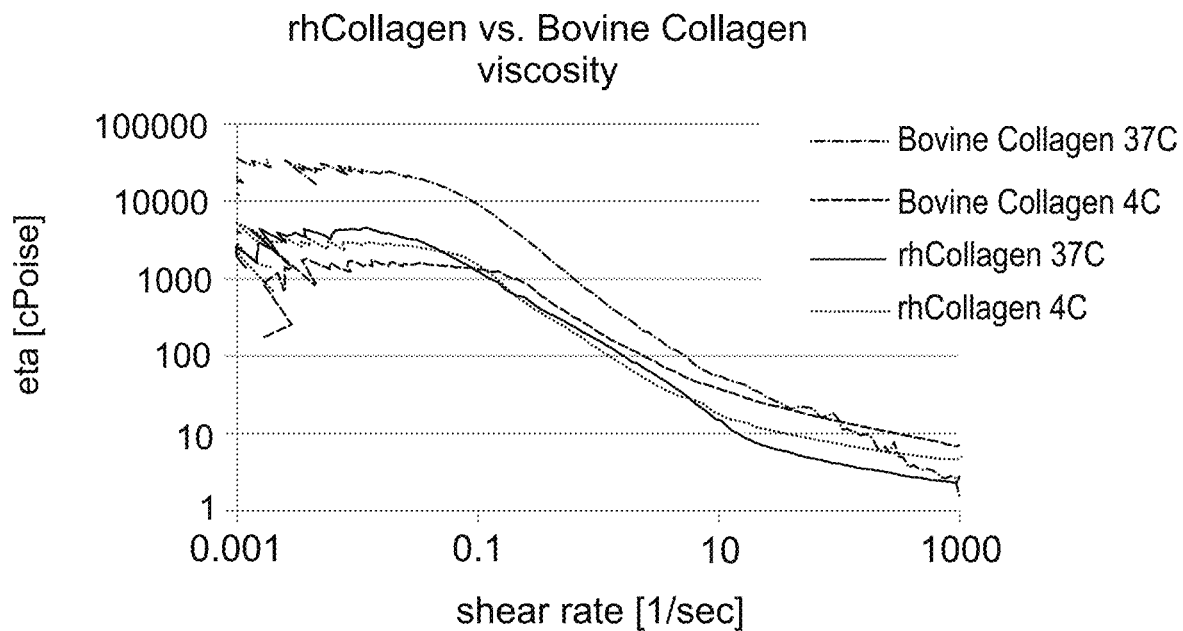

FIG. 2 presents comparative plots showing the viscosity as a function of shear rate, of a solution of 2.7 mg/mL bovine collagen in DPBS (solid line), and of a solution of 2.79 mg/mL rhCollagen in DPBS (dashed line), as measured at 4° C. and at 37° C.

Figure 3:
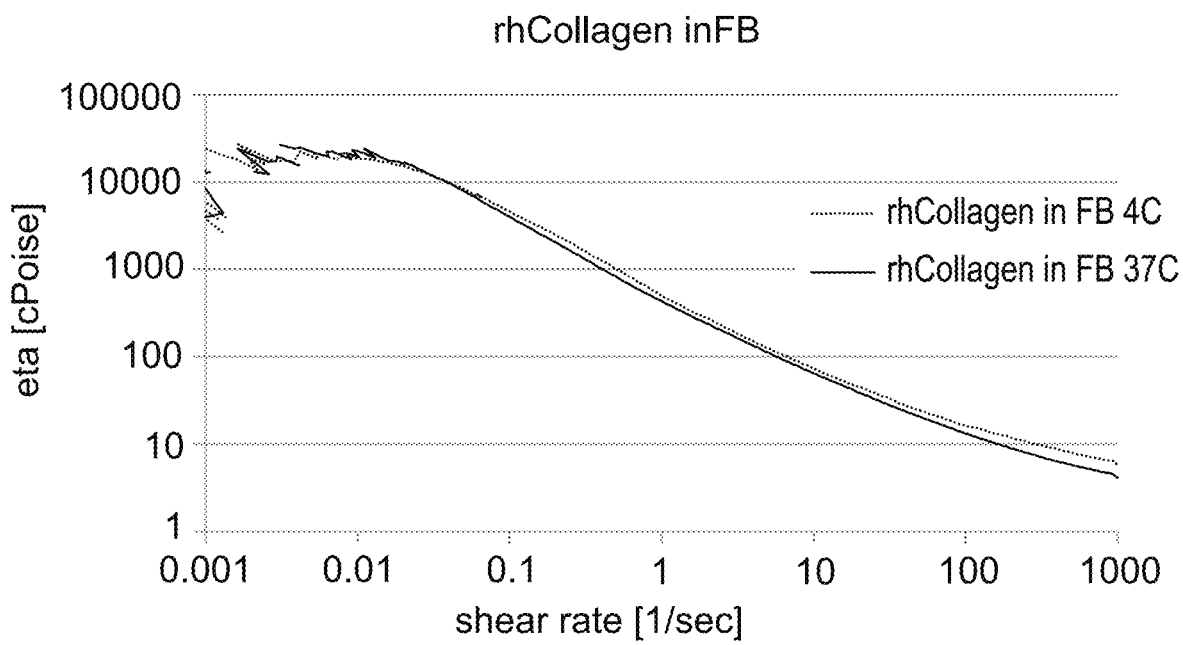

FIG. 3 presents comparative plots showing the viscosity as a function of shear rate, of a solution of 3.4 mg/mL rhCollagen in FB, as measured at 4° C. and at 37° C., demonstrating an identical shear thinning behavior at both temperatures.

Figure 4:
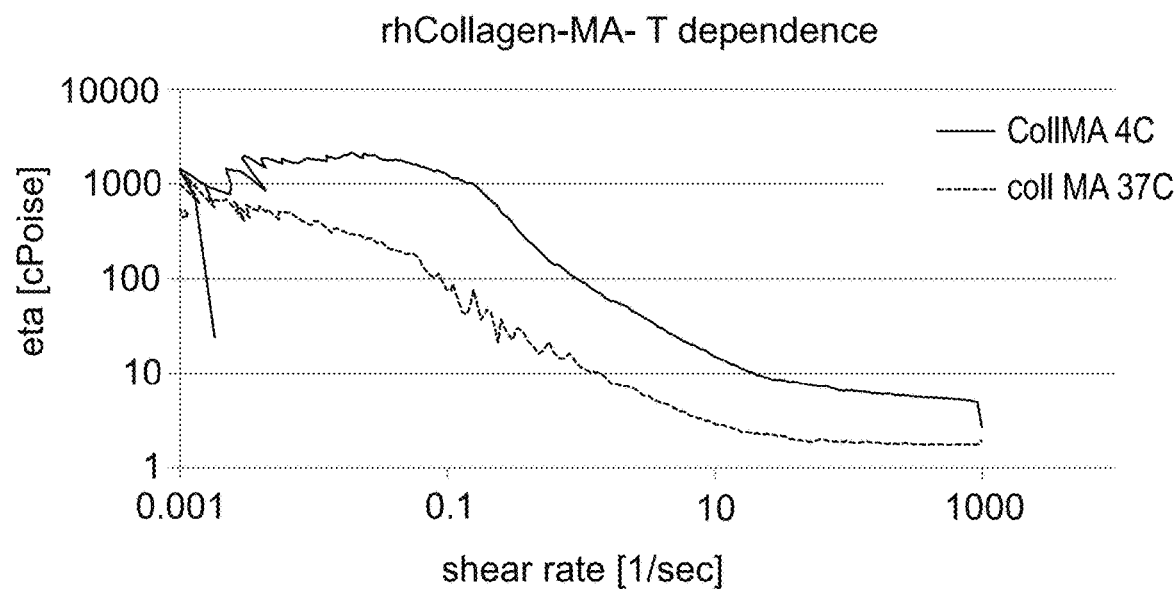

FIG. 4 presents comparative plots showing the viscosity as a function of shear rate, of a solution of 10 mg/mL rhCollagen-MA in DPBS as measured at 4° C. and at 37° C., demonstrating a shear thinning behavior at both temperatures.

Figure 5:
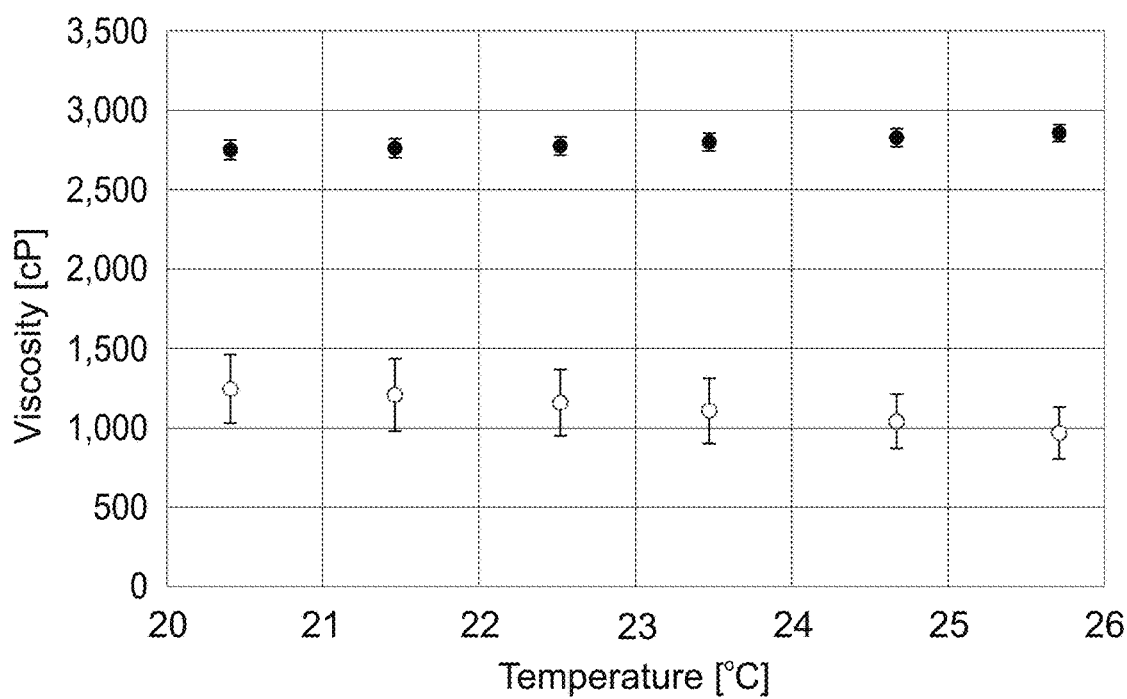

FIG. 5 presents comparative plots showing the viscosity as function of temperature increase, of a solution of 10 mg/ml rhCollagen-MA in 20 mM acetic acid (white circles) and an equivalent solution of bovine collagen methacrylate ink (bovine type I collagen methacrylate) (black circles), measured in a rheometer using rotational temperature steps CR mode with shear rate of 5 [1/sec].

Figure 6A:
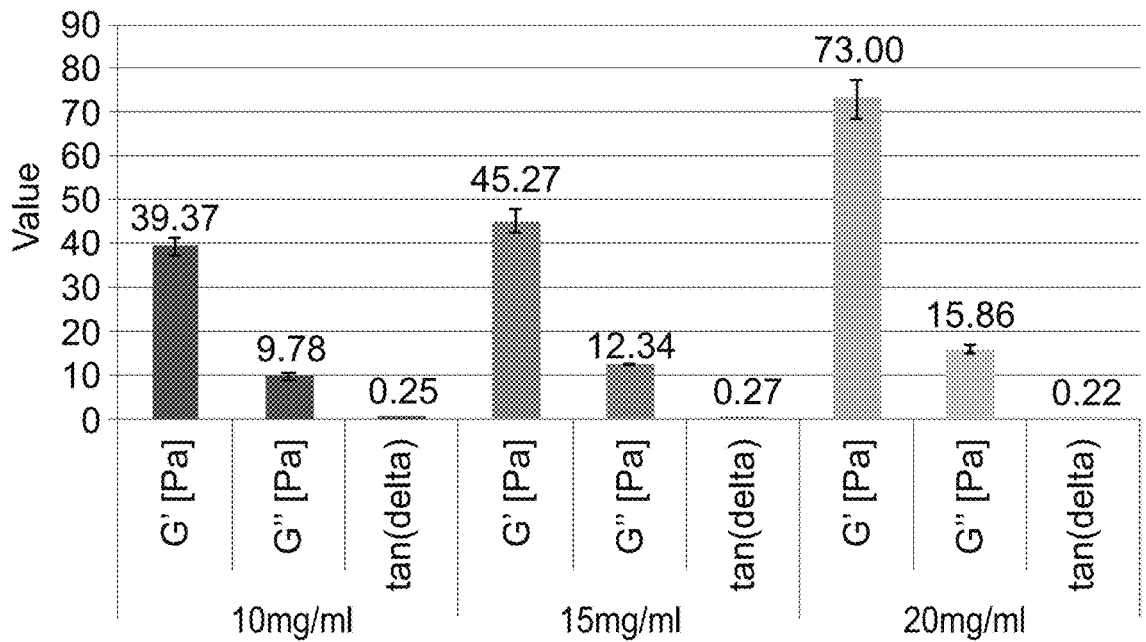
Figure 6B:
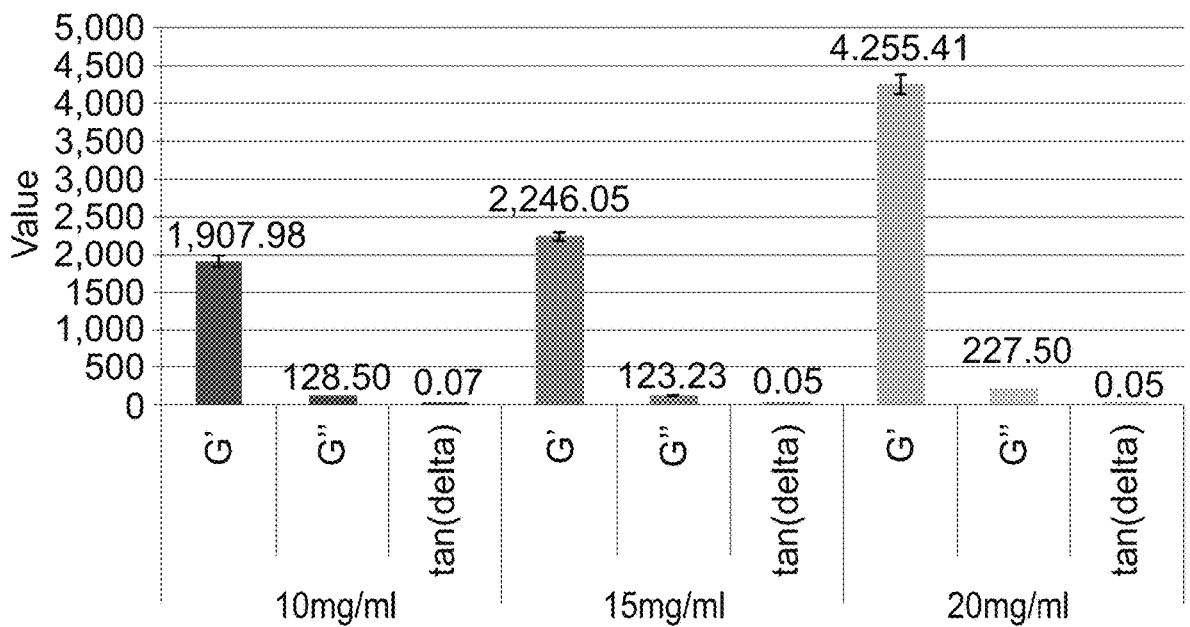

FIGS. 6A-B are bar graphs presenting the storage and loss moduli and tan phase shift angle (tan delta) of rhCollagen-MA formulation at different concentrations before (FIG. 6A) and after (FIG. 6B) photocuring.

Figure 7:
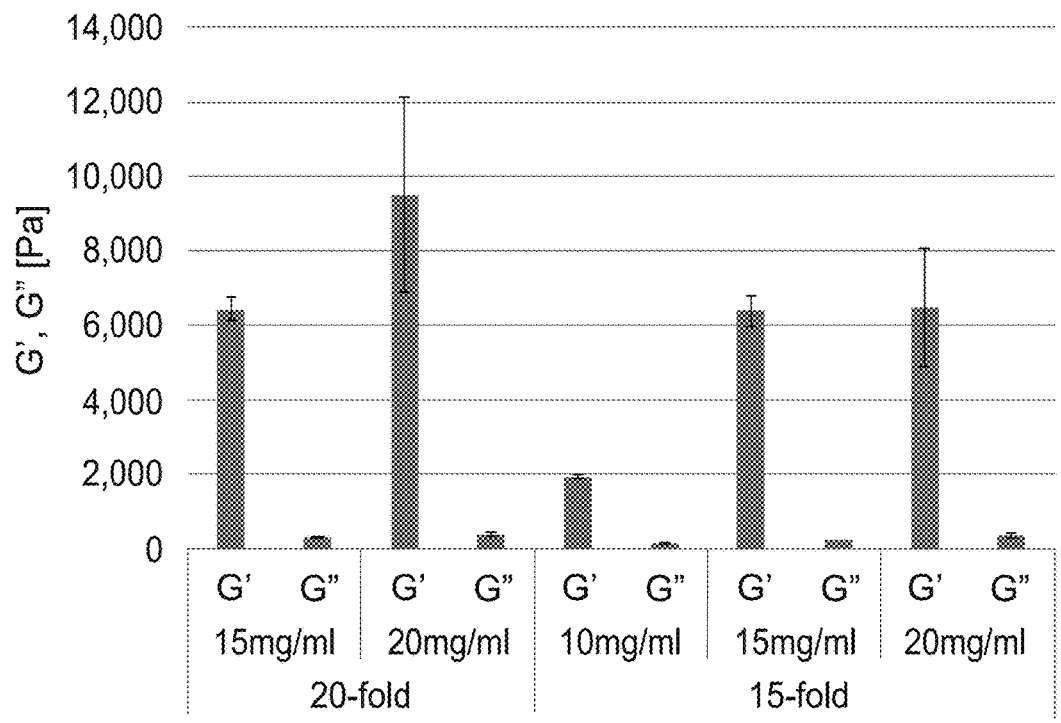

FIG. 7 is a bar graph showing the G' and G" values of cured objects prepared from various formulations of fibrillar rhCollagen-MA, at 37° C., recorded in frequency sweep test and plotted at 1 Hz.

Figure 8:
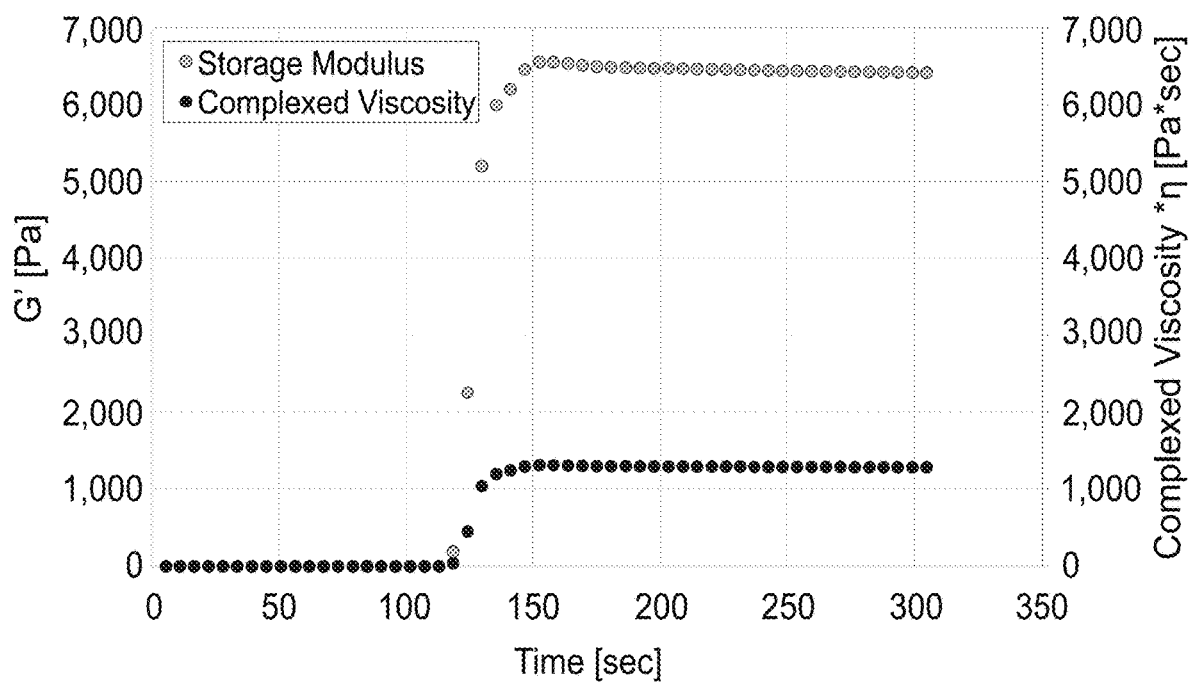

FIG. 8 presents plots showing G' and complexed viscosity values measured over time of cured objects prepared from a solution of 15 mg/ml rhCollagenn-MA in 10 mM HCl, as recorded in a rheometer using Oscillation with 7% strain and 5 rad/sec angular frequency.

Figure 9:
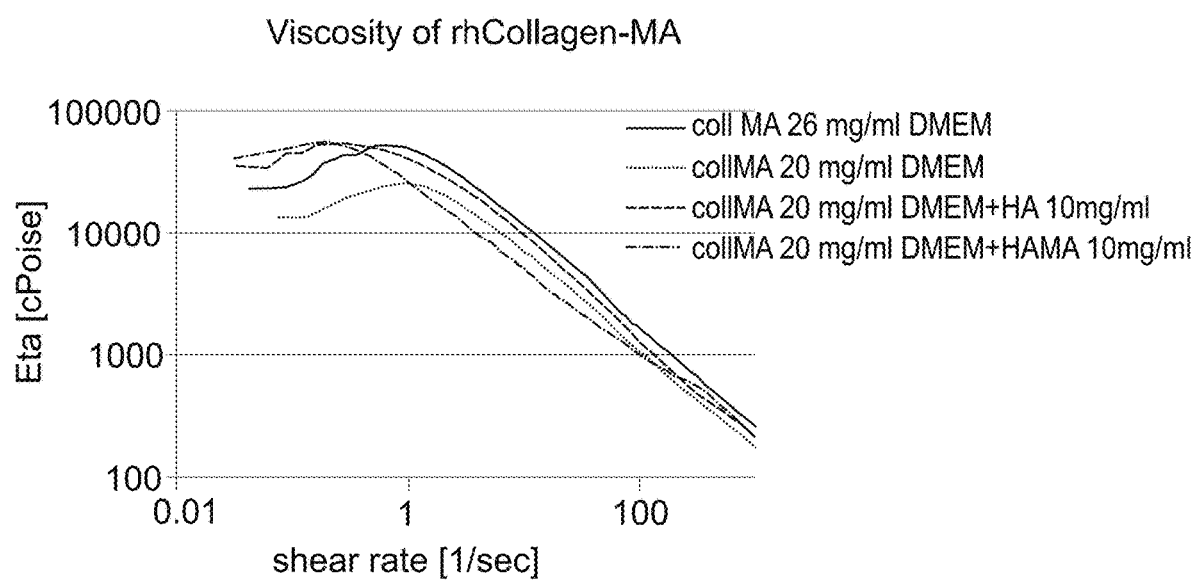

FIG. 9 presents comparative plots showing the viscosity as a function of shear rate of a solution containing rhCollagen-MA, rhCollagen-MA+hyaluronic acid (HA), or rhCollagen-MA and hyaluronic acid-MA (HAMA) in DMEM.

Figure 10:
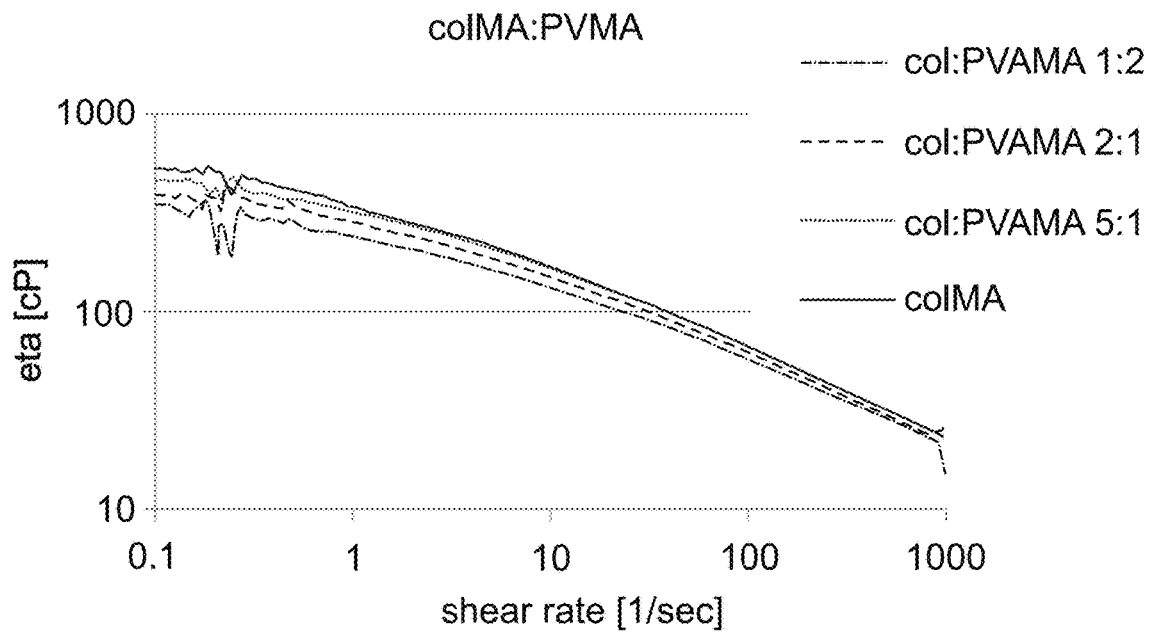

FIG. 10 presents comparative plots showing the viscosity as a function of shear rate of a solution of 5 mg/ml rbCollagen-MA (colMA), and of solutions of 5 mg/ml rbCollagen-MA and Polyvinyl alcohol methacrylate (PVAMA), at rhCollagen-MA:PVAMA weight ratio of 5:1, 2:1 or 1:2. All solutions are in 0.1M PB+11.3 mM NaCl, pH 7.4.

Figure 11:
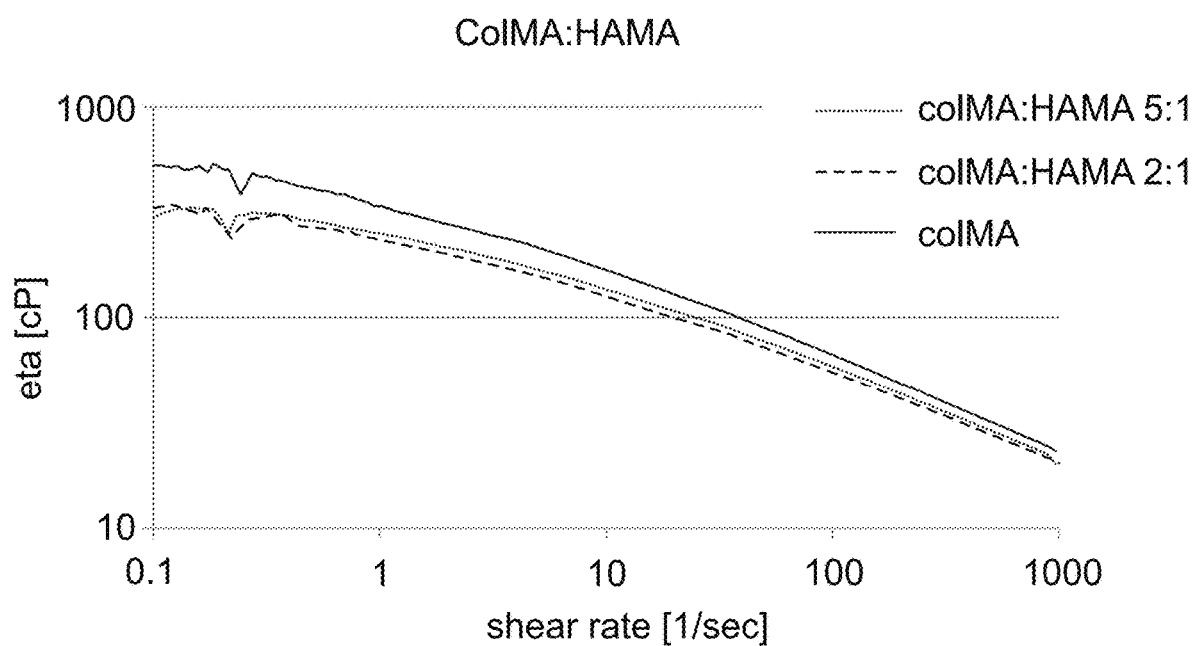

FIG. 11 presents comparative plots showing the viscosity as a function of shear rate of a solution of 5 mg/ml rhCollagen-MA (colMA) and of solutions of 5 mg/ml rhCollagen-MA and HAMA at rhCollagen-MA:HAMA weight ratio of 5:1 or 2:. All solutions are in 0.1MPB+11.3 mM NaCl pH 7.4.

Figure 12:
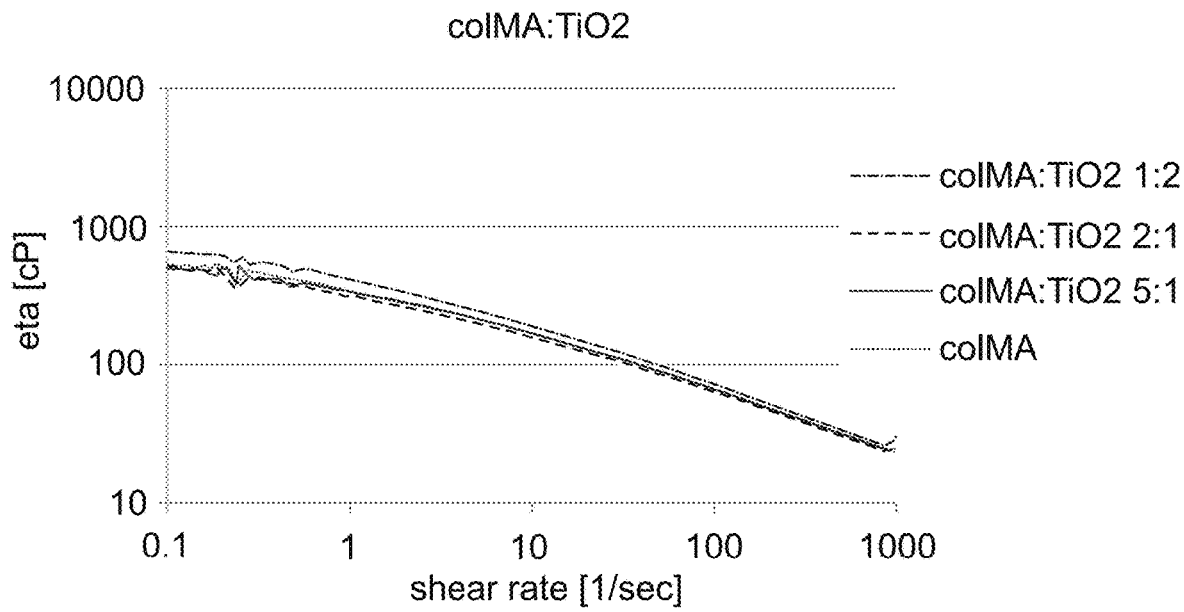

FIG. 12 presents comparative plots showing the viscosity as a function of shear rate of a solution of 5 mg/ml rhCollagen-MA (colMA) and of solutions of 5 mg/ml rhCollagen-MA and $TiO_2$ at rhCollagen-MA:$TiO_2$ weight ratio of 5:1, 2:1 (red dashed curve), or 1:2. All solutions are in 0.1MPB+11.3 mM NaCl pH 7.4.

Figure 13:
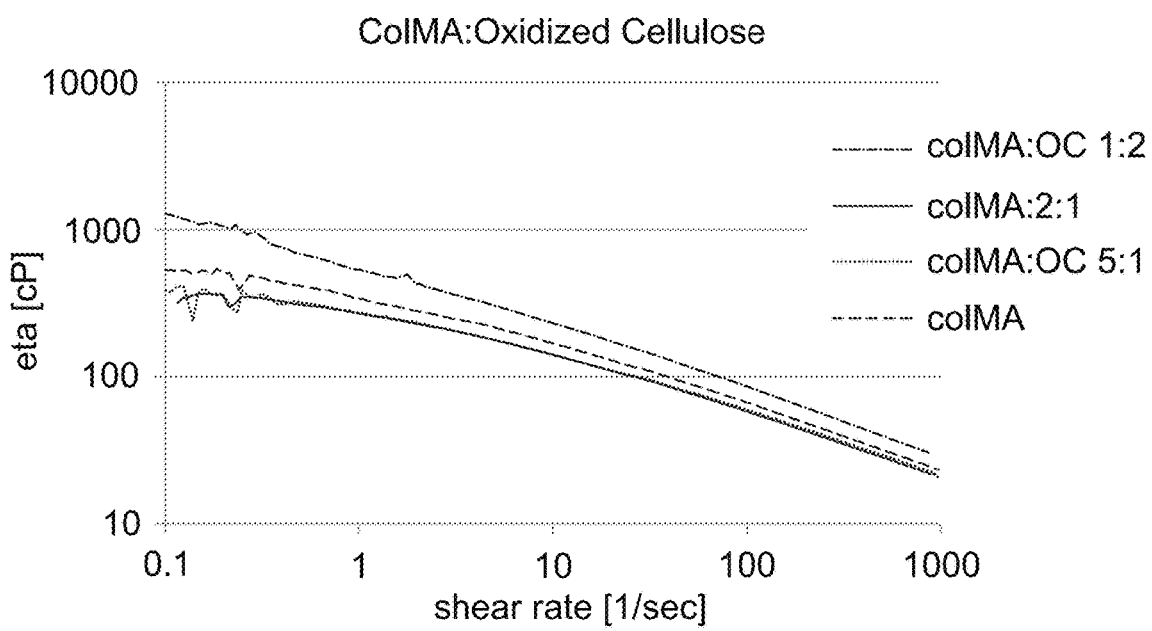

FIG. 13 presents comparative plots showing the viscosity as a function of shear rate of a solution of 5 mg/ml rhCollagen-MA (colMA) and of solutions of 5 mg/ml rhCollagen-MA and oxidized cellulose at rhCollagen-MA: oxidized cellulose weight ratio of 5:1, 2:1, or 1:2. All solutions are in 0.1MPB+11.3 mM NaCl pH 7.4.

Figure 14:
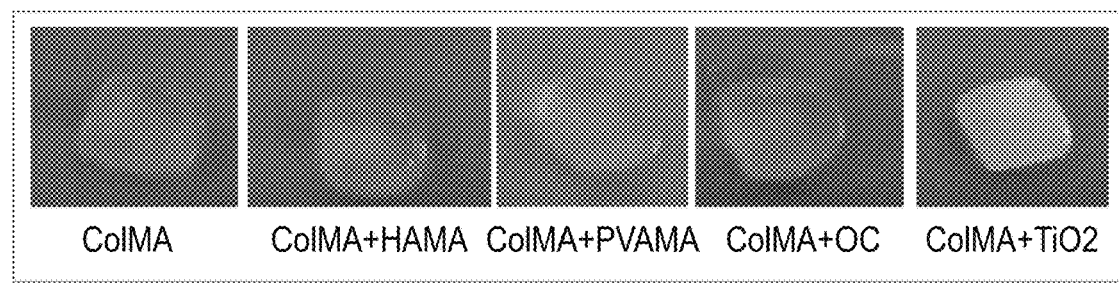

FIG. 14 presents photographs of cured objects (scaffolds) obtained from formulations containing rhCollagen-MA and various additives at rhCollagen-MA:additive weight ratio of 2:1.

Figure 15:
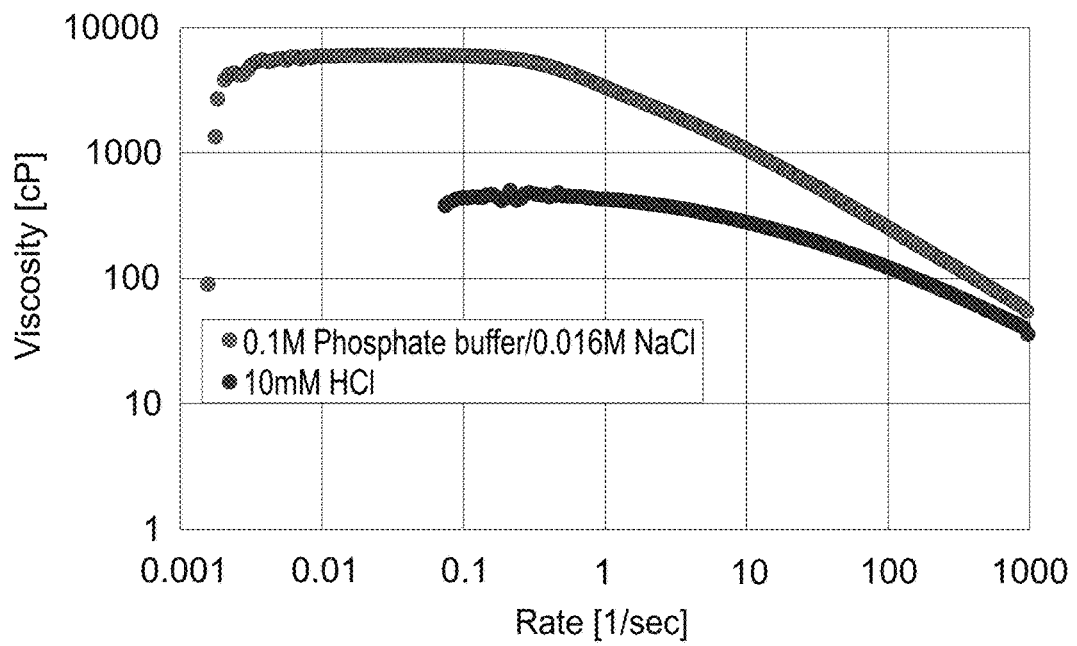

FIG. 15 presents plots showing the viscosity as a function of shear rate of solutions containing 10 mg/ml rhCollagen-MA in phosphate buffer 0.1M/NaCl 0.016M (light grey) and in 10 mM HCl (dark grey) solutions before curing, as recorded in the rheometer using Rotational CR mode at R.T., demonstrating a more pronounced shear thinning behavior of the PBS solution.

Figure 16:
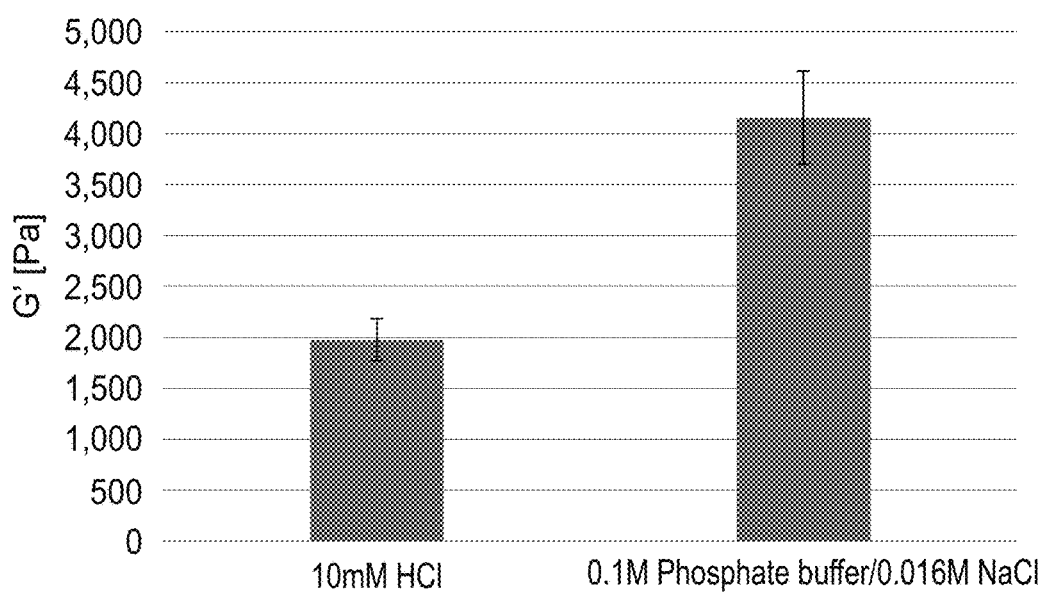

FIG. 16 is a bar graph showing G' values of objects obtained upon curing solutions containing 10 mg/ml rhCollagen-MA in phosphate buffer 0.1M/NaCl 0.016M and in 10 mM HCl, as recorded in the rheometer using Oscillation CR mode at 37° C.

Figure 17:
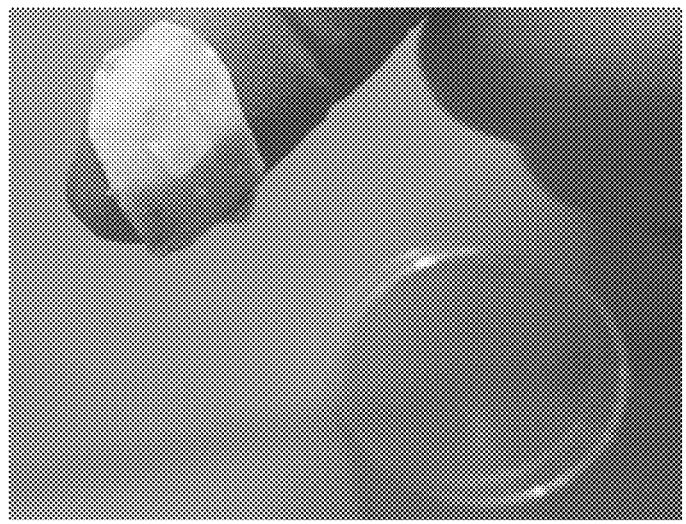
Figure 18:
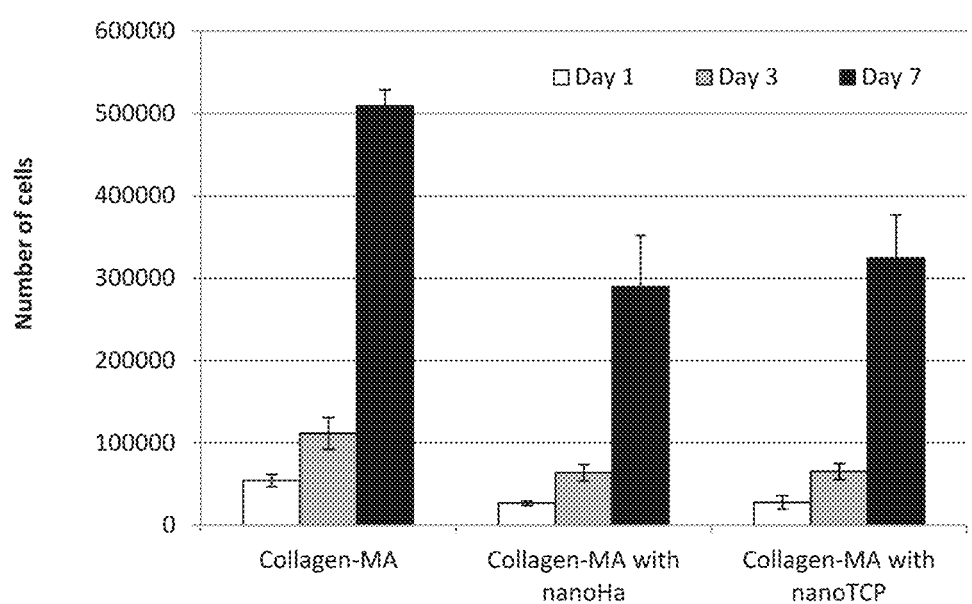

FIG. 17 presents a photograph of a scaffold prepared from a solution of rhCollagen-MA integrated into a mouse skin patch (ex-vivo) following illumination with a white LED torch through the skin. The skin patch was illuminated on its external side, while the rhCollagen-MA solution was dispensed in a mold underneath the skin FIG. 18 is a bar graph showing the proliferation of normal human dermal fibroblasts seeded in scaffolds made of a solution containing rhCollagen-MA and calcium phosphate particles.

DESCRIPTION OF SPECIFIC EMBODIMENTS OF THE INVENTION

The present invention, in some embodiments thereof, relates to additive manufacturing and, more particularly, but not exclusively, to three-dimensional (3D) bioprinting of 3D objects using a collagen-based building material.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have surprisingly uncovered that recombinant human collagen (rhCollagen) is much more tolerant to temperature and ionic strength conditions than tissue extracted-collagen. The present inventors have uncovered that an aqueous solution of rhCollagen does not form gels at temperatures above 20° C., and even at 37° C., and that its viscosity is minimally affected at varying conditions, for example, at acidic conditions, or at a salt concentration above 50 mM.

FIGS. 2 and 3 demonstrate the similar viscosity profile at increasing shear rate of an rhCollagen solution at different temperatures, and FIG. 2 further demonstrates the different viscosity profile observed at different temperatures for an aqueous solution of a tissue-extracted collagen, and particularly the substantially higher viscosity of the tissue-extracted collagen solution at low shear rates.

The present inventors have realized that these properties of rhCollagen can be advantageously utilized in additive manufacturing processes (e.g., 3D-bioprinting), by allowing performing such processes at conditions that are compatible with biological additives (e.g., physiological temperature and ionic strength, lower applied shear force), while avoiding the need to cool the additive manufacturing system, and while having a better control on the fluidity of the modeling material formulation.

While reducing the present invention to practice, the present inventors have successfully generated curable groups (e.g., (meth)acrylic groups) as substituents of amino acid residues (e.g., lysine residues) of the rhCollagen, and have shown that more than 80% of the lysine residues were modified to feature a methacrylamide group instead of amine group in the side chain thereof, as is exemplified in FIG. 1 and in Table 1.

The rhCollagen that features one or more, preferably a plurality of, curable groups such as (meth)acrylic groups as described herein is also referred to herein throughout, interchangeably, as "curable rhCollagen" or simply as "curable collagen".

An aqueous solution of the curable rhCollagen was found to exhibit the same relatively low viscosity at low shear rates, and a similar shear-thinning behavior, as exemplified in FIG. 4. Moreover, the curable rhCollagen solution was shown to exhibit a thermal-thinning behavior within a temperature range of working temperatures usable in additive manufacturing processes, and suitable viscosities at this temperature range, as opposed to a thermal-thickening behavior and high viscosities exhibited by a curable tissue-extracted collagen solution, as can be seen in FIG. 5.

The curable rhCollagen solution was further shown to exhibit good curability and curing stability, providing a cured material with desired mechanical properties, as shown in FIGS. 6A-B, 7 and 8.

The advantageous properties of the curable rhCollagen were shown to be maintained also in the presence of variable additives, and when used in different solutions (aqueous carriers), as shown in FIGS. 10-16.

The curable rhCollagen was shown to perform successfully in an in vitro model of transdermal application, as shown in FIG. 17, and as biocompatible, as shown in FIG. 18.

Embodiments of the present invention therefore relate to a composition that comprises a curable recombinant human collagen, to a formulation that comprises a curable recombinant human collagen, and to additive manufacturing processes utilizing same for manufacturing three-dimensional (3D) objects featuring a collagen-based material.

Additive Manufacturing:

According to an aspect of some embodiments of the present invention, there is provided a process (a method) of additive manufacturing (AM) of a three-dimensional object. According to embodiments of this aspect, the method is effected by sequentially forming a plurality of layers in a configured pattern corresponding to the shape of the object, thereby forming the object. According to embodiments of this aspect, formation of each layer is effected by dispensing at least one uncured building material, and exposing the dispensed building material to a curing condition to thereby form a hardened (cured) material.

Herein throughout, the phrase "building material" encompasses the phrases "uncured building material" or "uncured building material formulation" and collectively describes the materials that are dispensed by sequentially forming the layers, as described herein. This phrase encompasses uncured materials which form the final object, namely, one or more uncured modeling material formulation(s), and optionally also uncured materials used to form a support, namely uncured support material formulations. The building material can also include non-curable materials that preferably do not undergo (or are not intended to undergo) any change during the process, for example, biological materials or components (other than a curable collagen as described herein) and/or other agents or additives as described herein.

The building material that is dispensed to sequentially form the layers as described herein is also referred to herein interchangeably as "printing medium" or "bioprinting medium".

An uncured building material can comprise one or more modeling material formulations, and can be dispensed such that different parts of the object are made upon hardening (e.g., curing) of different modeling formulations, and hence are made of different hardened (e.g., cured) modeling materials or different mixtures of hardened (e.g., cured) modeling materials.

The method of the present embodiments manufactures three-dimensional objects in a layerwise manner by forming a plurality of layers in a configured pattern corresponding to the shape of the object.

Each layer is formed by an additive manufacturing apparatus which scans a two-dimensional surface and patterns it. While scanning, the apparatus visits a plurality of target locations on the two-dimensional layer or surface, and decides, according to a pre-set algorithm, for each target location or a group of target locations, whether or not the target location or group of target locations is to be occupied by a building material, and which type of a building material is to be delivered thereto. The decision is made according to a computer image of the surface.

When the AM is by three-dimensional inkjet printing, an uncured building material, as defined herein, is dispensed from a dispensing head having a set of nozzles to deposit building material in layers on a supporting structure. The AM apparatus thus dispenses building material in target locations which are to be occupied and leaves other target locations void. The apparatus typically includes a plurality of dispensing heads, each of which can be configured to dispense a different building material (for example, different modeling material formulations, each containing a different biological component; or each containing a different curable material; or each containing a different concentration of a curable material, and/or different support material formulations). Thus, different target locations can be occupied by different building materials (e.g., a modeling formulation and/or a support formulation, as defined herein).

The final three-dimensional object is made of the hardened modeling material or a combination of hardened modeling materials or a combination of hardened modeling material/s and support material/s or modification thereof (e.g., following curing). All these operations are well-known to those skilled in the art of additive manufacturing (also known as solid freeform fabrication).

In some exemplary embodiments of the invention an object is manufactured by dispensing a building material that comprises two or more different modeling material formulations, each modeling material formulation from a different dispensing head of the AM apparatus. The modeling material formulations are optionally and preferably deposited in layers during the same pass of the dispensing heads. The modeling material formulations and/or combination of formulations within the layer are selected according to the desired properties of the object.

An exemplary process according to some embodiments of the present invention starts by receiving 3D printing data corresponding to the shape of the object. The data can be received, for example, from a host computer which transmits digital data pertaining to fabrication instructions based on computer object data, e.g., in a form of a Standard Tessellation Language (STL) or a StereoLithography Contour (SLC) format, Virtual Reality Modeling Language (VRML), Additive Manufacturing File (AMF) format, Drawing Exchange Format (DXF), Polygon File Format (PLY), Digital Imaging and Communications in Medicine (DICOM) or any other format suitable for Computer-Aided Design (CAD).

The process continues by dispensing the building material as described herein in layers, on a receiving medium, using one or more dispensing (e.g., printing) heads, according to the printing data.

The dispensing can be in a form of droplets, or a continuous stream, depending on the additive manufacturing methodology employed and the configuration of choice.

The receiving medium can be a tray of a printing system, or a supporting article or medium made of, or coated by, a biocompatible material, such as support media or articles commonly used in bioprinting, or a previously deposited layer.

In some embodiments, the receiving medium comprises a sacrificial hydrogel or other biocompatible material as a mold to embed the printed object, and is thereafter removed by chemical, mechanical or physical (e.g., heating or cooling) means. Such sacrificial hydrogels can be made of, for example, a Pluronic material or of Gelatin.

Once the uncured building material is dispensed on the receiving medium according to the 3D data, the method optionally and preferably continues by hardening the dispensed formulation(s). In some embodiments, the process continues by exposing the deposited layers to a curing condition. Preferably, the curing condition is applied to each individual layer following the deposition of the layer and prior to the deposition of the previous layer.

As used herein, the term "curing" describes a process in which a formulation is hardened. The hardening of a formulation typically involves an increase in a viscosity of the formulation and/or an increase in a storage modulus of the formulation (G'). In some embodiments, a formulation which is dispensed as a liquid becomes solid or semi-solid (e.g., gel) when hardened. A formulation which is dispensed as a semi-solid (e.g., soft gel) becomes solid or a harder or stronger semi-solid (e.g., strong gel) when hardened.

The term "curing" as used herein encompasses, for example, polymerization of monomeric and/or oligomeric materials and/or cross-linking of polymeric chains (either of a polymer present before curing or of a polymeric material formed in a polymerization of the monomers or oligomers). The product of a curing reaction is therefore typically a polymeric material and/or a cross-linked material. This term, as used herein, encompasses also partial curing, for example, curing of at least 20% or at least 30% or at least 40% or at least 50% or at least 60% or at least 70% of the formulation, as well as 100% of the formulation.

Herein, the phrase "a condition that affects curing" or "a condition for inducing curing", which is also referred to herein interchangeably as "curing condition" or "curing inducing condition" describes a condition which, when applied to a formulation that contains a curable material, induces a curing as defined herein. Such a condition can include, for example, application of a curing energy, as described hereinafter to the curable material(s), and/or contacting the curable material(s) with chemically reactive components such as catalysts, co-catalysts, and activators.

When a condition that induces curing comprises application of a curing energy, the phrase "exposing to a curing condition" and grammatical diversions thereof means that the dispensed layers are exposed to the curing energy and the exposure is typically performed by applying a curing energy to the dispensed layers.

A "curing energy" typically includes application of radiation or application of heat.

The radiation can be electromagnetic radiation (e.g., ultraviolet or visible light), or electron beam radiation, or ultrasound radiation or microwave radiation, depending on the materials to be cured. The application of radiation (or irradiation) is effected by a suitable radiation source. For example, an ultraviolet or visible or infrared or Xenon or mercury or lamp, or LED source, can be employed, as described herein.

A curable material or system that undergoes curing upon exposure to radiation is referred to herein interchangeably as "photopolymerizable" or "photoactivatable" or "photocurable".

When the curing energy comprises heat, the curing is also referred to herein and in the art as "thermal curing" and comprises application of thermal energy. Applying thermal energy can be effected, for example, by heating a receiving medium onto which the layers are dispensed or a chamber hosting the receiving medium, as described herein. In some embodiments, the heating is effected using a resistive heater.

In some embodiments, the heating is effected by irradiating the dispensed layers by heat-inducing radiation. Such irradiation can be effected, for example, by means of an IR lamp or Xenon lamp, operated to emit radiation onto the deposited layer.

In some embodiments, heating is effected by infrared radiation applied by a ceramic lamp, is for example, a ceramic lamp that produces infrared radiation of from about 3 µm to about 4 µm, e.g., about 3.5 µm.

A curable material or system that undergoes curing upon exposure to heat is referred to herein as "thermally-curable" or "thermally-activatable" or "thermally-polymerizable".

In some of any of the embodiments described herein, hardening the dispensed formulation(s) comprises exposing the dispensed formulation to a curing condition as described herein in any of the respective embodiments, for example, to irradiation (illumination).

In some embodiments, the exposure to a curing condition is for a short time period, for example, a time period of less than 3 minutes, less than 300 seconds, for example, of from 10 seconds to 240 seconds, or from 10 seconds to 120 seconds, to from 10 seconds to 60 seconds, including an intermediate values and subranges therebetween.

In some of any of the embodiments described herein, the method further comprises exposing the cured modeling material formulation(s) either before or after removal of a support material formulation, if such has been included in the building material, to a post-treatment condition. The post-treatment condition is typically aimed at further hardening the cured modeling material(s). In some embodiments, the post-treatment hardens a partially-cured formulation to thereby obtain a completely cured formulation.

In some embodiments, the post-treatment is effected by exposure to heat or radiation, as described in any of the respective embodiments herein.

Some embodiments contemplate the fabrication of an object by dispensing different formulations from different dispensing heads. These embodiments provide, inter alia, the ability to select formulations from a given number of formulations and define desired combinations of the selected formulations and their properties.

According to the present embodiments, the spatial locations of the deposition of each formulation with the layer are defined, either to effect occupation of different three-dimensional spatial locations by different formulations, or to effect occupation of substantially the same three-dimensional location or adjacent three-dimensional locations by two or more different formulations so as to allow post deposition spatial combination of the formulations within the layer.

The present embodiments thus enable the deposition of a broad range of material combinations, and the fabrication of an object which may consist of multiple different combinations of modeling material formulations, in different parts of the object, according to the properties desired to characterize each part of the object.

A system utilized in additive manufacturing may include a receiving medium and one or more dispensing heads. The receiving medium can be, for example, a fabrication tray that may include a horizontal surface to carry the material dispensed from the printing head. In some embodiments, the receiving medium is made of, or coated by, a biocompatible material, as described herein.

The dispensing head may be, for example, a printing head having a plurality of dispensing nozzles arranged in an array of one or more rows along the longitudinal axis of the dispensing head. The dispensing head may be located such that its longitudinal axis is substantially parallel to the indexing direction.

The additive manufacturing system may further include a controller, such as a microprocessor to control the AM process, for example, the movement of the dispensing head according to a pre-defined scanning plan (e.g., a CAD configuration converted to a Standard Tessellation Language (STL) format and programmed into the controller). The dispensing head may include a plurality of jetting nozzles. The jetting nozzles dispense material onto the receiving medium to create the layers representing cross sections of a 3D object.

In addition to the dispensing head, there may be a source of curing energy, for curing the dispensed building material. The curing energy is typically radiation, for example, UV radiation or heat radiation. Alternatively, there may be means for providing a curing condition other than electromagnetic or heat radiation, for example, means for cooling the dispensed building material of for contacting it with a reagent that promotes curing.

Additionally, the AM system may include a leveling device for leveling and/or establishing the height of each layer after deposition and at least partial solidification, prior to the deposition of a subsequent layer.

According to the present embodiments, the additive manufacturing method described herein is for bioprinting a biological object.

As used herein, "bioprinting" means practicing an additive manufacturing process while utilizing one or more bio-ink formulation(s) that comprise(s) biological components, as described herein, via methodology that is compatible with an automated or semi-automated, computer-aided, additive manufacturing system as described herein (e.g., a bioprinter or a bioprinting system).

Herein throughout, the phrase "modeling material formulation", which is also referred to herein interchangeably as "modeling formulation" or "modeling material composition" or "modeling composition", or simply as a "formulation", or a "composition", describes a part or all of the uncured building material (printing medium) which is dispensed so as to form the final object, as described herein. The modeling formulation is an uncured modeling formulation, which, upon exposure to a curing condition, forms the object or a part thereof.

In the context of bioprinting, an uncured building material comprises at least one modeling formulation that comprises one or more biological components or materials (e.g., a curable rhCollagen as described herein), and is also referred to herein and in the art as "bio-ink" or "bio-ink formulation".

In some embodiments, the bioprinting comprises sequential formation of a plurality of layers of the uncured building material in a configured pattern, preferably according to a three-dimensional printing data, as described herein. At least one, and preferably most or all, of the formed layers (before hardening or curing) comprise(s) one or more biological component(s) as described herein (e.g., a curable rhCollagen as described herein). Optionally, at least one of the formed layers (before hardening or curing) comprises one or more non-biological curable materials, and/or non-curable biological or non-biological components, preferably biocompatible materials which do not interfere (e.g., adversely affect) with the biological and/or structural features of the biological components (e.g., collagen) in the printing medium and/or bio-ink.

In some embodiments, the components in the bio-ink or the printing medium, e.g., non-curable and curable materials, and/or the curing condition applied to effect curing, are selected such that they do not significantly affect structural and/or functional properties of the biological components in the bio-ink or printing medium.

In some of any of the embodiments described herein, the building material (e.g., the printing medium) comprises modeling material formulation(s) (bio-ink) and optionally support material formulation(s), and all are selected to include materials or combination of materials that do not interfere with the biological and/or structural features of the biological components.

In some of any of the embodiments described herein, the bioprinting method is configured to effect formation of the layers under conditions that do not significantly affect structural and/or functional properties of the biological components in the bio-ink.

In some embodiments, a bioprinting system for effecting a bioprinting process/method as described herein is configured so as to allow formation of the layers under conditions that do not significantly affect structural and/or functional properties of the biological components in the bio-ink.

In some of any of the embodiments described herein, the additive manufacturing (e.g., bioprinting) process and system are configured such that the process parameters (e.g., temperature, shear forces, shear strain rate) do not interfere with (do not substantially affect) the functional and/or structural features of the biological components.

In some of any of the embodiments described herein, the additive manufacturing process (the bioprinting) is performed at a temperature of at least 10° C., or of at least 20° C., for example, at a temperature that ranges from about 10 to about 40° C., preferably from about 10° C. to 37° C., or from about 20° C. to 37° C., or from about 20° C. to about 30° C., or from about 20° C. to about 28° C., or from about 20° C. to about 25° C., including any intermediate values and subranges therebetween, or at room temperature, or at 37° C.

In some of any of the embodiments described herein, the above-indicated temperatures/temperature ranges are the temperatures at which the building material (e.g., at least a modeling material formulation that comprises a biological component as described herein) are dispensed, that is, a temperature of a dispensing head in the AM system and/or a temperature at which the modeling material formulation is maintained prior to passing in the dispensing head.

In some of any of the embodiments described herein, the AM process is performed without cooling the AM system (e.g., without cooling the dispensing heads and/or a modeling material formulation), to a temperature below room temperature, e.g., a temperature lower than 20° C. or lower than 10° C., or lower than 5° C. (e.g., 4° C.).

In some of any of the embodiments described herein, the AM system is devoid of means for cooling the system or a part thereof (e.g., means for cooling the dispensing heads and/or the modeling material formulation), to a temperature below room temperature, e.g., a temperature lower than 20° C. or lower than 10° C., or lower than 5° C. (e.g., 4° C.).

In some of any of the embodiments described herein, the additive manufacturing process (bioprinting) is performed while applying a shear force that does adversely affect structural and/or functional properties of biological components (e.g., cells). Applying the shear force can be effected by passing the building material (e.g., at least a modeling material formulation that comprises a biological component as described herein) through the dispensing head, and is to be regarded also as subjecting the building material to shear force.

As discussed herein and demonstrated in the Examples section that follow, embodiments of the present invention allow to perform AM bioprinting processes under conditions that do not affect the functional and/or structural features of biological components included in the bio-ink (e.g., at low shear force and room temperature or a physiological temperature), while maintaining the required fluidity (a viscosity that imparts fluidity, e.g., lower than 10,000 centipoises or lower than 5,000 centipoises, or lower than 2,000 centipoises), and while further maintaining the curability of the dispensed building material. The embodiments of the present invention allow a successful operation of bioprinting using any of the known methodology, without being limited to the process parameters required for each such methodology.

The following describes exemplary AM bioprinting methodologies that are usable in the context of embodiments of the present invention.

A bioprinting method and a corresponding system can be any of the methods and systems known in the art for performing additive manufacturing, and exemplary such systems and methods are described hereinabove. A suitable method and system can be selected upon considering its printing capabilities, which include resolution, deposition speed, scalability, bio-ink compatibility and ease-of-use.

Exemplary suitable bioprinting systems usually contain a dispensing system (either equipped with temperature control module or at ambient temperature), and stage (a receiving medium), and a movement along the x, y and z axes directed by a CAD-CAM software. A curing source (e.g., a light or heat source) which applies a curing energy (e.g., by applying light or heat radiation) or a curing condition to the deposition area (the receiving medium) so as to promote curing of the formed layers and/or a humidifier, can also be included in the system. There are printers that use multiple dispensing heads to facilitate a serial dispensing of several materials.

Generally, bioprinting can be effected using any of the known techniques for additive manufacturing. The following lists some exemplary additive manufacturing techniques, although any other technique is contemplated.

3D Inkjet Printing:

3D Inkjet printing is a common type of 3D printer for both non-biological and biological (bioprinting) applications. Inkjet printers use thermal or acoustic forces to eject drops of liquid onto a substrate, which can support or form part of the final construct. In this technique, controlled volumes of liquid are delivered to predefined locations, and a high-resolution printing with precise control of (1) ink drops position, and (2) ink volume, which is beneficial in cases of microstructure-printing or when small amounts of bioreactive agents or drugs are added, is received. Inkjet printers can be used with several types of ink, for example, comprising multiple types of biological components and/or bioactive agents. Furthermore, the printing is fast and can be applied onto culture plates.

A bioprinting method that utilizes a 3D inkjet printing system can be operated using one or more bio-ink modeling material formulations as described herein, and dispensing droplets of the formulation(s) in layers, on the receiving medium, using one or more inkjet printing head(s), according to the 3D printing data.

Extrusion Printing:

This technique uses continuous beads of material rather than liquid droplets. These beads of material are deposited in 2D, the stage (receiving medium) or extrusion head moves along the z axis, and the deposited layer serves as the basis for the next layer. The most common methods for biological materials extrusion for 3D bioprinting applications are pneumatic or mechanical dispensing systems.

Stereolithography (SLA) and Digital Light Processing (DLP):

SLA and DLP are additive manufacturing technologies in which an uncured building material in a bath is converted into hardened material(s), layer by layer, by selective curing using a light source while the uncured material is later separated/washed from the hardened material. SLA is widely used to create models, prototypes, patterns, and production parts for a range of industries including for Bioprinting.

Laser-Assisted Printing:

Laser-assisted printing technique, in the version adopted for 3D bioprinting, and is based on the principle of laser-induced forward transfer (LIFT), which was developed to transfer metals and is now successfully applied to biological material. The device consists of a laser beam, a focusing system, an energy absorbing/converting layer and a biological material layer (e.g., cells and/or hydrogel) and a receiving substrate. A laser assisted printer operates by shooting a laser beam onto the absorbing layer which convert the energy into a mechanical force which drives tiny drops from the biological layer onto the substrate. A light source is then utilized to cure the material on the substrate.

Laser assisted printing is compatible with a series of viscosities and can print mammalian cells without affecting cell viability or cell function. Cells can be deposited at a density of up to $10^8$ cells/ml with microscale resolution of a single cell per drop.

Electrospinning:

Electrospinning is a fiber production technique, which uses electric force to draw charged threads of polymer solutions, or polymer melts.

Recombinant Human Collagen:

The term "collagen" as used herein, refers to a polypeptide having a triple helix structure and containing a repeating Gly-X-Y triplet, where X and Y can be any amino acid but are frequently the imino acids proline and hydroxyproline. According to one embodiment, the collagen is a type I, II, III, V, XI, or biologically active fragments therefrom.

A collagen of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to collagen sequences listed in Table A as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a particular embodiment, the collagen is a human collagen.

In another embodiment, the collagen comprises a naturally occurring amino acid sequence of human collagen.

Table A below lists examples of collagen NCBI sequence numbers.

TABLE A

| Exemplary procollagen NCBI sequence number | SEQ ID NO: |
| --- | --- |
| P02452 | 1 |
| P08123 | 2 |

The annotation of SEQ ID NO: 1 is as follows:
Amino acids 1-22—signal peptide;
Amino acids 23-161—N-terminal peptide;
Amino acids 162-1218—collagen alpha-1(I) chain;
Amino acids 1219-1464—C-terminal peptide;
The annotation of SEQ ID NO: 2 is as follows:
Amino acids 1-22—signal peptide;
Amino acids 23-79—N-terminal peptide;
Amino acids 80-1119—collagen alpha-2(I) chain;
Amino acids 1120-1366—C-terminal peptide.

According to one embodiment, the collagen of the present invention comprises a sufficient portion of its telopeptides such that under suitable conditions it is capable of forming fibrils.

Thus, for example, the collagen may be atelocollagen, a telocollagen or procollagen.

As used herein, the term "atelocollagen" refers to collagen molecules lacking both the N- and C-terminal propeptides typically comprised in procollagen and at least a portion of its telopeptides, but including a sufficient portion of its telopeptides such that under suitable conditions it is capable of forming fibrils.

The term "procollagen" as used herein, refers to a collagen molecule (e.g. human) that comprises either an N-terminal propeptide, a C-terminal propeptide or both. Exemplary human procollagen amino acid sequences are set forth by SEQ ID NOs: 3, 4, 5 and 6.

The term "telocollagen" as used herein, refers to collagen molecules that lack both the N- and C-terminal propeptides typically comprised in procollagen but still contain the telopeptides. The telopeptides of fibrillar collagen are the remnants of the N- and C-terminal propeptides following digestion with native N/C proteinases.

According to another embodiment, the collagen is devoid of its telopeptides and is not capable of undergoing fibrillogenesis.

According to another embodiment, the collagen is a mixture of the types of collagen above.

According to a particular embodiment, the collagen is genetically engineered using recombinant DNA technology (e.g. human collagen).

Methods of isolating collagen from animals are known in the art. Dispersal and solubilization of native animal collagen can be achieved using various proteolytic enzymes (such as porcine mucosal pepsin, bromelain, chymopapain, chymotrypsin, collagenase, ficin, papain, peptidase, proteinase A, proteinase K, trypsin, microbial proteases, and, similar enzymes or combinations of such enzymes) which disrupt the intermolecular bonds and remove the immunogenic non-helical telopeptides without affecting the basic, rigid triple-helical structure which imparts the desired characteristics of collagen (see U.S. Pat. Nos. 3,934,852; 3,121, 049; 3,131,130; 3,314,861; 3,530,037; 3,949,073; 4,233,360 and 4,488,911 for general methods for preparing purified soluble collagen). The resulting soluble collagen can be subsequently purified by repeated precipitation at low pH and high ionic strength, followed by washing and re-solubilization at low pH.

Plants expressing collagen chains and procollagen are known in the art, see for example, WO06035442A3; Merle et al., FEBS Lett. 2002 Mar. 27; 515(1-3):114-8. PMID: 11943205; and Ruggiero et al., 2000, FEBS Lett. 2000 Mar. 3; 469(1):132-6. PMID: 10708770; and U.S. Patent Applications Publication Nos. 2002/098578 and 2002/0142391, as well as U.S. Pat. No. 6,617,431 each of which are incorporated herein by reference.

It will be appreciated that the present invention also contemplates genetically modified forms of collagen/atelocollagen—for example collagenase-resistant collagens and the like [Wu et al., Proc Natl. Acad Sci, Vol. 87, p. 5888-5892, 1990].

Recombinant procollagen or telocollagen (e.g. human) may be expressed in any non-animal cell, including but not limited to plant cells and other eukaryotic cells such as yeast and fungus.

Plants in which procollagen or telocollagen may be produced (i.e. expressed) may be of lower (e.g. moss and algae) or higher (vascular) plant species, including tissues or isolated cells and extracts thereof (e.g. cell suspensions). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant procollagen is typically effected by stable or transient transformation with an exogenous polynucleotide sequence encoding human procollagen.

Exemplary polynucleotide sequences encoding human procollagen are set forth by SEQ ID NOs: 7, 8, 9 and 10.

Production of human telocollagen is typically effected by stable or transient transformation with an exogenous polynucleotide sequence encoding human procollagen and at least one exogenous polynucleotide sequence encoding the relevant protease. Alternatively, a protease may be added following isolation of the recombinant procollagen.

The stability of the triple-helical structure of collagen requires the hydroxylation of prolines by the enzyme prolyl-4-hydroxylase (P4H) to form residues of hydroxyproline within the collagen chain. Although plants are capable of synthesizing hydroxyproline-containing proteins, the prolyl hydroxylase that is responsible for synthesis of hydroxyproline in plant cells exhibits relatively loose substrate sequence specificity as compared with mammalian P4H. Thus, production of collagen containing hydroxyproline only in the Y position of Gly-X-Y triplets requires co-expression of collagen and human or mammalian P4H genes [Olsen et al, Adv Drug Deliv Rev. 2003 Nov. 28; 55(12):1547-67].

Thus, according to one embodiment, the procollagen or telocollagen is expressed in a subcellular compartment of a plant that is devoid of endogenous P4H activity.

As used herein, the phrase "subcellular compartment devoid of endogenous P4H activity" refers to any compartmentalized region of the cell which does not include plant P4H or an enzyme having plant-like P4H activity. According to one embodiment, the subcellular compartment is a vacuole, an apoplast or a chloroplast. According to a particular embodiment, the subcellular compartment is a vacuole. According to another embodiment, the subcellular compartment is an apoplast.

Accumulation of the expressed procollagen in a subcellular compartment devoid of endogenous P4H activity can be effected via any one of several approaches.

For example, the expressed procollagen/telocollagen can include a signal sequence for targeting the expressed protein to a subcellular compartment such as the apoplast or an organelle (e.g. chloroplast).

Examples of suitable signal sequences include the chloroplast transit peptide (included in Swiss-Prot entry P07689, amino acids 1-57) and the Mitochondrion transit peptide (included in Swiss-Prot entry P46643, amino acids 1-28). Targeting to the vacuole may be achieved by fusing the polynucleotide sequence encoding the collagen to a vacuolar targeting sequence—for example using the vacuolar targeting sequence of the thiol protease aleurain precursor (NCBI accession P05167

```
                                       (SEQ ID NO: 14)
MAHARVLLLALAVLATAAVAVASSSSFADSNPIRPVTDRAASTLA.
```

Typically, the polynucleotide sequence encoding the collagen also comprises an ER targeting sequence. In one embodiment, the ER targeting sequence is native to the collagen sequence. In another embodiment, the native ER targeting sequence is removed and a non-native ER targeting sequence is added. The non-native ER targeting sequence may be comprised in the vacuolar targeting sequence. It will be appreciated, for it to traverse the ER and move on to the vacuole, the collagen sequence should be devoid of an ER retention sequence.

Alternatively, the sequence of the procollagen can be modified in a way which alters the cellular localization of the procollagen when expressed in plants.

The present invention contemplates genetically modified cells co-expressing both human procollagen and a P4H. In one embodiment, the P4H is capable of correctly hydroxylating the procollagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both subunits are necessary to form an active enzyme, while the beta subunit also possesses a chaperon function.

The P4H expressed by the genetically modified cells of the present invention is preferably a human P4H. An exemplary polynucleotide sequence which encodes human P4H is SEQ ID Nos: 11 and 12. In addition, P4H mutants which exhibit enhanced substrate specificity, or P4H homologues can also be used. A suitable P4H homologue is exemplified by an Arabidopsis oxidoreductase identified by NCBI accession no: NP_179363.

Since it is essential that P4H co-accumulates with the expressed procollagen chain, the coding sequence thereof is preferably modified accordingly (e.g. by addition or deletion of signal sequences). Thus, the present invention contemplates using P4H polynucleotide sequences that are fused to vacuole targeting sequences. It will be appreciated that for targeting to the vacuole, when an endogenous ER retention sequence is present, it should be removed prior to expression.

In mammalian cells, collagen is also modified by Lysyl hydroxylase, galactosyltransferase and glucosyltransferase.

These enzymes sequentially modify lysyl residues in specific positions to hydroxylysyl, galactosylhydroxylysyl and glucosylgalactosyl hydroxylysyl residues at specific positions. A single human enzyme, Lysyl hydroxylase 3 (LH3), as set forth in Genbank No. 060568, can catalyze all three consecutive modifying steps as seen in hydroxylysine-linked carbohydrate formation.

Thus, the genetically modified cells of the present invention may also express mammalian LH3 (optionally fused to vacuole targeting sequences). It will be appreciated that for targeting to the vacuole, the endogenous ER retention sequence is removed prior to expression.

An LH3 encoding sequence such as that set forth by SEQ ID NO: 13, can be used for such purposes.

The procollagen(s) and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (which is also termed herein as an expression construct) can be configured for expression throughout the whole organism (e.g. plant, defined tissues or defined cells), and/or at defined developmental stages of the organism. Such a construct may also include selection markers (e.g. antibiotic resistance), enhancer elements and an origin of replication for bacterial replication.

There are various methods for introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct, in which case these sequences are not inherited by the plant's progeny.

In addition, several methods exist in which a nucleic acid construct can be directly introduced into the DNA of a DNA-containing organelle such as a chloroplast.

There are two principle methods of effecting stable genomic integration of exogenous sequences, such as those included within the nucleic acid constructs of the present invention, into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Regardless of the transformation technique employed, once collagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies the plant's potential for correct processing and assembly of the foreign protein.

Following cultivation of such plants, the telopeptide-comprising collagen is typically harvested. Plant tissues/cells are preferably harvested at maturity, and the procollagen molecules are isolated using extraction approaches. Preferably, the harvesting is effected such that the procollagen remains in a state that it can be cleaved by protease enzymes. According to one embodiment, a crude extract is generated from the transgenic plants of the present invention and subsequently contacted with the protease enzymes.

As mentioned, the propeptide or telopeptide-comprising collagen may be incubated with a protease to generate atelocollagen or collagen prior to solubilization. It will be appreciated that the propeptide or telopeptide-comprising collagen may be purified from the genetically engineered cells prior to incubation with protease, or alternatively may be purified following incubation with the protease. Still alternatively, the propeptide or telopeptide-comprising collagen may be partially purified prior to protease treatment and then fully purified following protease treatment. Yet alternatively, the propeptide or telopeptide-comprising collagen may be treated with protease concomitant with other extraction/purification procedures.

Exemplary methods of purifying or semi-purifying the telopeptide-comprising collagen of the present invention include, but are not limited to salting out with ammonium sulfate or the like and/or removal of small molecules by ultrafiltration.

According to one embodiment, the protease used for cleaving the recombinant propeptide or telopeptide comprising collagen is not derived from an animal. Exemplary proteases include, but are not limited to certain plant derived proteases e.g. ficin (EC 3.4.22.3) and certain bacterial derived proteases e.g. subtilisin (EC 3.4.21.62), neutrase. The present inventors also contemplate the use of recombinant enzymes such as rhTrypsin and rhPepsin. Several such enzymes are commercially available e.g. Ficin from Fig tree latex (Sigma, catalog #F4125 and Europe Biochem), Subtilisin from *Bacillus licheniformis* (Sigma, catalog #P5459) Neutrase from bacterium *Bacillus amyloliquefaciens* (Novozymes, catalog #PW201041) and TrypZean™, a recombinant human trypsin expressed in corn (Sigma catalog #T3449).

In some of any of the embodiments described herein, the recombinant human collagen is a recombinant human type 1 collagen.

In some of any of the embodiments described herein, the recombinant human collagen is a plant-derived recombinant human collagen and in some embodiments the plant is tobacco.

In some of any of the embodiments described herein, the recombinant human collagen is a recombinant human type I collagen comprising two α1 units having the amino acid sequence which is at least 90% homologous, at least 91% homologous, 92% homologous, at least 93% homologous, at least 94% homologous, at least 95% homologous, at least 96% homologous, at least 97% homologous, at least 98% homologous, at least 99% homologous or 100% homologous to the sequence as set forth in SEQ ID NO:15 as determined using BlastP software of the National Center of Biotechnology Information (NCBI) using default parameters), and one α2 unit having the amino acid sequence which is at least 90% homologous, at least 91% homologous, 92% homologous, at least 93% homologous, at least 94% homologous, at least 95% homologous, at least 96% homologous, at least 97% homologous, at least 98% homologous, at least 99% homologous or 100% homologous to the sequence as set forth in SEQ ID NO:6. According to a particular embodiment, the type I collagen consists of two α1 units which consists of the sequence as set forth in SEQ ID NO: 15 and one α2 unit consisting of the sequence as set forth in SEQ ID NO:6, as determined using BlastP software of the National Center of Biotechnology Information (NCBI) using default parameters).

In some of any of the embodiments described herein, the α1 unit is encoded by a polynucleotide sequence being at least which is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence as set forth in SEQ ID NO: 16. The α2 unit is encoded by a polynucleotide sequence being at least which is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence as set forth in SEQ ID NO: 10.

Identity (e.g., percent homology) can be determined using any homology comparison software, including for example, the BlastN software of the National Center of Biotechnology Information (NCBI) such as by using default parameters.

In some of any of the embodiments described herein, the human recombinant collagen (rhCollagen) as described herein in any of the respective embodiments is a monomeric rhCollagen.

By "monomeric" it is meant a rhCollagen as described herein which is soluble in an aqueous solution and does not form fibrillar aggregates.

In some of any of the embodiments described herein, the human recombinant collagen (rhCollagen) as described herein in any of the respective embodiments is a fibrillar rhCollagen.

By "fibrillar" it is meant a rhCollagen as described herein which is in a form of fibrillar aggregates in an aqueous solution containing same. Typically, but not obligatory, fibrillar rhCollagen is formed by subjecting monomeric rhCollagen to a fibrillogenesis buffer, typically featuring a basic pH. An exemplary procedure for forming fibrillar rhCollagen, is described in the Examples section that follows.

Curable Collagen:

According to an aspect of some embodiments of the present invention there is provided a composition that comprises a curable collagen. According to some embodiments, the composition is usable in additive manufacturing of a 3D object as described herein (e.g., in bioprinting). According to some embodiments, the composition is usable, or is for use, in the preparation of a modeling material formulation for an additive manufacturing process (e.g., bioprinting).

By "curable" it is meant herein a material that is capable of undergoing curing, or hardening, as defined herein, when exposed to a suitable curing condition.

A curable material is typically hardened or cured by undergoing polymerization and/or cross-linking.

Curable materials are typically polymerizable materials, which undergo polymerization and/or cross-linking when exposed to a suitable curing condition or a suitable curing energy (a suitable energy source). Alternatively, curable materials are thermo-responsive materials, which solidify or harden upon exposure to a temperature change (e.g., heating or cooling). Optionally, curable materials are made of small particles (e.g., nanoparticles or nanoclays) which can undergo curing to form a hardened material. Further optionally, curable materials are biological materials which undergo a reaction to form a hardened or solid material upon a biological reaction (e.g., an enzymatically-catalyzed reaction).

In some of any of the embodiments described herein, a curable material is a photopolymerizable material, which polymerizes and/or undergoes cross-linking upon exposure to radiation, as described herein, and in some embodiments the curable material is a UV-curable material, which polymerizes or undergoes cross-linking upon exposure to UV-vis radiation, as described herein.

In some of any of the embodiments described herein, when a curable material is exposed to a curing condition (e.g., radiation, reagent), it polymerizes by any one, or combination, of chain elongation, entanglement and cross-linking. The cross-linking can be chemical and/or physical.

In some of any of the embodiments described herein, a curable material can be a mono-functional curable material or a multi-functional curable material.

Herein, a mono-functional curable material comprises one curable group—a functional group that can undergo polymerization, entanglement and/or cross-linking when exposed to a curing condition (e.g., radiation, presence of calcium ions).

A multi-functional curable material comprises two or more, e.g., 2, 3, 4 or more, curable groups. Multi-functional curable materials can be, for example, di-functional, tri-functional or tetra-functional curable materials, which comprise 2, 3 or 4 curable groups, respectively.

By "curable collagen" it is meant a collagen as described herein in any of the respective embodiments (human recombinant collagen), which features one or more curable groups as defined herein. According to some of any of the embodiments described herein, the curable collagen is a multi-functional curable material that comprises a plurality of curable groups, as defined herein.

The terms "curable collagen", "curable rhCollagen" and "rhCollagen featuring one or more (or at least one) curable groups" are used herein interchangeably.

According to some of any of the embodiments described herein, the curable collagen comprises an amino acid sequence as described herein in any of the respective embodiments, and features one or more, preferably a plurality of, curable groups generated at at least a portion of the amino acid residues forming the collagen, preferably by covalent attachment of a compound that comprises a curable group to functional groups of the side chains of the amino acid residues. Alternatively, or in addition, curable groups can be generated at the N-terminus and/or C-terminus of one or more the units forming the collagen, for example, by covalent attachment of compound that comprises a curable group to a respective amine or carboxylate.

According to some of any of the embodiments described herein, at least a portion of the curable groups in a curable collagen as described herein are cross-linkable groups, which undergo cross-linking when exposed to a curing condition.

In some embodiments, curable groups can undergo polymerization and/or cross-linking via free-radical mechanism.

Exemplary such curable groups include acrylic groups, including acrylate, methacrylate, acrylamide and methacrylamide groups. Other free-radical curable groups may include thiols, vinyl ethers and other groups that feature a reactive double bond.

In some embodiments, curable groups can undergo polymerization and/or cross-linking via other mechanisms, such as cationic polymerization, or (cationic or anionic) ring opening polymerization. Exemplary such curable groups include, but are not limited to, epoxy-containing groups, caprolactam, caprolactone, oxetane, and vinyl ether.

Other curable groups can include, for example, formation of amide bonds between functional carboxylate and amine group (each being a curable group that reacts with the other and can effect cross-linking); formation of urethane between isocyanate groups and hydroxyl groups via polycondensation in the presence of a catalyst and/or upon exposure to UV radiation; and formation of disulfide bonds between two thiols.

Any other curable groups are contemplated.

The curable groups in the curable collagen can be generated by means of chemical reactions between a material that comprises or can generate the curable group(s) when reacted with chemically-compatible functional groups present in the collagen, as described herein, either directly, or be means of a spacer or a linker, using chemistries well known in the art. For example, a material that comprises a curable group and a functional group can be reacted with a compatible functional group in the collagen, for example, a functional group in an amino acid side chain, such that the curable group is a substituent of the amino acid side chain.

In some embodiments, a compatible functional group is first generated within the collagen by chemical modification of chemical groups of the collagen, and is that reacted with a material that comprises or generates a curable group upon the reaction.

Whenever a curable collagen comprises more than one curable group, the curable groups can be the same of different.

According to some of any of the embodiments described herein, at least a portion, or all, of the curable groups in a curable collagen of the present embodiments are photopolymerizable groups (e.g., UV-curable groups) that are capable of undergoing polymerization and/or cross-linking upon exposure to irradiation as described herein.

According to some of any of the embodiments described herein there the curable group is a photocurable or photopolymerizable group (e.g., an acrylate or methacrylate).

Alternatively, or in addition, the curable group is a thiol-containing group, which provides disulfide bridge upon curing.

Alternatively, or in addition, the curable group or moiety is cured upon undergoing a chemical reaction, such as glycation of conjugation (using coupling agents such as EDC).

According to some embodiments, the curable groups comprise an amine and a carboxyl group which form peptide bonds upon curing.

According to some of any of the embodiments described herein, at least a portion, or all, of the curable groups in a curable collagen of the present embodiments are acrylic groups, as defined herein.

According to some of any of the embodiments described herein, an acrylic group such as metharylamide can be generated by reacting an acrylate or methacrylate (e.g., acrylic acid, methacrylic acid, acrylic or methacrylic ester, acrylic or methacrylic anhydride) with an amine functional group (of, for example, lysine residues).

According to some of any of the embodiments of the present invention, the number of the curable groups in a curable collagen as described herein can determine the degree of curing (e.g., the degree of cross-linking) and can be manipulated in order to achieve a desired curing (e.g., cross-linking) degree.

According to some of any of the embodiments described herein, the curable collagen features a plurality of acrylamide or methacrylamide curable groups generated by reacting with lysine residues as described herein.

According to some of any of the embodiments described herein, the curable collagen features a plurality of acrylamide or methacrylamide curable groups substituting the amine groups of lysine residues in the collagen.

In some embodiments, at least 50%, or at least 60%, or at least 70%, of the lysine residues in the collagen are substituted by a methacrylamide or acrylamide group. In some embodiments, the curable collagen features from 70% to 100%, or from 80% to 100%, or from 90% to 100%, of its lysine residues substituted by a methacrylamide or acrylamide group, including any intermediate values and subranges therebetween.

According to an aspect of some embodiments of the present invention there is provided a process of preparing a curable rhCollagen as described herein. The process is effected, in some embodiments, by reacting a material that comprises a curable group or which generates a curable group with the rhCollagen, in accordance with the embodiments described herein.

The number of curable groups in the rhCollagen can be controlled by manipulating the amount of the material reacted with the rhCollagen for generating the curable groups.

In some embodiments, the material is used in a molar excess with respect to the respective functional groups that are reacted therewith, for example, in a mol ratio of 2:1, 5:1, 10:1, 15:1, 20:1 30:1, 50:1, or, for example, from 1.1:1 to 50:1, including any intermediate values and subranges therebetween, with respect to the chemically compatible functional groups in the rhCollagen (e.g., the amino acid residues featuring such functional groups), or with respect to the rhCollagen.

According to some of any of the embodiments described herein, the curable collagen is a recombinant human type I collagen as described herein in any of the respective embodiments and any combination thereof.

Modeling Material Formulation(s):

According to the present embodiments described herein, in at least one of the layers formed during the AM (bioprinting process), the dispensed modeling material formulation comprises a biological component or material as described herein and is regarded as bio-ink, as described herein.

According to the present embodiments, the building material comprises at least one modeling material formulation that comprises a curable recombinant human collagen, as described herein in any of the respective embodiments. Such a modeling material formulation is also referred to herein as rhCollagen-containing formulation.

According to some of any of the embodiments described herein, the rhCollagen-containing formulation further comprises a carrier, and in some of these embodiments, the carrier is an aqueous carrier.

The aqueous carrier can be water, a buffer featuring pH in a range of from about 4 to about 10, or from about 6 to about 8, or from about 7 to about 7.4, a basic aqueous solution or an acidic aqueous solution.

The aqueous carrier can comprise salts and other water-soluble materials at varying concentrations. In some embodiments, a concentration of a salt in the carrier ranges from about 0.1 mM to about 0.2 M, or from about 0.1 mM to about 0.1 M, or from about 0.1 mM to about 100 mM, or from about 0.1 mM to about 50 mM, or from about 0.1 mM to about 20 mM, including an intermediate values and subranges therebetween.

In some embodiments, the aqueous carrier comprises salts at physiologically acceptable concentrations, such that the formulation features osmolarity around a physiological osmolarity.

In some embodiments the aqueous carrier comprises a phosphate salt, for example, a sodium phosphate monobasic ($NaH_2PO_4$) and/or a sodium phosphate dibasic (sodium hydrogen phosphate; $Na_2HPO_4$). In some embodiments, the total concentration of the phosphate salt(s) is about 0.1 M.

In some embodiments, the aqueous carrier comprises NaCl or any other physiologically acceptable salt.

In some embodiments, the aqueous carrier comprises a phosphate buffer and in some embodiments, the aqueous carrier comprises a phosphate buffer saline, which comprises sodium phosphate monobasic and/or sodium phosphate dibasic and NaCl.

The phosphate buffer saline (PBS) can be a commercially available PBS (e.g., DPBS) or a custom-made buffer featuring a desirable pH and/or osmolarity.

In exemplary embodiments, the aqueous carrier comprises a phosphate buffer that comprises a phosphate sodium salt as described herein at a concentration of about 0.1M and NaCl at a concentration of from about 0 mM to about 200 mM, including any intermediate value and subranges therebetween.

Any other buffers are also usable in the context of the present embodiments.

In some of any of the embodiments described herein, the aqueous carrier comprises an acid.

In some embodiments, a concentration of the acid is lower than 100 mM, and can be, for example, of from 0.1 mM to 50 mM, or from 0.1 mM to 30 mM, or from 0.1 mM to 40 mM, or from 0.1 mM to 30 mM, or from 1 to 30 mM, or from 10 to 30 Mm, including any intermediate values and subranges therebetween.

The acid can be an inorganic acid (e.g., HCl) or an organic acid, preferably which is water soluble at the above-indicated concentrations (e.g., acetic acid).

In some of any of the embodiments described herein, the aqueous carrier comprises a culturing medium. The culturing medium can be a commercially available culturing medium or a custom-made culturing medium. The culture medium can be any liquid medium which allows at least cell survival. Such a culture medium can include, for example, salts, sugars, amino acids and minerals in the appropriate concentrations and with various additives and those of skills in the art are capable of determining a suitable culture medium to specific cell types. Non-limiting examples of such culture medium include, phosphate buffered saline, DMEM, MEM, RPMI 1640, McCoy's 5A medium, medium 199 and IMDM (available e.g., from Biological Industries, Beth Ha'emek, Israel; Gibco-Invitrogen Corporation products, Grand Island, NY, USA).

The culture medium may be supplemented with various antibiotics (e.g., Penicillin and Streptomycin), growth factors or hormones, specific amino acids (e.g., L-glutamin) cytokines and the like.

In some of any of the embodiments described herein, a concentration of the curable recombinant human collagen in the modeling material formulation containing same ranges from 0.5 mg/mL to 50 mg/mL, or from 0.5 mg/mL to 20 mg/mL, or from 1 mg/mL to 50 mg/mL, or from 1 mg/mL to 50 mg/mL, or from 1 mg/mL to 40 mg/mL, or from 1 mg/mL to 30 mg/mL, or from 2 mg/mL to 20 mg/mL, or from 5 mg/mL to 15 mg/mL, including any intermediate values and subranges therebetween.

A concentration of the curable rhCollagen in a modeling material formulation containing same can affect the rheological properties of the formulation and of the hardened formulation obtained upon dispensing, and can be manipulated in accordance with AM methodology and conditions employed and desired properties of the final object or a portion thereof.

According to some of any of the embodiments described herein, the modeling material formulation features a shear-thinning behavior and is a shear-thinning formulation.

According to some of any of the embodiments described herein, the modeling material formulation features a thermal-thinning behavior and a thermal-thinning formulation.

The term "shear-thinning" describes a property of a fluidic material that is reflected by a decrease in its viscosity (increase in its fluidity) upon application of shear forces (under shear strain). In some of the present embodiments, a shear-thinning material is such that exhibits a significant, e.g., at least 100%, reduction in its shear modulus upon increasing the shear strain from about 1% to above 50%. Shear-thinning materials therefore exhibit a shear-dependent viscosity profile.

The term "thermal-thinning" describes a property of a fluidic material that is reflected by a decrease in its viscosity (increase in its fluidity) upon application of heat energy (increase in temperature). In some of the present embodiments, thermal-thinning materials feature a decrease in viscosity by at least 10% upon a temperature increase of 5° C. Thermal-thinning materials therefore exhibit a temperature-dependent viscosity profile.

According to some of any of the embodiments described herein, the rhColagen-containing formulation is both shear-thinning and thermal-thinning formulation, as defined herein.

According to some of any of the embodiments described herein, the modeling material formulation features a viscosity of no more than 2,000 centipoises, or no more than 1,500 centipoises, at a zero shear rate, at 37° C., when determined using a rheometer as described in the Examples section that follows.

According to some of any of the embodiments described herein, the modeling material formulation features a viscosity of no more than 2000 centipoises, or no more than 1,500 centipoises, at a shear rate of 5 1/sec, at room temperature, when determined using a rheometer as described in the Examples section that follows.

According to some of any of the embodiments described herein, the modeling material formulation features the above-indicated viscosity values when a concentration of the curable collagen is at least 3 mg/mL, or at least 5 mg/mL, for example, is 10 mg/mL.

According to some of any of the embodiments described herein, the modeling material formulation features a viscosity profile at 37° C. which is similar to its viscosity profile at 4° C.

According to some of any of the embodiments described herein, the modeling material formulation features a viscosity at 37° C. which is lower by at least 10%, or at least 20%, than its viscosity at 4° C., when measured at a shear rate of from 1 to 10 [1/sec], for the same concentration of the curable rhCollagen.

According to some of any of the embodiments described herein, the modeling material formulation features, when hardened, storage modulus (G') of at least 1,000 Pa.

According to some of any of the embodiments described herein, the modeling material features, when hardened (e.g., when exposed a curing condition as described herein in any of the respective embodiments), an increase of at least 10-folds of its storage modulus (G').

According to some of any of the embodiments described herein, the modeling material formulation provides, when hardened, a hydrogel material, formed upon cross-linking of the rhCollagen within the aqueous carrier.

Herein and in the art, the term "hydrogel" describes a three-dimensional fibrous network containing at least 20%, typically at least 50%, or at least 80%, and up to about 99.99% (by mass) water. A hydrogel can be regarded as a material which is mostly water, yet behaves like a solid or semi-solid due to a three-dimensional crosslinked solid-like network, made of polymeric chains (e.g., collagen chains), within the liquid dispersing medium. The polymeric chains are inter-connected (crosslinked) by chemical bonds (covalent, hydrogen and ionic/complex/metallic bonds, typically covalent bonds).

Herein throughout, whenever polymeric chains or a polymeric material is described, it encompasses polymeric biological materials (e.g., macromolecules) such as peptides, proteins, oligonucleotides and nucleic acids.

Hydrogels may take a physical form that ranges from soft, brittle and weak to hard, elastic and tough material. Soft hydrogels may be characterized by rheological parameters including elastic and viscoelastic parameters, while hard hydrogels are suitably characterized by tensile strength parameters, elastic, storage and loss moduli, as these terms are known in the art.

The softness/hardness of a hydrogel is governed inter alia by the chemical composition of the polymer chains, the "degree of cross-linking" (number of interconnected links between the chains), the aqueous media content and composition, and temperature.

A hydrogel, according to some embodiments of the present invention, may contain macromolecular polymeric and/or fibrous elements which are not chemically connected to the main crosslinked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes. Alternatively, or in addition, such macromolecules are chemically connected to the main crosslinked network of the hydrogel, for example, by acting as a cross-linking agent, or by otherwise forming a part of the three-dimensional network of the hydrogel.

In some embodiments, the hydrogel is porous and in some embodiments, at least a portion of the pores in the hydrogel are nanopores, having an average volume at the nanoscale range.

According to some of any of the embodiments described herein, the rhCollagen-containing modeling material formulation further comprises one or more additional materials, including, for example, one or more additional curable materials, one or more non-curable materials and/or one or more biological components or materials.

According to some of any of the embodiments described herein, the printing media (the building material) comprises one or more additional materials, including, for example, one or more additional curable materials, one or more non-curable materials and/or one or more biological components.

According to some of any of the embodiments described herein, the additional materials are included in the rhCollagen-containing formulation or in one or more other modeling material formulations.

Additional curable materials that can be included in the rhCollagen formulation or in one or more other modeling material formulations can be any curable material as defined herein, and is preferably a biocompatible material.

In some embodiments the additional curable material is or comprises a hydrogel, as defined herein, which can form a hardened modeling material, typically upon further cross-linking and/or co-polymerization, when exposed to a curing condition at which the cross-linking and/or co-polymerization reaction occurs. Such curable materials are also referred to herein as hydrogel curable materials.

In some of any of the embodiments described herein, a curable material is or comprises a hydrogel forming material, as defined herein, which can form a hydrogel as a hardened modeling material, typically upon cross-linking, entanglement, polymerization and/or co-polymerization, when exposed to a curing condition at which the cross-linking, polymerization and/or co-polymerization, and/or entanglement reaction occurs. Such curable materials are also referred to herein as hydrogel-forming curable materials or as gel-forming materials.

The hydrogel, according to embodiments of the present invention, can be of biological origin or synthetically prepared.

According to some embodiments of the present invention, the hydrogel is biocompatible, and is such that when a biological moiety is impregnated or accumulated therein, an activity of the biological moiety is maintained, that is, a change in an activity of the biological moiety is no more than 30%, or no more than 20%, or no more than 10%, compared to an activity of the biological moiety in a physiological medium.

Exemplary polymers or co-polymers usable for forming a hydrogel according to the present embodiments include polyacrylates, polymethacrylates, polyacrylamides, polymethacrylamides, polyvinylpyrrolidone and copolymers of any of the foregoing. Other examples include polyethers, polyurethanes, and poly(ethylene glycol), functionalized by cross-linking groups or usable in combination with compatible cross linking agents.

Some specific, non-limiting examples, include: poly(2-vinylpyridine), poly(acrylic acid), poly(methacrylic acid), poly(N-isopropylacrylamide), poly(N,N'-methylenbisacrylamide), poly(N—(N-propyl)acrylamide), poly(methacyclic acid), poly(2-hydroxyacrylamide), poly (ethylene glycol) acrylate, poly (ethylene glycol) methacrylate, and polysaccharides such as hyaluronic acid, dextran, alginate, agarose, and the like, and any co-polymer of the foregoing.

Hydrogel precursors (hydrogel-forming materials) forming such polymeric chains are contemplated, including any combination thereof.

Hydrogels are typically formed of, or are formed in the presence of, di- or tri- or multi-functional monomers, oligomer or polymers, which are collectively referred to as hydrogel precursors or hydrogel-forming agents or hydrogen-forming materials, having two, three or more polymerizable groups. The presence of more than one polymerizable group renders such precursors cross-linkable, and allow the formation of the three-dimensional network.

Exemplary cross-linkable monomers include, without limitation, the family of di- and triacrylates monomers, which have two or three polymerizable functionalities, one of which can be regarded as a cross-linkable functional group. Exemplary diacrylates monomers include, without limitation, methylene diacrylate, and the family of poly (ethylene glycol)$_n$ dimethacrylate (nEGDMA). Exemplary triacrylates monomers include, without limitation, trimethylolpropane triacrylate, pentaerythritol triacrylate, tris (2-hydroxy ethyl) isocyanurate triacrylate, isocyanuric acid tris(2-acryloyloxyethyl) ester, ethoxylated trimethylolpropane triacrylate, pentaerythrityl triacrylate and glycerol triacrylate, phosphinylidynetris(oxyethylene) triacrylate.

In some of any of the embodiments described herein, a curable material, whether monomeric or oligomeric, can be a mono-functional curable material or a multi-functional curable material.

Exemplary polymers or co-polymers usable for forming a hydrogel according to the present embodiments include polyacrylates, polymethacrylates, polyacrylamides, polymethacrylamides, polyvinylpyrrolidone and copolymers of any of the foregoing. Other examples include polyethers, polyurethanes, and poly(ethylene glycol), functionalized by cross-linking groups or usable in combination with compatible cross linking agents.

Some specific, non-limiting examples, include: poly(2-vinylpiridine), poly(acrylic acid), poly(methacrylic acid), poly(N-isopropylacrylamide), poly(N,N'-methylenbisacrylamide), poly(N—(N-propyl)acrylamide), poly(methacyclic acid), poly(2-hydroxyacrylamide), poly (ethylene glycol) acrylate, poly (ethylene glycol) methacrylate, and polysaccharides such as dextran, alginate, agarose, and the like, and any co-polymer of the foregoing.

Hydrogel precursors (hydrogel-forming materials) forming such polymeric chains are contemplated, including any combination thereof.

Curable materials usable in the field of bioprinting are predominantly based on either naturally derived materials, including, for example, Matrigel, Alginate, Pectin, Xanthan gum, Gelatin, Chitosan, Fibrin, Cellulose and Hyaluronic acid, which can be isolated from animal or human tissues, or recombinantly-generated, or synthetically-prepared materials, including, for example, polyethyleneglycol; PEG, gelatin methacrylate; GelMA, poly(propylene oxide); PPO, poly (ethylene oxide); PEO; PEG, polyethyleneglycol-diacrylate, polyglutamic acid, gelatin methacrylate; GelMA, PLGA/PLLA, poly(dimethyl siloxane); Nanocellulose; Pluronic F127, short di-peptides (FF), Fmoc-peptide-based hydrogels such as Fmoc-FF—OH, Fmoc-FRGD-OH, Fmoc-RGDF-OH, Fmoc-2-Nal-OH, Fmoc-FG-OH, and thermoplastic polymers such as Polycaprolactone (PCL), Polylactic acid (PLA) or Poly(D,L-lactide-co-glycolide).

Exemplary curable materials usable in the context of the present embodiments include, but are not limited to, Matrigel, Gelatin methacrylate (GelMA), Nanocellulose (nano-scaled structured materials which are UV-curable, including cellulose nanocrystals (CNC), cellulose nanofibrils (CNF), and bacterial cellulose (BC), also referred to as microbial cellulose), Pluronic® materials, including, for example, Pluronic F127 which is fluid at a low temperature forms a gel at a high temperature, above critical micellar concentration (CMC) and Pluronic F127-diacrylate (DA) which is UV-curable, Hyaluronic acid (HA), Acrylated hyaluronic acid (AHA), methacrylated hyaluronic acid (MAHA), Poly-(ethylene glycol) diacrylate (PEGDA), Alginate, Xanthan gum, Pectin, Chitosan which can be crosslinked with a chemical agent such as Glutaraldehyde, Genipin or Sodium Tripolyphosphate (TPP).

Exemplary curable materials are described in the Examples section that follows.

Biological components or materials that can be included in one or more modeling material formulations as described herein include, cellular components, including, for example, culturing cells, and other cellular components such as cytokines, chemokines, growth factors; as well as other biological components such as proteins, agents that act to increase cell attachment, cell spreading, cell proliferation, cell differentiation and/or cell migration; an amino acid, peptides, polypeptides, proteins, DNA, RNA, lipids and/or proteoglycans.

Cells may comprise a heterogeneous population of cells or alternatively the cells may comprise a homogeneous population of cells. Such cells can be for example stem cells (such as embryonic stem cells, bone marrow stem cells, cord blood cells, mesenchymal stem cells, adult tissue stem cells), progenitor cells, or differentiated cells such as chondrocytes, osteoblasts, connective tissue cells (e.g., fibrocytes, fibroblasts and adipose cells), endothelial and epithelial cells. The cells may be naïve or genetically modified.

According to one embodiment of this aspect of the present invention, the cells are mammalian in origin.

Furthermore, the cells may be of autologous origin or non-autologous origin, such as postpartum-derived cells (as described in U.S. application Ser. Nos. 10/887,012 and 10/887,446). Typically the cells are selected according to the desired application.

Suitable proteins which can be used include, but are not limited to, extracellular matrix proteins [e.g., fibrinogen, collagen, fibronectin, vimentin, microtubule-associated protein 1D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-α, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-β, platelet-derived growth factor, Vascular Endothelial Growth Factor and angiopeptin], cytokines [e.g., M-CSF, IL-1beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

In addition, calcium phosphate materials, such as hydroxyapatite, for example, in a form of particles, can be used, including, but not limited to, nanoHA and nanoTCP. The particles size should be compatible with the dispensing heads so as to avoid clogging.

Non-curable materials, other than the biological materials as described herein, that can be included in one or more modeling formulations as described herein can be materials that impart a certain property to the formulation or to the hardened formulation and to the part of the object formed thereby. Such a property can be a physical property (e.g., an optical property such as transparency or opacity, color, a spectral property, heat resistance, electrical property and the like), or a mechanical or rheological property such as viscosity, elasticity, storage modulus, loss modulus, stiffness, hardness, and the like. Alternatively, or in addition, non-curable materials can be such that provide a biological function, for example, therapeutically active agents.

Exemplary non-curable materials include thixotropic agents, reinforcing agents, toughening agents, fillers, colorants, pigments, etc.

An exemplary non-curable material includes titanium dioxide.

An exemplary non-curable material includes oxidized cellulose.

According to some of any of the embodiments described herein, one or more of the modeling material formulations comprises hyaluronic acid.

According to some of any of the embodiments described herein, one or more of the modeling material formulations comprises hyaluronic acid featuring a curable group as defined herein.

According to some of any of the embodiments described herein, one or more of the modeling material formulations comprises one or more biological components or materials such as, but not limited to, cells, growth factors, peptides, heparan sulfate and fibronectin.

According to some of any of the embodiments described herein, one or more of the modeling material formulations comprises one or more agents that modify a mechanical property of the formulation and/or the object, as described herein, such as, but not limited to, alginate, hyaluronic acid, fibrinogen, elastin, peptides and a thixotropic agent (e.g., Crystalline nano cellulose (CNC)), oxidized cellulose, titanium dioxide, Clay mineral and carbon nanotubes.

In some of any of the embodiments described herein the rhCollagen-containing formulation further comprises one or more additional curable materials as described herein in any of the respective embodiments.

In some of these embodiments, a weight ratio of the curable recombinant human collagen and the additional curable material ranges from 10:1 to 1:2, or from 10:1 to 1:1, or from 5:1 to 2:1, including any intermediate value and subranges therebetween.

In some of any of the embodiments described herein the rhCollagen-containing formulation further comprises a thixotropic agent, as defined herein.

Herein throughout, the term "thixotropic" describes a property of a fluidic compound or material that is reflected by a time-dependent shear-thinning, that is its viscosity is decreased in correlation with the time at which shear forces are applied, and returns back to its original value when application of shear forces is ceased. In some of the present embodiments, a thixotropic material or agent is such that exhibits or imparts a significant, e.g., at least 100%, reduction in shear modulus under 50% strain.

In some of any of the embodiments described herein the rhCollagen-containing formulation further comprises a gel-forming agent, for example, a hydrogel-forming agent as described herein.

In some of any of the embodiments described herein the rhCollagen-containing formulation further comprises a biological component or material as described herein.

In some of any of the embodiments described herein the rhCollagen-containing formulation further comprises one or more curable or non-curable materials as described herein in any of the respective embodiments.

According to some of any of the embodiments described herein the recombinant human collagen is selected from a monomeric collagen and a fibrillar collagen, as exemplified in the Examples section that follows.

According to some of any of the embodiments described herein, the mol ratio of the curable group(s) and the collagen is essentially as exemplified in the Examples section herein.

According to some of any of the embodiments described herein the formulation further comprises hyaluronic acid, as described herein.

According to some of any of the embodiments described herein the formulation further comprises hyaluronic acid featuring a polymerizable group.

According to some of any of the embodiments described herein the formulation further comprises one or more biological components such as, but not limited to, a component selected from cells, growth factors, peptides, heparan sulfate and fibronectin.

According to some of any of the embodiments described herein the formulation further comprises one or more agents that modify a mechanical property of the formulation and/or the object, such as, but not limited to, alginate, hyaluronic acid, fibrinogen, elastin, peptides and a thixotropic agent (e.g., Crystalline nano cellulose (CNC)).

According to some of any of the embodiments described herein the formulation features a neutral pH (e.g., from about 6 to about 8).

According to some of any of the embodiments described herein the formulation features viscosity parameters essentially as described herein.

According to some of any of the embodiments described herein the formulation features approximately the same viscosity at 4° C. and at a temperature above 10, or above 20° C. (e.g., 37° C.).

In embodiments where two or more modeling material formulations are used, two of more formulations are rh-Collagen containing formulations as described herein, which differ from one another by the presence, type and/or concentration of an additional material that is included therein. For example, one formulation can comprise curable rhCollagen, and another formulation can comprise curable rhCollagen and a biological material as described herein. For example, one formulation can comprise curable rhCollagen, and another formulation can comprise curable rhCollagen and an additional curable material as described herein. For example, one formulation can comprise curable rhCollagen and one additional curable material, and another formulation can comprise curable rhCollagen and another additional curable material as described herein. For example, one formulation can comprise curable rhCollagen and one additional curable material, and another formulation can comprise curable rhCollagen and a non-curable material as described herein. Any other combinations are contemplated.

In some of any of the embodiments described herein, all the curable materials in the building material are cured under the same curing condition. In some embodiments, all curable materials are photocurable.

In some of any of the embodiments described herein, a modeling material formulation that comprises a curable material further comprises an agent that promotes curing or hardening of the curable material when exposed to a curing condition.

The concentration of the agent can be determined in accordance with the concentration of the curable material and the desired degree of curing (e.g., desired cross-linking degree).

When the curable materials are photocurable materials, the agent is a photoinitiator. The photoinitiator is selected in accordance with the curing mechanism (e.g., free-radical, cationic, etc.).

A free-radical photoinitiator may be any compound that produces a free radical on exposure to radiation such as ultraviolet or visible radiation and thereby initiates a polymerization reaction. Non-limiting examples of suitable photoinitiators include benzophenones (aromatic ketones) such as benzophenone, methyl benzophenone, Michler's ketone and xanthones; acylphosphine oxide type photo-initiators such as 2,4,6-trimethylbenzolydiphenyl phosphine oxide (TMPO), 2,4,6-trimethylbenzoylethoxyphenyl phosphine oxide (TEPO), and bisacylphosphine oxides (BAPO's); benzoins and bezoin alkyl ethers such as benzoin, benzoin methyl ether and benzoin isopropyl ether and the like. Examples of photoinitiators are alpha-amino ketone, and bisacylphosphine oxide (BAPO's).

Exemplary photoinitiators include, but are not limited to, those of the Irgacure® family, riboflavin, rose Bengal, and more.

A free-radical photo-initiator may be used alone or in combination with a co-initiator. Co-initiators are used with initiators that need a second molecule to produce a radical that is active in the photocurable free-radical systems. Benzophenone is an example of a photoinitiator that requires a second molecule, such as an amine, to produce a free radical. After absorbing radiation, benzophenone reacts with a ternary amine by hydrogen abstraction, to generate an alpha-amino radical which initiates polymerization of acrylates. Non-limiting example of a class of co-initiators are alkanolamines such as triethylamine, methyldiethanolamine and triethanolamine.

Suitable cationic photoinitiators include, for example, compounds which form aprotic acids or Bronsted acids upon exposure to ultraviolet and/or visible light sufficient to initiate polymerization. The photoinitiator used may be a single compound, a mixture of two or more active compounds, or a combination of two or more different compounds, i.e. co-initiators. Non-limiting examples of suitable cationic photoinitiators include aryldiazonium salts, diaryliodonium salts, triarylsulphonium salts, triarylselenonium salts and the like. An exemplary cationic photoinitiator is a mixture of triarylsolfonium hexafluoroantimonate salts.

Non-limiting examples of suitable cationic photoinitiators include P-(octyloxyphenyl) phenyliodonium hexafluoroantimonate UVACURE 1600 from Cytec Company (USA), iodonium (4-methylphenyl)(4-(2-methylpropyl)phenyl)-hexafluorophosphate known as Irgacure 250 or Irgacure 270 available from Ciba Speciality Chemicals (Switzerland), mixed arylsulfonium hexafluoroantimonate salts known as UVI 6976 and 6992 available from Lambson Fine Chemicals (England), diaryliodonium hexafluoroantimonate known as PC 2506 available from Polyset Company (USA), (tolylcumyl) iodonium tetrakis (pentafluorophenyl) borate known as Rhodorsil® Photoinitiator 2074 available from Bluestar Silicones (USA), iodonium bis(4-dodecylphenyl)-(OC-6-11)-hexafluoro antimonate known as Tego PC 1466 from Evonik Industries AG (Germany).

The Object:

Herein throughout, in the context of bioprinting, the term "object" describes a final product of the additive manufacturing which comprises, in at least a portion thereof, a biological component. This term refers to the product obtained by a bioprinting method as described herein, after removal of the support material, if such has been used as part of the uncured building material.

The term "object" as used herein throughout refers to a whole object or a part thereof.

In the context of the present embodiments, the object comprises in at least a portion thereof a collagen-based material.

By "collagen-based material" it is meant a material that comprises collagen, preferably a recombinant human collagen as described herein in any of the respective embodiments and any combination thereof.

In some of any of the embodiments described herein, the collagen-based material comprises a scaffold, for example, a hydrogel scaffold, made of a three-dimensional fibrillar network that comprises recombinant human collagen as described herein.

In some of any of the embodiments described herein, the collagen-based material comprises polymerized and/or cross-linked recombinant human collagen, in which a plurality of monomeric and/or fibrillar collagen units are linked to one another to thereby form a three-dimensional network.

The three-dimension network or scaffold can be in a form of, for example, a film, a sponge, a porous structure, a hydrogel, and any other form, according to a desired need.

In some of any of the embodiments described herein, the object is in a form of a tissue or organ, which comprises, in at least a portion thereof, a collagen-based material as described herein. Such an object can be formulated in accordance with a respective 3D printing data of a desired organ or tissue, using, in addition to the curable collagen as described herein, additional curable materials and biological materials as described herein.

In some embodiments, the object is an implantable object. In some embodiments, the object is an artificial skin. In some embodiments, the object is an artificial tissue (e.g., connective tissue, or muscle tissue such as cardiac tissue and pancreatic tissue). Examples of connective tissues include, but are not limited to, cartilage (including, elastic, hyaline, and fibrocartilage), adipose tissue, reticular connective tissue, embryonic connective tissues (including mesenchymal connective tissue and mucous connective tissue), tendons, ligaments, and bone.

In some embodiments, the object is usable in, or is for use in, constructing an artificial organ or tissue.

The object can further comprise hardened materials formed of one or more of the additional curable materials as described herein in any of the respective embodiments, biological components or materials, as described herein in any of the respective embodiments, and/or non-curable materials as described herein in any of the respective embodiments.

In some embodiments, the object is in a form of a collagen scaffold or film, that can be used in research or therapeutic applications, for example, in repairing a damaged tissue, for example, upon seeding culturing cells therein, or in wound healing.

The scaffolds may be administered to subjects in need thereof for the regeneration of tissue such as connective tissue, muscle tissue such as cardiac tissue and pancreatic tissue.

The films can be used to construct biomedical devices such as, for example, collagen membranes for hemodialysis.

According to some embodiments, films or scaffolds can be used in cell cultures.

The phrase "cell culture" or "culture" as used herein refers to the maintenance of cells in an artificial, e.g., an in vitro environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms.

In some embodiments, the films or scaffolds can be used in a wound healing process.

In some embodiments, collagen films provided herein are used to prevent adhesions following tendon injuries, to lengthen levator palpebrae muscles ophthalmic surgery, and to repair transected nerves. Collagen films provided herein may further be used for burn dressings and in healing of bone defects.

The object of the present embodiments comprises a myriad of other uses including, but not limited to, in the treatment of diseases such as interstitial cystitis, scleroderma, and rheumatoid arthritis cosmetic surgery, as a healing aid for burn patients, as a wound-healing agent, as a dermal filler, for spinal fusion procedures, for urethral bulking, in duraplasty procedures, for reconstruction of bone and a wide variety of dental, orthopedic and surgical purposes.

Kits:

According to an aspect of some embodiments of the present invention, there is provided a kit that comprises a curable rhCollagen as described herein in any of the respective embodiments.

According to some embodiments, the kit comprises a composition that comprises curable rhCollagen as described herein in any of the respective embodiments.

According to some embodiments, the composition comprises the curable rhCollagen in a lyophilized form.

According to some embodiments, the composition comprises the curable rhCollagen and an aqueous solution or carrier.

According to some of any of the embodiments described herein, the kit is identified for use, or is usable, as a modeling material formulation for additive manufacturing (e.g., bioprinting) of an object as described herein in any of the respective embodiments.

According to some of any of the embodiments described herein, the kit further comprises an aqueous carrier, as described herein in any of the respective embodiments. In some embodiments, the composition and the aqueous carrier are packaged individually within the kit.

Alternatively, the kit includes instructions to prepare a modeling material formulation as described herein, by mixing the composition with the aqueous carrier.

It is expected that during the life of a patent maturing from this application many relevant curable biocompatible materials, bioprinting media, and/or bioprinting technologies will be developed and the scope of embodiments related to curable biocompatible materials, bioprinting media, and/or bioprinting technologies is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials:

Human recombinant collagen (rhCollagen) type I expressed and isolated from transgenic tobacco plants was produced and supplied by CollPlant Ltd (Israel).

Type I Bovine Collagen (PureCol®) and Bovine-based Methacrylated collagen were purchased from Advanced Biomatrix, USA.

Methacrylic anhydride, glycidyl methacrylate, triethylamine, tetrabutylammonium bromide, 2,4,6-Trinitrobenzenesulfonic acid (TNBS), 2-Hydroxy-4'-(2-hydroxyethoxy)-2-methylpropiophenone (Irgacure 2959), sodium phosphate monobasic anhydrous, HCl 1N, HCl≥37%, sodium bicarbonate, Titanium dioxide ($TiO_2$), Hepes Buffer, Eosin Y, N-Vinylpyrrolidone and NaOH were purchased from Sigma Aldrich Ltd, Israel.

Dulbaco Phosphate buffer saline (DPBS), ×10 DPBS, Foetal Bovine Serum (FBS), DMEM high glucose and penicillin/streptomicin were purchased from Biological Industries Ltd, Israel.

Sodium phosphate dibasic anhydrous was purchased from Canton, India.

Ethanol absolute and acetone were purchased from Bio-Lab Ltd, Israel.

Hyaluronic acid was purchased by Lifecore, USA.

Acetic acid was purchased from JT Baker or Advanced Biometrix.

Oxidized cellulose was received from Synthesia.

PVAMA (polyvinyl alcohol methacrylate) was provided by Prof. Shoseyov.

TEA (triethanolamine) was purchased from J.T. Baker

Nano-hydroxyapatite (nanoHA) and Nano-tricalcium phosphate (nanoTCP) were purchased from Fluidinova.

Buffer Stock Solutions Preparation:

Fibrillogenesis buffer (FB): sodium phosphate dibasic was dissolved in double distilled water (DDW) to a final concentration of 162 mM. The solution was titrated to pH 11.2 with 10N NaOH.

Medium preparation: 50 mL of fetal bovine serum and 5 mL of penicillin/streptomycin (10,000 units/mL and 10 mg/mL respectively) were added under aseptic conditions to 500 mL of DMEM high glucose medium. The medium was gently mixed and kept in fridge.

Phosphate Buffer (0.1 M)/Saline (0.016M) preparation (300 mOs/L): 1M Phosphate buffer was prepared as follows: 31.6 mL of 1M sodium phosphate dibasic were mixed with 68.4 mL of 1M sodium phosphate monobasic. The obtained 1M Phosphate Buffer was diluted to 0.1M by adding DDW (9:1, vol/vol). NaCl was added to a final concentration of 15.8 mM to achieve physiological osmolarity (300 mOs/L).

Phosphate buffer (0.1M; pH 7.4)/Saline (11.3 mM) (physiological osmolarity) preparation: 1M Phosphate buffer was prepared as follows: 77.4 mL of 1M sodium phosphate dibasic were mixed with 22.6 mL of 1M sodium phosphate monobasic. The obtained 1M Phosphate Buffer was diluted to 0.1M by adding DDW (9:1, vol/vol). NaCl was added to a final concentration of 11.3 mM to achieve physiological osmolarity (300 mOs/L).

Washing buffer: HCl was added to the fibrillogenesis buffer to reach a final concentration of 16.2 mM sodium phosphate dibasic and 10 mM HCl. pH was adjusted to 7.2-7.4 with 10N NaOH.

Instrumental Data:

$^1$H-NMR spectra were recorded at 25° C. on a Bruker Avance II spectrometer, operating at a 1 H resonance frequency of 500 MHz, using $D_2O$ as a solvent. The analysis was quantitative NMR using 64 scans for signal-to-noise averaging, and a recycle delay of 8.6 sec. Values provided represent the δ (normalized chemical shift) in ppm.

Viscosity and G'/G" measurements were performed on a HAAKE RheoStress600 rheometer (Thermo Electron Corporation) with a temperature-controlled cell chamber, using a C60/1° Ti or C35/1° Ti cone-plate set ups. Analysis of cross-linked (hardened) discs was performed using PP20 serrated spindle and 20 mm serrated plate set up.

In-situ crosslinked experiments were conducted on TA discovery hybrid temperature controlled rheometer with a UV chamber.

Other measurements were performed as described in the following.

Example 1

Methacrylation of rhCollagen

Fibrillar rhCollagen-methacrylamide and monomeric rhCollagen-methacrylamide were prepared by reaction of lysine and hydroxylysine residues of the collagen with methacrylic anhydride in aqueous medium as described below, and stored at 4° C. light protected until further use.

Fibrillar rhCollagen-Methacrylamide:

3 to 10 mg/mL fibrillar rhCollagen-methacrylamide (rhCollagen-MA) was synthesized either in a 1× washing buffer as described herein, a fibrillogenesis buffer as described herein or DDW, at room temperature (R.T.) or at 12° C.

In an exemplary procedure, fibrillar rhCollagen-MA was synthesized in DDW as follow: monomeric rhCollagen 3-4 mg/mL solution in 10 mM HCl, (Collage™) was mixed with fibrillogenesis buffer at 9:1 v/v ratio and stirred for 1 hour at R.T, receiving fibrils. The solution was centrifuged at 7500 rpm at 4° C. for 30 minutes, and the supernatant was thereafter discarded. The remaining pellet was re-suspended in equal volume of washing buffer and centrifuged at the same conditions. Thereafter, the sediment fibrils were re-suspended in DDW to obtain a 10 mg/mL solution. The concentration was confirmed by percent solid measurements. Methacrylic anhydride was added drop-wise under nitrogen flow at room temperature at 10 to 20 molar ratio with respect to collagen lysines (10-20 fold), and the reaction solution pH was monitored over time and adjusted to pH 7 with 10N NaOH. After 24 hours reaction, the mixture was dialyzed against washing buffer (pH=7) using 100 kDa cutoff dialysis tubing (Spectrum Laboratories Inc, CA, US) for 3 days at 4° C. with at least 6 changes of the dialysate (washing buffer in this case), to remove reaction by-products, and was thereafter lyophilized for 3-4 days.

The extent of modification of rhCollagen was quantified using TNBS (2,4,6-Trinitrobenzenesulfonic acid) colorimetric assay. This assay quantifies the molar content of free, non-reacted ε-amino groups derived from lysine and hydroxyl lysine, and accordingly the degree of functionalization.

The assay was conducted in accordance with a previously described protocol [Sashidhar et al., Journal of Immunological Methods. 1994, 167, 121-127], and based on Habeeb [Habeeb A.F.S.A, Analytical Biochemistry. 1966, 14, 328-336]. Briefly, freshly prepared 0.4 mL of 0.01% (v/v) TNBS was added to 0.4 mL of 0.1-2 mg/mL fibrillar rhCollagen-MA in sodium bicarbonate 4%. After 2 hours reaction at 40° C., 0.2 mL of 1N HCl and 0.4 mL of 10% (v/v) SDS were added. The absorbance was measured at 335 nm in a spectrophotometer in a 1 mL polystyrene cuvette. A control (blank) was prepared with the same procedure except that sodium bicarbonate buffer was added instead of rhCollagen-MA solution. The absorption of 1-2 mg/mL native fibrillar rhCollagen prepared with the same conditions was recorded for calibration.

Table 1 below presents the data obtained for the degree of functionalization for batches obtained upon reacting the fibrillar rhCollagen with 10-folds, 15-folds or 20-folds mol ratio of methacrylic anhydride, as determined by the TNBS assay.

TABLE 1

| MA:Fibrillar rhCollagen mol ratio | Degree of methacrylation [%] |
| --- | --- |
| 10:1 | 98.1 |
| 15:1 | 95.5 |
| 20:1 | 92.9 |

These results demonstrate the high modification of the fibrillar rhCollagen at all MA concentrations, and suggest that adding the methacrylic reagent at a molar ratio of 10:1 may be preferable for receiving maximal functionalization of the fibrillar rhCollagen.

Monomeric rhCollagen-Methacrylamide:

Monomeric rhCollagen-methacrylamide was synthesized while using 200 mM of MOPS, phosphate, or Tris buffer with the addition of 150 mM NaCl.

In an exemplary procedure, 200 mM MOPS and 150 mM NaCl were added to 3-4 mg/mL Collage™ (a solution of Monomeric rhCollagen in 10 mM HCl and the solution was stirred at room temperature until clear solution was obtained. Thereafter, 1 to 20-fold molar ratio excess of methacrylic anhydride was added drop-wise under nitrogen flow at 12° C., and the pH was adjusted over time to pH 7 with 10N NaOH. After 24 hours reaction, the mixture was initially dialyzed against 10 mM HCl/20 mM NaCl (pH=2) with 100 kDa cutoff dialysis hollow fiber cartridge (GE Healthcare), at least 5 changes of the dialysate, followed by dialysis against 10 mM HCl. The material was then lyophilized.

The structural properties of non-modified monomeric rhCollagen and the degree of methacrylation of collagen lysine amines of rhCollagen (also referred to herein as Coll-MA) were analyzed by $^1$H-NMR spectroscopy (500 MHz). Representative spectra are shown in FIG. 1 for Coll-MA synthesized with 10-folds molar excess of methacrylic anhydride. The signals of the methyl function and acrylic protons of the introduced methacrylate are indicated as (b) and (c), respectively; the lysine methylene signals of non-modified rhCollagen as (a).

The spectrum of the non-modified rhCollagen was in high agreement with collagen spectra reported in the literature [R. Ravichandran et. al; *J. Mater. Chem. B,* 2016, 4, 318-326].

The degree of methacrylation can be calculated from the obtained spectrum using a quantitative analysis technique. The signal at $\delta=3$ ppm (a) is ascribed to the lysine methylene groups in Collagen, and was significantly reduced after methacrylation. Compared to non-modified rhCollagen, new signals can be observed at 1.9 ppm (b) and 5.4-5.7 ppm (c) in the spectrum of Coll-MA, which are assigned to the methyl function and the acrylic protons of the introduced methacrylic groups, respectively, confirming a successful attachment of the methacrylate to the collagen.

Example 2

Viscosity Measurements of rh-Collagen and rh-Collagen-MA

Solutions Preparation for Viscosity Measurements

PureCol® and Collage™ in DPBS: 8 ml of monomeric collagen solutions (3 mg/mL in 10 mM HCl), either rhCollagen (Collage™) or bovine collagen (PureCol®) were neutralized by adding 1 mL of DPBS X10. The solution was then brought to pH 7-7.5 by titration with 0.1N NaOH. Double distillated water (DDW) was then added to reach a final volume of 10 mL. Samples were incubated at 37° C. for at least 90 minutes before measurements were performed (either at 37° C. or 4° C.).

Collage™ in fibrillogenesis buffer: 9 ml of monomeric rhCollagen (Collage™) solution (3.79 mg/mL in 10 mM HCl) was neutralized by adding 1 mL of fibrillogenesis buffer. Samples were incubated at 37° C. for at least 90 minutes before measurements were performed (either at 37° C. or 4° C.).

Fibrillar rhCollagen-methacrylamide in DPBS: Lyophilized fibrillar rhCollagen-MA prepared in DDW and dialyzed vs. washing buffer (as described in Example 1 hereinabove, using 10:1 molar ratio of MA:rhCollagen) was dissolved in DPBS to a concentration of 10 mg/mL. Samples were incubated at 37° C. for at least 90 minutes before measurements were performed (either at 37° C. or 4° C.).

Monomeric rhCollagen-methacrylamide in acetic acid: 10 mg/ml rhCollagen-methacrylamide solution in 20 mM Acetic acid was prepared by adding the appropriate medium volume to the lyophilized material and mixing at room temperature until receiving complete dissolution.

Bovine collagen-methacrylate in acetic acid: 10 mg/ml Bovine collagen-methacrylate solution in 20 mM Acetic acid was prepared by adding the appropriate medium volume (Advanced BioMatrix) to the lyophilized material and mixing at room temperature until receiving complete dissolution.

Temperature Dependence of rhCollagen/Bovine Collagen Viscosity:

FIG. 2 presents comparative plots showing the viscosity of rhCollagen (Collage™) and Bovine Collagen (PureCol)

in DPBS expressed as a function of shear rate at T=4° C. and T=37° C. Bovine collagen (solid lines) shows clear temperature dependence of the zero shear rate viscosity ($\eta_0$), i.e., the viscosity plateau at low shear rate values, having at 37° C. $\eta_0$ values that are more than one order of magnitude higher than the values at 4° C. On the contrary, rhCollagen (dashed lines) shows no significant difference between $\eta_0$ values at 4° C. and 37° C.

FIG. 3 presents comparative plots showing the viscosity of rhCollagen neutralized in FB, prepared as described hereinabove, and indicate a very similar behavior, i.e., the viscosity at 4° C. and 37° C. is almost identical, at all shear rates.

Viscosity of rhCollagen-Methacrylamide:

FIG. 4 presents comparative plots showing the viscosity of fibrillar rhCollagen-MA in DPBS at 4° C. (solid line) and 37° C. (dashed line), and indicate that the profiles are similar (both are shear thinning) but not identical, yet, the zero shear rate values are around 1000 cP at both temperatures.

FIG. 5 presents comparative plots further demonstrating the thermal stability and, importantly, the decrease in viscosity within a range of increased working (e.g., jetting) temperatures, compared with an increase in viscosity as the temperature increases shown for bovine-based methacrylated curable collagen. Viscosity measurements were performed with increased temperature steps, for 10 mg/ml rhCollagen-MA solution in 20 mM acetic acid (white circles) and for bovine-based curable collagen in acetic acid (black circles), as recorded in the rheometer using Rotational temperature steps CR mode with 5 [1/sec] rate. The acetic acid solutions were prepared as described hereinabove.

Example 3

Characterization of Hardened Rh-Collagen-MA rhCollagen-MA Photocrosslinking for Loss and Storage Moduli Measurements:

rhCollagen-MA crosslinked scaffolds were formed in two different preparations, aimed to be examined in two individual experiments, respectively.

A photoinitiator 10% (v/v) stock solution was prepared as follows: Irgacure 2959 was dissolved in ethanol absolute/DDW 1:1 solution to a final concentration of 100 mg/mL.

In the first preparation, 1-2 wt % fibrillar rhCollagen-MA synthesized with 10-fold molar excess of the methacrylic reagent were dissolved in DPBS 0.1 M at room temperature, then Irgacure 2959 0.1% was added into 1 mL final volume of solution replicates which were injected into a discoid mold. Thereafter, curing process was performed from a distance of 1.5 cm for 7 and 10 seconds at an averaged intensity of 670 mW/cm$^2$ using mercury light source, resulting in cross-linked scaffolds.

The second preparation included 2 different batches of fibrillar rhCollagen-MA, synthesized with 15-fold and 20-fold molar excess of the methacrylic reagent. 1-2 wt % were dissolved in DPBS 0.1 M, and Irgacure 2959 0.1% was added to achieve a final volume of 1.5 mL. In order to obtain highly crosslinked scaffolds, curing process was performed from a distance of 2 cm for 60 seconds at an averaged intensity of 420 mW/cm$^2$, using mercury light source.

Scaffolds' Storage and Loss Moduli Measurements:

The rheological behavior of rhCollagen crosslinked discs was investigated using parallel plate system employing PP20 serrated spindle and 20 mm serrate plate set up. Characterization of the non-crosslinked rhCollagen-MA was performed using C60/l° Ti cone-plate elements.

In order to evaluate the rheological behavior of rhCollagen-MA, two sets of experiments were performed individually.

In the first set, oscillation over time analysis was conducted at 37° C. and is presented in FIGS. 6-A and 6-B. 1 mL samples were subjected to oscillation forces at controlled stress mode, while applying 5 Pa shear stress at 1 Hz frequency and 37° C. for 300 seconds. FIG. 6A presents loss/storage moduli (G'/G") and the tan (delta) values before UV curing, and FIG. 6B presents these values following exposure to light curing (following curing by cross-linking upon addition of a photoinitiator). The cured samples, 1 ml discs, were tested as the gap was adjusted to 90% of the original sample height. G' and G" values were averaged at the range of 150-300 seconds in all measurements.

The results demonstrate that the storage modulus of the rhCollagen-MA increases by 2-folds upon illumination (curing by irradiation) in the presence of a photoinitiator. Moreover, the results demonstrate the ability to control the scaffold properties by changing the rhCollagen-MA concentration and time of illumination (irradiation; exposure to a curing condition). High differences between G' and G" values, and close-to-zero tan (delta) values of the cross-linked discs indicate an elastic-like behavior.

In the second set, 1.5 mL cured (cross-linked) discs were characterized by applying oscillations under frequency sweep at 37° C. G' was recorded under 1 Pa shear stress at frequency range of 0.01-100 Hz. To initiate measurement, the spindle was lowered to contact the hydrogel surface, and then further lowered until the axial force of the instrument was equal to 0.4 N.

Prior to all measurements, samples were kept on the plate covered with humidity lid for 1 minute, in order to reach temperature equilibrium.

The results are presented in FIG. 7, and show that 1.5 mL discs illuminated for 60 seconds feature higher G' values. G' increases with increasing rhCollagen-MA concentration and increasing degree of methacrylation, indicating the ability to control the scaffolds properties.

In Situ Crosslinking of rhCollagen-MA:

A solution of 15 mg/ml monomeric rhCollagen-MA in 10 mM HCl was prepared by adding the appropriate volume of the medium to the lyophilized material, and after full dissolution, 0.1% of Irgacure photoinitiator was added to each replicate.

In situ crosslinking of rhCollagen-MA was tested by applying oscillation forces over time at 25° C. using 7% strain and angular frequency of 5 rad/sec. 80 µl solution was placed in 20 mm parallel plate geometry, and G' and complexed viscosity properties were first measured prior to cross-linking as described hereinabove. Thereafter an external UV 365 nm light source was introduced, and the properties of the sample were recorded over time during the cross-linking reaction on the plate.

The results are presented in FIG. 8. As shown therein, an immediate sharp increase in the tested properties was observed during a short period, reaching a plateau after less than 30 seconds, indicating a good curability of the formulation. After 60 seconds curing, light source was off and values were kept measured post curing over time, showing similar values and indicating stability.

Example 4

Characterization of rhCollagen-MA Formulations in Varying Mediums and/or with Varying Additives Preparation of DMEM Formulations:

rhCollagen-methacrylamide in DMEM: Lyophilized fibrillar rhCollagen-methacrylamide (prepared as described in Example 1 hereinabove, using with 15:1 molar ratio of MA:rhCollagen) was dissolved in DMEM medium to final concentrations of 20 and 26 mg/mL.

rhCollagen-methacrylamide/Hyaluronic Acid in DMEM: Hyaluronic Acid was added to a solution of fibrillar rhCollagen-MA to obtain final concentrations of 10 mg/mL HA and 20 mg/mL rhCollagen-MA in DMEM medium.

Preparation of Hyaluronic Acid Methacrylate (HAMA):

500 mg of HA were functionalized as described by Leach et al. [Leach et. al. 2002, Biotechnology and Bioengineering, vol. 82, no. 5]. Briefly, 1.8 mL of triethylamine, 1.8 mL of glycidyl methacrylate, and 1.8 grams of tetrabutyl ammonium bromide were added separately to 50 mL of 10 mg/mL HA solution in DDW, while thoroughly mixing the reaction mixture before the addition of each component. The obtained reaction mixture was stirred overnight at room temperature, and thereafter the HAMA was precipitated by adding 20-folds volume of acetone and was then re-dissolved in DDW. The precipitation process was repeated twice to eliminate all possible side products, and the obtained reaction product was then lyophilized.

rhCollagen-methacrylamide/Hyaluronic Acid methacrylate (HAMA) in DMEM: Hyaluronic Acid methacrylate prepared as described hereinabove was added to a solution of fibrillar rhCollagen-MA to obtain final concentrations of 10 mg/mL HA-MA and 20 mg/mL rhCollagen-MA in DMEM medium.

Viscosity of DMEM Formulations:

The viscosity of rhCollagen-MA in DMEM at 25° C., alone and in the presence of hyaluronic acid (HA) or HA-MA (prepared as described in Example 1) was tested, and the obtained data is presented in FIG. 9.

As can be seen therein, the typical shear thinning behavior of the rhCollagen shown in FIGS. 2 and 3 is maintained also for the rhCollagen-MA with and without the addition of HA/HA-MA. Upon increasing the concentration of rhCollagen from 20 to 26 mg/mL the zero shear viscosity increases, and the same is observed upon the addition of 10 mg/mL HA or HAMA (which leads to final polymer concentration of 30 mg/mL).

Preparation of Formulations in 0.1M Phosphate Buffer 0.1M (pH 7.4)/NaCl 11.3 mM:

Stock solutions of 7.5 mg/ml monomeric rhCollagen-methacrylamide (10 fold) in Phosphate Buffer (0.1 M)/Saline (11.3 mM), 30 mg/ml PVAMA in Phosphate Buffer (0.1 M)/Saline (11.3 mM), 30 mg/ml $TiO_2$ in Phosphate Buffer (0.1 M)/Saline (11.3 mM), 30 mg/ml Oxidized Cellulose in Phosphate Buffer (0.1 M)/Saline (11.3 mM) were prepared. HAMA was purchased from Advanced BioMatrix and dissolved to 10 mg/ml in 10 mM HCl. 4.5 ml of HAMA solution were eventually neutralized by adding 0.5 ml of 1M Phosphate buffer+113 mM NaCl.

Preparation of monomeric rhCollagen-methacrylamide in Phosphate Buffer (0.1M)/Saline (11.3 mM): Stock solution of monomeric rhCollagen methacrylamide was dilute to 5 mg/ml with 0.1M Phosphate Buffer (pH7.4)+11.3 mM NaCl Preparation of rhCollagen-methacrylamide and HAMA in Phosphate Buffer (0.1 M/Saline (11.3 mM): Solutions of CollagenMA (monomeric rhCollagen-methacrylamide) and HAMA in a weight ratio of collagenMA:HAMA 5:1 and 2:1 were prepared by mixing the appropriate amount of the collagenMA and HAMA stock solutions described herein above with Phosphate Buffer (0.1 M)/Saline (11.3 mM) to obtain final concentrations of 5 mg/ml ColiMA and 1 mg/ml HAMA (5:1 ratio) and 5 mg/ml coil MA and 2.5 mg/ml HAMA (2:1 ratio), respectively.

Preparation of rhCollagen-methacrylamide and PVAMA in Phosphate Buffer (0.1 M)/Saline (11.3 mM): CollagenMA (monomeric rhCollagen-methacrylamide) and PVAMA in a weight ratio of collagenMA:PVAMA 5:1, 2:1 and 1:2 were prepared by mixing the appropriate amount of the collagenMA and PVAMA stock solutions described herein above with Phosphate Buffer (0.1 M)/Saline (11.3 mM) to obtain final concentrations of 5 mg/ml CollMA and 1 mg/ml PVAMA (5:1 ratio), 5 mg/ml collMA and 2.5 mg/ml PVAMA (2:1 ratio) and 5 mg/ml CollMA and 10 mg/ml PVAMA (1:2 ratio), Preparation of rhCollagen-methacrylamide and Titanium Dioxide ($TiO_2$) in Phosphate Buffer (0.1 M)/Saline (11.3 mM): CollagenMA (monomeric rhCollagen-methacrylamide) and Titanium Dioxide ($TiO_2$) in a weight ratio of collagenMA:Titanium Dioxide ($TiO_2$) of 5:1, 2:1 and 1:2 were prepared by mixing the appropriate amount of the collagenMA and Titanium Dioxide ($TiO_2$) stock solutions described herein above with Phosphate Buffer (0.1 M)/Saline (11.3 mM) to obtain final concentrations of 5 mg/ml CollMA and 1 mg/ml Titanium Dioxide ($TiO_2$) (5:1 ratio), 5 mg/mi collMA and 2.5 mg/ml Titanium Dioxide ($TiO_2$) (2:1 ratio) and mg/ml CollMA and 10 mg/ml Titanium Dioxide ($TiO_2$) (1:2 ratio).

Preparation of rhCollagen-methacrylamide and oxidized cellulose in Phosphate Buffer (0.1 M)/Saline (11.3 mM): CollagenMA (monomeric rhCollagen-methacrylamide) and oxidized cellulose in a weight ratio of collagenMA:oxidized cellulose of 5:1, 2:1 and 1:2 were prepared by mixing the appropriate amount of the collagenMA and oxidized cellulose stock solutions described hereinabove with Phosphate Buffer (0.1 M)/Saline (11.3 mM) to obtain final concentrations of 5 mg/ml CollMA and 1 mg/ml oxidized cellulose (5:1 ratio), 5 mg/ml collMA and 2.5 mg/ml oxidized cellulose (2:1 ratio) and 5 mg/ml CollMA and 10 mg/ml oxidized cellulose (1:2 ratio).

Viscosity of Formulations in 0.1M Phosphate Buffer 0.1M (pH 7.4)/NaCl 11.3 mM:

The viscosity of formulations containing 5 mg/ml rhCollagen methacrylate (rhCollagen-MA; col) enriched with different additives (polyvinyl alcohol methacrylate (PVAMA), hyaluronic acid methacrylate (HAMA), Titanium Dioxide (TiO2) and oxidized cellulose (OC)) at collagenMA:additive ratios of 5:1, 2:1 and 1:2, in 0.1 M Phosphate buffer pH 7.4/11.3 mM NaCl (physiological osmolarity), prepared as described herein, was tested. Measurements were performed at T=22° C., using a cone on plate configuration (spindle C35/1 Ti Thermo HAAKE Rheo Stress 600 instrument). The obtained data is presented in FIGS. 10-13.

FIG. 10 presents comparative plots showing the viscosity of 5 mg/ml rhCollagen-MA (colMA) and 5 mg/ml rhCollagen-MA+Polyvinyl alcohol methacrylate (PVAMA) at rhCollagen-MA:PVAMA weight ratio of 5:1, 2:1, and 1:2.

FIG. 11 presents comparative plots showing the viscosity of 5 mg/ml rhCollagen-MA (colMA) and 5 mg/ml rhCollagen-MA+HAMA at rhCollagen-MA:HAMA weight ratio of 5:1 and 2:1.

FIG. 12 presents comparative plots showing the viscosity of 5 mg/ml rhCollagen-MA (colMA) and 5 mg/ml rhCollagen-MA+TiO$_2$ at rhCollagen-MA:HAMA weight ratio of 5:1, 2:1, and 1:2.

FIG. 13 presents comparative plots showing the viscosity of 5 mg/ml rhCollagen-MA (colMA) and 5 mg/ml rhCollagen-MA+oxidized cellulose at rhCollagen-MA:HAMA weight ratio of 5:1, 2:1, and 1:2.

Cured rhCollagen-MA Formulations in 0.1M Phosphate Buffer 0.1M (pH 7.4)/NaCl 11.3 mM:

The above-described formulations, containing rhCollagen-MA alone or with the different additives at 2:1 collagen:additive weight ratio were mixed with the photoinitiator 2-Hydroxy-4'-(2-hydroxyethoxy)-2-methylpropiophenone (0.1%). 130 μL of the formulations were introduced in a silicon mold (8 mm×8 mm×8 mm) and illuminated for 20 seconds with UV light (365 nm) at a distance of 1.5 cm.

FIG. 14 presents images of the obtained mold objects.

Viscosity of rhCollagen-MA Formulations in Phosphate Buffer and in HCl and G' Measurements of Cured Objects Made Therefrom:

10 mg/ml monomeric rhCollagen-MA (10-fold) solutions in phosphate buffer 0.1M/NaCl 15.8 mM (about 16 mM) or in 10 mM HCl were prepared by adding the appropriate volume of the medium to the lyophilized material. After complete dissolution the formulation's viscosity was tested before curing.

The viscosity of these formulations at increased frequency was recorded in a rheometer using Rotational CR mode at room temperature, and the obtained data is presented in FIG. 15. As shown therein, a 0.1M phosphate buffer/0.016M NaCl (total of 300 mOs/L) formulation presents higher viscosity (light grey) than a 10 mM HCl (dark grey) and 20 mM Acetic Acid (data not shown). The shear thinning behavior in this phosphate buffer medium is more pronounced compared with all other tested media.

These formulations were also subjected to curing at 365 nm by UV LED source. 1.6 ml of solution with 0.1% photoinitiator was injected into a discoid mold and curing was performed using 100 mW/cm$^2$ for 90 seconds, and G' values at increased frequency of the cured objects was measured in a rheometer using Oscillation CR mode at 37° C.

The obtained data is shown in FIG. 16, indicating a higher storage modulus of the cured objects formed of a phosphate buffer-based formulation.

Example 5

A liquid solution of 20 mg/ml, monomeric rhCollagen-MA (prepared using 10-folds molar excess of MA) in Hepes Buffered saline was mixed with N-vinyl pyrrolidinone and Eosin Y/TEA (triethanolamine) as a photoinitiator. 120 microliters were then dispensed in a silicon mold (8 mm×8 mm×3 mm) and covered with a mouse skin patch (Science in Action Ltd.). The formulation was polymerized transdermally by illuminating the external side of the skin patch with white light from a white LED torch for 6 minutes.

FIG. 17 presented a photograph, taken using a camera, of the skin patch following illumination, and show that the rhCollagen-MA polymerized and was integrated into the skin tissue.

Example 6

Monomeric rhCollagen-MA alone and rhCollagen-MA (monomeric) combined with calcium phosphate particles were evaluated in a cell proliferation assay using Normal human dermal fibroblasts (Promocell).

Objects (scaffolds) were prepared from lyophilized rhCollagen-MA dissolved in DDW containing (1) rhCollagen-MA alone, 9 mg/ml; (2) rhCollagen-MA, 9 mg/ml and nano-hydroxyapatite (nanoHA), 7 mg/ml; and (3) rhCollagen-MA, 9 mg/ml and nano-tricalcium phosphate (nanoTCP), 7 mg/ml. Each solution was subjected to UV curing, lyophilized and sterilized with ethylene oxide (ETO). Normal human dermal fibroblasts were seeded on the scaffolds and cell proliferation was measured using colorimetric assay (WST-1) on day 1, 3 and 7. FIG. 18 presents the obtained data and demonstrate good cell proliferation in all tested formulations.

Although the invention has been described in conjunction with specific embodiments thereof, it is evident that many alterative, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A process of additive manufacturing a three-dimensional object featuring, in at least a portion thereof, a collagen-based material, the process comprising sequentially forming a plurality of layers in a configured pattern corresponding to a shape of the object,
wherein for at least a portion of said layers, said layers are formed of a modeling material formulation that comprises a plant-derived recombinant human collagen featuring at least one curable group,
wherein forming said layers is at a temperature of at least 20° C., and wherein said modeling material formulation features a viscosity of no more than 2000 centipoises, at a shear strain of 5 1/sec, at room temperature, wherein a concentration of said recombinant human collagen featuring a curable group is at least 3 mg/mL, and said modeling material formulation maintains said viscosity when said layers are formed,
thereby manufacturing the three-dimensional object.

2. The process of claim 1, further comprising exposing each layer of said portion of said formed layers to a curing condition suitable for hardening said recombinant human collagen featuring said at least one curable group.

3. The process of claim 1, wherein said recombinant human collagen is a recombinant human Type I collagen.

4. The process of claim 1, wherein said modeling material formulation that comprises said recombinant human collagen further comprises an aqueous carrier.

5. The process of claim 4, wherein said modeling material formulation has a pH that ranges from about 6 to about 8.

6. The process of claim 1, wherein for at least a portion of said layers, said layers are formed of a modeling material formulation that comprises at least one curable material other than said recombinant human collagen featuring said curable group; and/or of a modeling material that comprises an agent that modifies a mechanical and/or rheological and/or physical property of the formulation and/or of a respective portion of the object; and/or of a modeling material formulation that comprises a biological material other than said human recombinant collagen.

7. The process of claim 6, wherein said layers are formed of a modeling material formulation that comprises said recombinant human collagen featuring said curable group and said at least one curable material.

8. The process of claim 7, wherein a weight ratio of said recombinant human collagen featuring said curable group and said at least one curable material ranges from 10:1 to 1:2.

9. The process of claim 1, wherein said modeling material formulation features a viscosity of no more than 2,000 centipoises, at a zero shear strain rate, at 37° C., wherein a concentration of said recombinant human collagen featuring a curable group is at least 3 mg/mL.

10. The process of claim 1, wherein said modeling material formulation features, when hardened, storage modulus (G') of at least 1,000 Pa.

11. The process of claim 1, wherein said modeling material features, when hardened, an increase of at least 10-folds of its storage modulus (G').

12. The process of claim 1, wherein forming said layers is at a temperature of 37° C.

13. The process of claim 1, wherein said additive manufacturing is 3D inkjet printing and wherein forming said layers is by dispensing droplets of said modeling material formulation using at least one inkjet printing head.

14. The process of claim 1, wherein said additive manufacturing is digital light processing or stereolithography and wherein sequentially forming said layers comprises hardening said modeling material formulation in a bath, layer by layer, by selective curing using a light source, to thereby form a hardened material, and separating the uncured modeling material formulation from the hardened material.

15. A process of additive manufacturing a three-dimensional object featuring, in at least a portion thereof, a collagen-based material, the process comprising dispensing at least one modeling material formulation to sequentially form a plurality of layers in a configured pattern corresponding to a shape of the object,
wherein for at least a portion of said layers, said dispensing is of a modeling material formulation that comprises a plant-derived recombinant human collagen featuring at least one photocurable group, wherein said modeling material formulation features a viscosity of no more than 2000 centipoises, at a shear strain of 5 1/sec, at room temperature, when a concentration of said recombinant human collagen featuring a curable group is at least 3 mg/mL,
and wherein said dispensing is at a temperature of at least 20° C., and comprises dispensing droplets of said modeling material formulation using at least one inkjet printing head,
the process further comprising exposing each layer of said portion of said formed layers to a curing condition suitable for hardening said modeling material formulation, said curing condition comprising electromagnetic irradiation, wherein said modeling material features, when hardened, an increase of at least 10-folds of its storage modulus (G').

16. The process of claim 15, wherein said recombinant human collagen is a recombinant human Type I collagen.

17. The process of claim 15, wherein for at least a portion of said layers, said dispensing is further of a modeling material formulation that comprises at least one curable material other than said recombinant human collagen featuring said curable group; and/or of a modeling material that comprises an agent that modifies a mechanical and/or rheological and/or physical property of the formulation and/or of a respective portion of the object; and/or of a modeling material formulation that comprises a biological material other than said human recombinant collagen.

18. A process of additive manufacturing a three-dimensional object featuring, in at least a portion thereof, a collagen-based material, the process comprising sequentially forming a plurality of layers in a configured pattern corresponding to a shape of the object, and exposing each of said layers to a curing condition, wherein sequentially forming the plurality of layers comprises hardening a modeling material formulation in a bath, layer by layer, by selective curing using a light source to thereby form a hardened material, and separating the uncured modeling material formulation from the hardened material, wherein for at least a portion of said layers, said layers are formed of a modeling material formulation that comprises a plant-derived recombinant human collagen featuring at least one photocurable group, wherein forming said layers is at a temperature of at least 20° C., and wherein said modeling material formulation features a viscosity of no more than 2000 centipoises, at a shear strain of 5 1/sec, at room temperature, wherein a concentration of said recombinant human collagen featuring a curable group is at least 3 mg/mL, thereby manufacturing the three-dimensional object.

19. The process of claim 18, wherein said recombinant human collagen is a recombinant human Type I collagen.

20. The process of claim 18, wherein for at least a portion of said layers, said layers are formed of a modeling material formulation that comprises at least one photocurable material other than said recombinant human collagen featuring said curable group; and/or of a modeling material that comprises an agent that modifies a mechanical and/or rheological and/or physical property of the formulation and/or of a respective portion of the object; and/or of a modeling material formulation that comprises a biological material other than said human recombinant collagen.

* * * * *

SEQUENCE LISTING

<160> NUMBER OF SEQ ID NOS: 16

<210> SEQ ID NO 1
<211> LENGTH: 1464
<212> TYPE: PRT
<213> ORGANISM: Homo sapiens

<400> SEQUENCE: 1

```
Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30
```

-continued

```
Glu Asp Ile Pro Pro Ile Thr Cys Val Gln Asn Gly Leu Arg Tyr His
         35                  40                  45

Asp Arg Asp Val Trp Lys Pro Glu Pro Cys Arg Ile Cys Val Cys Asp
 50                  55                  60

Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                 85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
            130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
            195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
    275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
            355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
            435                 440                 445

Gly Glu Pro Gly Pro Val Gly Val Gln Gly Pro Pro Gly Pro Ala Gly
```

```
            450             455             460
Glu Glu Gly Lys Arg Gly Ala Arg Gly Glu Pro Gly Pro Thr Gly Leu
465                 470                 475                 480

Pro Gly Pro Pro Gly Glu Arg Gly Pro Gly Ser Arg Gly Phe Pro
                485                 490                 495

Gly Ala Asp Gly Val Ala Gly Pro Lys Gly Pro Ala Gly Glu Arg Gly
                500                 505                 510

Ser Pro Gly Pro Ala Gly Pro Lys Gly Ser Pro Gly Glu Ala Gly Arg
            515                 520                 525

Pro Gly Glu Ala Gly Leu Pro Gly Ala Lys Gly Leu Thr Gly Ser Pro
530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Gly Ala Arg Gly Gln
                565                 570                 575

Ala Gly Val Met Gly Phe Pro Gly Pro Lys Gly Ala Ala Gly Glu Pro
                580                 585                 590

Gly Lys Ala Gly Glu Arg Gly Val Pro Gly Pro Pro Gly Ala Val Gly
            595                 600                 605

Pro Ala Gly Lys Asp Gly Glu Ala Gly Ala Gln Gly Pro Pro Gly Pro
610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
                660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
                740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
850                 855                 860

Arg Gly Ser Ala Gly Pro Pro Gly Ala Thr Gly Phe Pro Gly Ala Ala
865                 870                 875                 880
```

```
Gly Arg Val Gly Pro Pro Pro Ser Gly Asn Ala Gly Pro Pro Gly
            885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
            930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
            965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Ala Gly Pro Val Gly Pro Val Gly Ala
    1070                1075                1080

Arg Gly Pro Ala Gly Pro Gln Gly Pro Arg Gly Asp Lys Gly Glu
    1085                1090                1095

Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185

Pro Gly Pro Pro Ser Ala Gly Phe Asp Phe Ser Phe Leu Pro Gln
    1190                1195                1200

Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275
```

```
Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460
```

<210> SEQ ID NO 2
<211> LENGTH: 1366
<212> TYPE: PRT
<213> ORGANISM: Homo sapiens

<400> SEQUENCE: 2

```
Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
                35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
                100                 105                 110

Phe Gln Gly Pro Ala Gly Glu Pro Gly Glu Pro Gly Gln Thr Gly Pro
            115                 120                 125

Ala Gly Ala Arg Gly Pro Ala Gly Pro Pro Gly Lys Ala Gly Glu Asp
        130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175
```

```
Lys Gly Ile Arg Gly His Asn Gly Leu Asp Gly Leu Lys Gly Gln Pro
            180                 185                 190
Gly Ala Pro Gly Val Lys Gly Glu Pro Gly Ala Pro Gly Glu Asn Gly
            195                 200                 205
Thr Pro Gly Gln Thr Gly Ala Arg Gly Leu Pro Gly Glu Arg Gly Arg
210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Ile Gly Ser Ala Gly Pro Pro Gly
            245                 250                 255
Phe Pro Gly Ala Pro Gly Pro Lys Gly Glu Ile Gly Ala Val Gly Asn
            260                 265                 270
Ala Gly Pro Ala Gly Pro Ala Gly Pro Arg Gly Glu Val Gly Leu Pro
            275                 280                 285
Gly Leu Ser Gly Pro Val Gly Pro Pro Gly Asn Pro Gly Ala Asn Gly
            290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
            325                 330                 335
Gly Ala Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
            355                 360                 365
Gln Gly Pro Pro Gly Pro Ser Gly Glu Glu Gly Lys Arg Gly Pro Asn
            370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
            405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
            435                 440                 445
Pro Arg Gly Leu Pro Gly Ser Pro Gly Asn Ile Gly Pro Ala Gly Lys
450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
            485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
            515                 520                 525
Gly Ala Gln Gly Pro Pro Gly Pro Gln Gly Val Gln Gly Gly Lys Gly
            530                 535                 540
Glu Gln Gly Pro Ala Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
            565                 570                 575
Gly Glu Phe Gly Leu Pro Gly Pro Ala Gly Pro Arg Gly Glu Arg Gly
            580                 585                 590
```

-continued

```
Pro Pro Gly Glu Ser Gly Ala Ala Gly Pro Thr Gly Pro Ile Gly Ser
            595                 600                 605

Arg Gly Pro Ser Gly Pro Pro Gly Pro Asp Gly Asn Lys Gly Glu Pro
        610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly Pro Gln Gly Ile Arg Gly Asp Lys
        995                 1000                1005

Gly Glu Pro Gly Glu Lys Gly Pro Arg Gly Leu Pro Gly Leu Lys
```

| | | 1010 | | | | 1015 | | | | 1020 | |

Gly His Asn Gly Leu Gln Gly Leu Pro Gly Ile Ala Gly His His
    1025                        1030                        1035

Gly Asp Gln Gly Ala Pro Gly Ser Val Gly Pro Ala Gly Pro Arg
    1040                        1045                        1050

Gly Pro Ala Gly Pro Ser Gly Pro Ala Gly Lys Asp Gly Arg Thr
    1055                        1060                        1065

Gly His Pro Gly Thr Val Gly Pro Ala Gly Ile Arg Gly Pro Gln
    1070                        1075                        1080

Gly His Gln Gly Pro Ala Gly Pro Pro Gly Pro Pro Gly Pro Pro
    1085                        1090                        1095

Gly Pro Pro Gly Val Ser Gly Gly Gly Tyr Asp Phe Gly Tyr Asp
    1100                        1105                        1110

Gly Asp Phe Tyr Arg Ala Asp Gln Pro Arg Ser Ala Pro Ser Leu
    1115                        1120                        1125

Arg Pro Lys Asp Tyr Glu Val Asp Ala Thr Leu Lys Ser Leu Asn
    1130                        1135                        1140

Asn Gln Ile Glu Thr Leu Leu Thr Pro Glu Gly Ser Arg Lys Asn
    1145                        1150                        1155

Pro Ala Arg Thr Cys Arg Asp Leu Arg Leu Ser His Pro Glu Trp
    1160                        1165                        1170

Ser Ser Gly Tyr Tyr Trp Ile Asp Pro Asn Gln Gly Cys Thr Met
    1175                        1180                        1185

Asp Ala Ile Lys Val Tyr Cys Asp Phe Ser Thr Gly Glu Thr Cys
    1190                        1195                        1200

Ile Arg Ala Gln Pro Glu Asn Ile Pro Ala Lys Asn Trp Tyr Arg
    1205                        1210                        1215

Ser Ser Lys Asp Lys Lys His Val Trp Leu Gly Glu Thr Ile Asn
    1220                        1225                        1230

Ala Gly Ser Gln Phe Glu Tyr Asn Val Glu Gly Val Thr Ser Lys
    1235                        1240                        1245

Glu Met Ala Thr Gln Leu Ala Phe Met Arg Leu Leu Ala Asn Tyr
    1250                        1255                        1260

Ala Ser Gln Asn Ile Thr Tyr His Cys Lys Asn Ser Ile Ala Tyr
    1265                        1270                        1275

Met Asp Glu Glu Thr Gly Asn Leu Lys Lys Ala Val Ile Leu Gln
    1280                        1285                        1290

Gly Ser Asn Asp Val Glu Leu Val Ala Glu Gly Asn Ser Arg Phe
    1295                        1300                        1305

Thr Tyr Thr Val Leu Val Asp Gly Cys Ser Lys Lys Thr Asn Glu
    1310                        1315                        1320

Trp Gly Lys Thr Ile Ile Glu Tyr Lys Thr Asn Lys Pro Ser Arg
    1325                        1330                        1335

Leu Pro Phe Leu Asp Ile Ala Pro Leu Asp Ile Gly Gly Ala Asp
    1340                        1345                        1350

Gln Glu Phe Phe Val Asp Ile Gly Pro Val Cys Phe Lys
    1355                        1360                        1365

<210> SEQ ID NO 3
<211> LENGTH: 1464
<212> TYPE: PRT
<213> ORGANISM: Homo sapiens

<400> SEQUENCE: 3

-continued

```
Met Phe Ser Phe Val Asp Leu Arg Leu Leu Leu Leu Ala Ala Thr
1               5                   10                  15

Ala Leu Leu Thr His Gly Gln Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
```

-continued

```
                420             425             430
Ser Gly Glu Pro Gly Ala Pro Gly Ser Lys Gly Asp Thr Gly Ala Lys
            435                 440                 445
Gly Glu Pro Gly Pro Val Gly Val Gln Gly Pro Pro Gly Pro Ala Gly
            450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
            500                 505                 510
Ser Pro Gly Pro Ala Gly Pro Lys Gly Ser Pro Gly Glu Ala Gly Arg
            515                 520                 525
Pro Gly Glu Ala Gly Leu Pro Gly Ala Lys Gly Leu Thr Gly Ser Pro
            530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
            580                 585                 590
Gly Lys Ala Gly Glu Arg Gly Val Pro Gly Pro Pro Gly Ala Val Gly
            595                 600                 605
Pro Ala Gly Lys Asp Gly Glu Ala Gly Ala Gln Gly Pro Pro Gly Pro
            610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
            675                 680                 685
Gly Pro Pro Gly Pro Ala Gly Pro Arg Gly Ala Asn Gly Ala Pro Gly
            690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
            755                 760                 765
Ile Gly Pro Pro Gly Pro Ala Gly Ala Pro Gly Asp Lys Gly Glu Ser
            770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Pro Ala Gly Phe Ala Gly Pro
                805                 810                 815
Pro Gly Ala Asp Gly Gln Pro Gly Ala Lys Gly Glu Pro Gly Asp Ala
            820                 825                 830
Gly Ala Lys Gly Asp Ala Gly Pro Pro Gly Pro Ala Gly Pro Ala Gly
            835                 840                 845
```

```
Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                    885                 890                 895

Pro Pro Gly Pro Ala Gly Lys Glu Gly Lys Gly Pro Arg Gly Glu
            900                 905                 910

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
    930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met  Gly Pro Pro Gly Leu Ala Gly Pro
        995                 1000                1005

Pro Gly Glu Ser Gly Arg Glu  Gly Ala Pro Gly Ala  Glu Gly Ser
    1010                1015                1020

Pro Gly Arg Asp Gly Ser Pro  Gly Ala Lys Gly Asp  Arg Gly Glu
    1025                1030                1035

Thr Gly Pro Ala Gly Pro Pro  Gly Ala Pro Gly Ala  Pro Gly Ala
    1040                1045                1050

Pro Gly Pro Val Gly Pro Ala  Gly Lys Ser Gly Asp  Arg Gly Glu
    1055                1060                1065

Thr Gly Pro Ala Gly Pro Ala  Gly Pro Val Gly Pro  Val Gly Ala
    1070                1075                1080

Arg Gly Pro Ala Gly Pro Gln  Gly Pro Arg Gly Asp  Lys Gly Glu
    1085                1090                1095

Thr Gly Glu Gln Gly Asp Arg  Gly Ile Lys Gly His  Arg Gly Phe
    1100                1105                1110

Ser Gly Leu Gln Gly Pro Pro  Gly Pro Pro Gly Ser  Pro Gly Glu
    1115                1120                1125

Gln Gly Pro Ser Gly Ala Ser  Gly Pro Ala Gly Pro  Arg Gly Pro
    1130                1135                1140

Pro Gly Ser Ala Gly Ala Pro  Gly Lys Asp Gly Leu  Asn Gly Leu
    1145                1150                1155

Pro Gly Pro Ile Gly Pro Pro  Gly Pro Arg Gly Arg  Thr Gly Asp
    1160                1165                1170

Ala Gly Pro Val Gly Pro Pro  Gly Pro Pro Gly Pro  Pro Gly Pro
    1175                1180                1185

Pro Gly Pro Pro Ser Ala Gly  Phe Asp Phe Ser Phe  Leu Pro Gln
    1190                1195                1200

Pro Pro Gln Glu Lys Ala His  Asp Gly Gly Arg Tyr  Tyr Arg Ala
    1205                1210                1215

Asp Asp Ala Asn Val Val Arg  Asp Arg Asp Leu Glu  Val Asp Thr
    1220                1225                1230

Thr Leu Lys Ser Leu Ser Gln  Gln Ile Glu Asn Ile  Arg Ser Pro
    1235                1240                1245
```

```
Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
1265                1270                1275

Asn Gln Gly Cys Asn Leu Asp Ala Ile Lys Val Phe Cys Asn Met
            1280                1285                1290

Glu Thr Gly Glu Thr Cys Val Tyr Pro Thr Gln Pro Ser Val Ala
1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
1325                1330                1335

Gly Gly Gln Gly Ser Asp Pro Ala Asp Val Ala Ile Gln Leu Thr
1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 4
<211> LENGTH: 1366
<212> TYPE: PRT
<213> ORGANISM: Homo sapiens

<400> SEQUENCE: 4

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140
```

-continued

```
Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
                260                 265                 270

Ala Gly Pro Ala Gly Pro Ala Gly Pro Arg Gly Glu Val Gly Leu Pro
            275                 280                 285

Gly Leu Ser Gly Pro Val Gly Pro Pro Gly Asn Pro Gly Ala Asn Gly
        290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
                340                 345                 350

Ser Lys Gly Glu Ser Gly Asn Lys Gly Glu Pro Gly Ser Ala Gly Pro
            355                 360                 365

Gln Gly Pro Pro Gly Pro Ser Gly Glu Glu Gly Lys Arg Gly Pro Asn
        370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
                420                 425                 430

Gly Pro Asn Gly Asp Ala Gly Arg Pro Gly Glu Pro Gly Leu Met Gly
            435                 440                 445

Pro Arg Gly Leu Pro Gly Ser Pro Gly Asn Ile Gly Pro Ala Gly Lys
        450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
                485                 490                 495

Pro Lys Gly Pro Thr Gly Asp Pro Gly Lys Asn Gly Asp Lys Gly His
                500                 505                 510

Ala Gly Leu Ala Gly Ala Arg Gly Ala Pro Gly Pro Asp Gly Asn Asn
            515                 520                 525

Gly Ala Gln Gly Pro Pro Gly Pro Gln Gly Val Gln Gly Gly Lys Gly
        530                 535                 540

Glu Gln Gly Pro Ala Gly Pro Pro Gly Phe Gln Gly Leu Pro Gly Pro
545                 550                 555                 560
```

-continued

```
Ser Gly Pro Ala Gly Glu Val Gly Lys Pro Gly Glu Arg Gly Leu His
            565                 570                 575
Gly Glu Phe Gly Leu Pro Gly Pro Ala Gly Pro Arg Gly Glu Arg Gly
        580                 585                 590
Pro Pro Gly Glu Ser Gly Ala Ala Gly Pro Thr Gly Pro Ile Gly Ser
        595                 600                 605
Arg Gly Pro Ser Gly Pro Pro Gly Pro Asp Gly Asn Lys Gly Glu Pro
    610                 615                 620
Gly Val Val Gly Ala Val Gly Thr Ala Gly Pro Ser Gly Pro Ser Gly
625                 630                 635                 640
Leu Pro Gly Glu Arg Gly Ala Ala Gly Ile Pro Gly Gly Lys Gly Glu
            645                 650                 655
Lys Gly Glu Pro Gly Leu Arg Gly Glu Ile Gly Asn Pro Gly Arg Asp
            660                 665                 670
Gly Ala Arg Gly Ala Pro Gly Ala Val Gly Ala Pro Gly Pro Ala Gly
        675                 680                 685
Ala Thr Gly Asp Arg Gly Glu Ala Gly Ala Ala Gly Pro Ala Gly Pro
        690                 695                 700
Ala Gly Pro Arg Gly Ser Pro Gly Glu Arg Gly Glu Val Gly Pro Ala
705                 710                 715                 720
Gly Pro Asn Gly Phe Ala Gly Pro Ala Gly Ala Ala Gly Gln Pro Gly
            725                 730                 735
Ala Lys Gly Glu Arg Gly Ala Lys Gly Pro Lys Gly Glu Asn Gly Val
            740                 745                 750
Val Gly Pro Thr Gly Pro Val Gly Ala Ala Gly Pro Ala Gly Pro Asn
        755                 760                 765
Gly Pro Pro Gly Pro Ala Gly Ser Arg Gly Asp Gly Gly Pro Pro Gly
        770                 775                 780
Met Thr Gly Phe Pro Gly Ala Ala Gly Arg Thr Gly Pro Pro Gly Pro
785                 790                 795                 800
Ser Gly Ile Ser Gly Pro Pro Gly Pro Pro Gly Pro Ala Gly Lys Glu
            805                 810                 815
Gly Leu Arg Gly Pro Arg Gly Asp Gln Gly Pro Val Gly Arg Thr Gly
            820                 825                 830
Glu Val Gly Ala Val Gly Pro Pro Gly Phe Ala Gly Glu Lys Gly Pro
        835                 840                 845
Ser Gly Glu Ala Gly Thr Ala Gly Pro Pro Gly Thr Pro Gly Pro Gln
        850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Ala Val Gly Glu Pro Gly Pro
            885                 890                 895
Leu Gly Ile Ala Gly Pro Pro Gly Ala Arg Gly Pro Pro Gly Ala Val
            900                 905                 910
Gly Ser Pro Gly Val Asn Gly Ala Pro Gly Glu Ala Gly Arg Asp Gly
        915                 920                 925
Asn Pro Gly Asn Asp Gly Pro Pro Gly Arg Asp Gly Gln Pro Gly His
    930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
            965                 970                 975
Asn Arg Gly Glu Thr Gly Pro Ser Gly Pro Val Gly Pro Ala Gly Ala
```

-continued

```
                980              985              990
Val Gly Pro Arg Gly Pro Ser Gly  Pro Gln Gly Ile Arg  Gly Asp Lys
             995             1000            1005

Gly Glu  Pro Gly Glu Lys Gly  Pro Arg Gly Leu Pro  Gly Leu Lys
        1010             1015            1020

Gly His  Asn Gly Leu Gln Gly  Leu Pro Gly Ile Ala  Gly His His
        1025             1030            1035

Gly Asp  Gln Gly Ala Pro Gly  Ser Val Gly Pro Ala  Gly Pro Arg
        1040             1045            1050

Gly Pro  Ala Gly Pro Ser Gly  Pro Ala Gly Lys Asp  Gly Arg Thr
        1055             1060            1065

Gly His  Pro Gly Thr Val Gly  Pro Ala Gly Ile Arg  Gly Pro Gln
        1070             1075            1080

Gly His  Gln Gly Pro Ala Gly  Pro Pro Gly Pro Pro  Gly Pro Pro
        1085             1090            1095

Gly Pro  Pro Gly Val Ser Gly  Gly Tyr Asp Phe  Gly Tyr Asp
        1100             1105            1110

Gly Asp  Phe Tyr Arg Ala Asp  Gln Pro Arg Ser Ala  Pro Ser Leu
        1115             1120            1125

Arg Pro  Lys Asp Tyr Glu Val  Asp Ala Thr Leu Lys  Ser Leu Asn
        1130             1135            1140

Asn Gln  Ile Glu Thr Leu Leu  Thr Pro Glu Gly Ser  Arg Lys Asn
        1145             1150            1155

Pro Ala  Arg Thr Cys Arg Asp  Leu Arg Leu Ser His  Pro Glu Trp
        1160             1165            1170

Ser Ser  Gly Tyr Tyr Trp Ile  Asp Pro Asn Gln Gly  Cys Thr Met
        1175             1180            1185

Asp Ala  Ile Lys Val Tyr Cys  Asp Phe Ser Thr Gly  Glu Thr Cys
        1190             1195            1200

Ile Arg  Ala Gln Pro Glu Asn  Ile Pro Ala Lys Asn  Trp Tyr Arg
        1205             1210            1215

Ser Ser  Lys Asp Lys Lys His  Val Trp Leu Gly Glu  Thr Ile Asn
        1220             1225            1230

Ala Gly  Ser Gln Phe Glu Tyr  Asn Val Glu Gly Val  Thr Ser Lys
        1235             1240            1245

Glu Met  Ala Thr Gln Leu Ala  Phe Met Arg Leu Leu  Ala Asn Tyr
        1250             1255            1260

Ala Ser  Gln Asn Ile Thr Tyr  His Cys Lys Asn Ser  Ile Ala Tyr
        1265             1270            1275

Met Asp  Glu Glu Thr Gly Asn  Leu Lys Lys Ala Val  Ile Leu Gln
        1280             1285            1290

Gly Ser  Asn Asp Val Glu Leu  Val Ala Glu Gly Asn  Ser Arg Phe
        1295             1300            1305

Thr Tyr  Thr Val Leu Val Asp  Gly Cys Ser Lys Lys  Thr Asn Glu
        1310             1315            1320

Trp Gly  Lys Thr Ile Ile Glu  Tyr Lys Thr Asn Lys  Pro Ser Arg
        1325             1330            1335

Leu Pro  Phe Leu Asp Ile Ala  Pro Leu Asp Ile Gly  Gly Ala Asp
        1340             1345            1350

Gln Glu  Phe Phe Val Asp Ile  Gly Pro Val Cys Phe  Lys
        1355             1360            1365

<210> SEQ ID NO 5
```

<211> LENGTH: 1489
<212> TYPE: PRT
<213> ORGANISM: Homo sapiens

<400> SEQUENCE: 5

Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ser Thr Leu Ala Gln Leu Gln
            35                  40                  45

Glu Glu Gly Gln Val Glu Gly Gln Asp Glu Asp Ile Pro Pro Ile Thr
50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                    85                  90                  95

Asp Val Ile Cys Asp Glu Thr Lys Asn Cys Pro Gly Ala Glu Val Pro
                100                 105                 110

Glu Gly Glu Cys Cys Pro Val Cys Pro Asp Gly Ser Glu Ser Pro Thr
            115                 120                 125

Asp Gln Glu Thr Thr Gly Val Glu Gly Pro Lys Gly Asp Thr Gly Pro
130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
            180                 185                 190

Asp Glu Lys Ser Thr Gly Gly Ile Ser Val Pro Gly Pro Met Gly Pro
        195                 200                 205

Ser Gly Pro Arg Gly Leu Pro Gly Pro Pro Gly Ala Pro Gly Pro Gln
210                 215                 220

Gly Phe Gln Gly Pro Pro Gly Glu Pro Gly Glu Pro Gly Ala Ser Gly
225                 230                 235                 240

Pro Met Gly Pro Arg Gly Pro Pro Gly Pro Pro Gly Lys Asn Gly Asp
                245                 250                 255

Asp Gly Glu Ala Gly Lys Pro Gly Arg Pro Gly Glu Arg Gly Pro Pro
            260                 265                 270

Gly Pro Gln Gly Ala Arg Gly Leu Pro Gly Thr Ala Gly Leu Pro Gly
        275                 280                 285

Met Lys Gly His Arg Gly Phe Ser Gly Leu Asp Gly Ala Lys Gly Asp
    290                 295                 300

Ala Gly Pro Ala Gly Pro Lys Gly Glu Pro Gly Ser Pro Gly Glu Asn
305                 310                 315                 320

Gly Ala Pro Gly Gln Met Gly Pro Arg Gly Leu Pro Gly Glu Arg Gly
                325                 330                 335

Arg Pro Gly Ala Pro Gly Pro Ala Gly Ala Arg Gly Asn Asp Gly Ala
            340                 345                 350

Thr Gly Ala Ala Gly Pro Pro Gly Pro Thr Gly Pro Ala Gly Pro Pro
        355                 360                 365

Gly Phe Pro Gly Ala Val Gly Ala Lys Gly Glu Ala Gly Pro Gln Gly
    370                 375                 380

Pro Arg Gly Ser Glu Gly Pro Gln Gly Val Arg Gly Glu Pro Gly Pro

```
            385                 390                 395                 400
        Pro Gly Pro Ala Gly Ala Ala Gly Pro Ala Gly Asn Pro Gly Ala Asp
                        405                 410                 415
        Gly Gln Pro Gly Ala Lys Gly Ala Asn Gly Ala Pro Gly Ile Ala Gly
                        420                 425                 430
        Ala Pro Gly Phe Pro Gly Ala Arg Gly Pro Ser Gly Pro Gln Gly Pro
                        435                 440                 445
        Gly Gly Pro Pro Gly Pro Lys Gly Asn Ser Gly Glu Pro Gly Ala Pro
                        450                 455                 460
        Gly Ser Lys Gly Asp Thr Gly Ala Lys Gly Glu Pro Gly Pro Val Gly
        465                 470                  475                 480
        Val Gln Gly Pro Pro Gly Pro Ala Gly Glu Glu Gly Lys Arg Gly Ala
                        485                 490                 495
        Arg Gly Glu Pro Gly Pro Thr Gly Leu Pro Gly Pro Pro Gly Glu Arg
                        500                 505                 510
        Gly Gly Pro Gly Ser Arg Gly Phe Pro Gly Ala Asp Gly Val Ala Gly
                        515                 520                 525
        Pro Lys Gly Pro Ala Gly Glu Arg Gly Ser Pro Gly Pro Ala Gly Pro
                        530                 535                 540
        Lys Gly Ser Pro Gly Glu Ala Gly Arg Pro Gly Glu Ala Gly Leu Pro
        545                 550                 555                 560
        Gly Ala Lys Gly Leu Thr Gly Ser Pro Gly Ser Pro Gly Pro Asp Gly
                        565                 570                 575
        Lys Thr Gly Pro Pro Gly Pro Ala Gly Gln Asp Gly Arg Pro Gly Pro
                        580                 585                 590
        Pro Gly Pro Pro Gly Ala Arg Gly Gln Ala Gly Val Met Gly Phe Pro
                        595                 600                 605
        Gly Pro Lys Gly Ala Ala Gly Glu Pro Gly Lys Ala Gly Glu Arg Gly
                        610                 615                 620
        Val Pro Gly Pro Pro Gly Ala Val Gly Pro Ala Gly Lys Asp Gly Glu
        625                 630                 635                 640
        Ala Gly Ala Gln Gly Pro Pro Gly Pro Ala Gly Pro Ala Gly Glu Arg
                        645                 650                 655
        Gly Glu Gln Gly Pro Ala Gly Ser Pro Gly Phe Gln Gly Leu Pro Gly
                        660                 665                 670
        Pro Ala Gly Pro Pro Gly Glu Ala Gly Lys Pro Gly Glu Gln Gly Val
                        675                 680                 685
        Pro Gly Asp Leu Gly Ala Pro Gly Pro Ser Gly Ala Arg Gly Glu Arg
                        690                 695                 700
        Gly Phe Pro Gly Glu Arg Gly Val Gln Gly Pro Pro Gly Pro Ala Gly
        705                 710                 715                 720
        Pro Arg Gly Ala Asn Gly Ala Pro Gly Asn Asp Gly Ala Lys Gly Asp
                        725                 730                 735
        Ala Gly Ala Pro Gly Ala Pro Gly Ser Gln Gly Ala Pro Gly Leu Gln
                        740                 745                 750
        Gly Met Pro Gly Glu Arg Gly Ala Ala Gly Leu Pro Gly Pro Lys Gly
                        755                 760                 765
        Asp Arg Gly Asp Ala Gly Pro Lys Gly Ala Asp Gly Ser Pro Gly Lys
                        770                 775                 780
        Asp Gly Val Arg Gly Leu Thr Gly Pro Ile Gly Pro Pro Gly Pro Ala
        785                 790                 795                 800
        Gly Ala Pro Gly Asp Lys Gly Glu Ser Gly Pro Ser Gly Pro Ala Gly
                        805                 810                 815
```

-continued

```
Pro Thr Gly Ala Arg Gly Ala Pro Gly Asp Arg Gly Glu Pro Gly Pro
            820                 825                 830

Pro Gly Pro Ala Gly Phe Ala Gly Pro Pro Gly Ala Asp Gly Gln Pro
            835                 840                 845

Gly Ala Lys Gly Glu Pro Gly Asp Ala Gly Ala Lys Gly Asp Ala Gly
            850                 855                 860

Pro Pro Gly Pro Ala Gly Pro Ala Gly Pro Pro Gly Pro Ile Gly Asn
865                 870                 875                 880

Val Gly Ala Pro Gly Ala Lys Gly Ala Arg Gly Ser Ala Gly Pro Pro
            885                 890                 895

Gly Ala Thr Gly Phe Pro Gly Ala Ala Gly Arg Val Gly Pro Pro Gly
            900                 905                 910

Pro Ser Gly Asn Ala Gly Pro Pro Gly Pro Pro Gly Pro Ala Gly Lys
            915                 920                 925

Glu Gly Gly Lys Gly Pro Arg Gly Glu Thr Gly Pro Ala Gly Arg Pro
            930                 935                 940

Gly Glu Val Gly Pro Pro Gly Pro Pro Gly Pro Ala Gly Glu Lys Gly
945                 950                 955                 960

Ser Pro Gly Ala Asp Gly Pro Ala Gly Ala Pro Gly Thr Pro Gly Pro
            965                 970                 975

Gln Gly Ile Ala Gly Gln Arg Gly Val Val Gly Leu Pro Gly Gln Arg
            980                 985                 990

Gly Glu Arg Gly Phe Pro Gly Leu Pro Gly Pro Ser Gly Glu Pro Gly
            995                 1000                1005

Lys Gln Gly Pro Ser Gly Ala Ser Gly Glu Arg Gly Pro Pro Gly
            1010                1015                1020

Pro Met Gly Pro Pro Gly Leu Ala Gly Pro Pro Gly Glu Ser Gly
            1025                1030                1035

Arg Glu Gly Ala Pro Gly Ala Glu Gly Ser Pro Gly Arg Asp Gly
            1040                1045                1050

Ser Pro Gly Ala Lys Gly Asp Arg Gly Glu Thr Gly Pro Ala Gly
            1055                1060                1065

Pro Pro Gly Ala Pro Gly Ala Pro Gly Ala Pro Gly Pro Val Gly
            1070                1075                1080

Pro Ala Gly Lys Ser Gly Asp Arg Gly Glu Thr Gly Pro Ala Gly
            1085                1090                1095

Pro Ala Gly Pro Val Gly Pro Ala Gly Ala Arg Gly Pro Ala Gly
            1100                1105                1110

Pro Gln Gly Pro Arg Gly Asp Lys Gly Glu Thr Gly Glu Gln Gly
            1115                1120                1125

Asp Arg Gly Ile Lys Gly His Arg Gly Phe Ser Gly Leu Gln Gly
            1130                1135                1140

Pro Pro Gly Pro Pro Gly Ser Pro Gly Glu Gln Gly Pro Ser Gly
            1145                1150                1155

Ala Ser Gly Pro Ala Gly Pro Arg Gly Pro Pro Gly Ser Ala Gly
            1160                1165                1170

Ala Pro Gly Lys Asp Gly Leu Asn Gly Leu Pro Gly Pro Ile Gly
            1175                1180                1185

Pro Pro Gly Pro Arg Gly Arg Thr Gly Asp Ala Gly Pro Val Gly
            1190                1195                1200

Pro Pro Gly Pro Pro Gly Pro Pro Gly Pro Pro Gly Pro Pro Ser
            1205                1210                1215
```

Ala Gly Phe Asp Phe Ser Phe Leu Pro Gln Pro Pro Gln Glu Lys
1220                 1225                1230

Ala His Asp Gly Gly Arg Tyr Tyr Arg Ala Asp Asp Ala Asn Val
1235                 1240                1245

Val Arg Asp Arg Asp Leu Glu Val Asp Thr Thr Leu Lys Ser Leu
1250                 1255                1260

Ser Gln Gln Ile Glu Asn Ile Arg Ser Pro Glu Gly Ser Arg Lys
1265                 1270                1275

Asn Pro Ala Arg Thr Cys Arg Asp Leu Lys Met Cys His Ser Asp
1280                 1285                1290

Trp Lys Ser Gly Glu Tyr Trp Ile Asp Pro Asn Gln Gly Cys Asn
1295                 1300                1305

Leu Asp Ala Ile Lys Val Phe Cys Asn Met Glu Thr Gly Glu Thr
1310                 1315                1320

Cys Val Tyr Pro Thr Gln Pro Ser Val Ala Gln Lys Asn Trp Tyr
1325                 1330                1335

Ile Ser Lys Asn Pro Lys Asp Lys Arg His Val Trp Phe Gly Glu
1340                 1345                1350

Ser Met Thr Asp Gly Phe Gln Phe Glu Tyr Gly Gly Gln Gly Ser
1355                 1360                1365

Asp Pro Ala Asp Val Ala Ile Gln Leu Thr Phe Leu Arg Leu Met
1370                 1375                1380

Ser Thr Glu Ala Ser Gln Asn Ile Thr Tyr His Cys Lys Asn Ser
1385                 1390                1395

Val Ala Tyr Met Asp Gln Gln Thr Gly Asn Leu Lys Lys Ala Leu
1400                 1405                1410

Leu Leu Lys Gly Ser Asn Glu Ile Glu Ile Arg Ala Glu Gly Asn
1415                 1420                1425

Ser Arg Phe Thr Tyr Ser Val Thr Val Asp Gly Cys Thr Ser His
1430                 1435                1440

Thr Gly Ala Trp Gly Lys Thr Val Ile Glu Tyr Lys Thr Thr Lys
1445                 1450                1455

Thr Ser Arg Leu Pro Ile Ile Asp Val Ala Pro Leu Asp Val Gly
1460                 1465                1470

Ala Pro Asp Gln Glu Phe Gly Phe Asp Val Gly Pro Val Cys Phe
1475                 1480                1485

Leu

<210> SEQ ID NO 6
<211> LENGTH: 1389
<212> TYPE: PRT
<213> ORGANISM: Homo sapiens

<400> SEQUENCE: 6

Met Ala His Ala Arg Val Leu Leu Ala Leu Ala Val Leu Ala Thr
1           5                   10                  15

Ala Ala Val Ala Val Ala Ser Ser Ser Phe Ala Asp Ser Asn Pro
                20                  25                  30

Ile Arg Pro Val Thr Asp Arg Ala Ala Ser Thr Leu Ala Gln Leu Leu
        35                  40                  45

Gln Glu Glu Thr Val Arg Lys Gly Pro Ala Gly Asp Arg Gly Pro Arg
        50                  55                  60

Gly Glu Arg Gly Pro Pro Gly Pro Pro Gly Arg Asp Gly Glu Asp Gly
65                  70                  75                  80

```
Pro Thr Gly Pro Pro Gly Pro Pro Gly Pro Pro Gly Leu
            85              90              95

Gly Gly Asn Phe Ala Ala Gln Tyr Asp Gly Lys Gly Val Gly Leu Gly
            100             105             110

Pro Gly Pro Met Gly Leu Met Gly Pro Arg Gly Pro Pro Gly Ala Ala
            115             120             125

Gly Ala Pro Gly Pro Gln Gly Phe Gln Gly Pro Ala Gly Glu Pro Gly
            130             135             140

Glu Pro Gly Gln Thr Gly Pro Ala Gly Ala Arg Gly Pro Ala Gly Pro
145             150             155             160

Pro Gly Lys Ala Gly Glu Asp Gly His Pro Gly Lys Pro Gly Arg Pro
            165             170             175

Gly Glu Arg Gly Val Val Gly Pro Gln Gly Ala Arg Gly Phe Pro Gly
            180             185             190

Thr Pro Gly Leu Pro Gly Phe Lys Gly Ile Arg Gly His Asn Gly Leu
            195             200             205

Asp Gly Leu Lys Gly Gln Pro Gly Ala Pro Gly Val Lys Gly Glu Pro
            210             215             220

Gly Ala Pro Gly Glu Asn Gly Thr Pro Gly Gln Thr Gly Ala Arg Gly
225             230             235             240

Leu Pro Gly Glu Arg Gly Arg Val Gly Ala Pro Gly Pro Ala Gly Ala
            245             250             255

Arg Gly Ser Asp Gly Ser Val Gly Pro Val Gly Pro Ala Gly Pro Ile
            260             265             270

Gly Ser Ala Gly Pro Pro Gly Phe Pro Gly Ala Pro Gly Pro Lys Gly
            275             280             285

Glu Ile Gly Ala Val Gly Asn Ala Gly Pro Thr Gly Pro Ala Gly Pro
            290             295             300

Arg Gly Glu Val Gly Leu Pro Gly Leu Ser Gly Pro Val Gly Pro Pro
305             310             315             320

Gly Asn Pro Gly Ala Asn Gly Leu Thr Gly Ala Lys Gly Ala Ala Gly
            325             330             335

Leu Pro Gly Val Ala Gly Ala Pro Gly Leu Pro Gly Pro Arg Gly Ile
            340             345             350

Pro Gly Pro Val Gly Ala Ala Gly Ala Thr Gly Ala Arg Gly Leu Val
            355             360             365

Gly Glu Pro Gly Pro Ala Gly Ser Lys Gly Glu Ser Gly Asn Lys Gly
            370             375             380

Glu Pro Gly Ser Ala Gly Pro Gln Gly Pro Pro Gly Pro Ser Gly Glu
385             390             395             400

Glu Gly Lys Arg Gly Pro Asn Gly Glu Ala Gly Ser Ala Gly Pro Pro
            405             410             415

Gly Pro Pro Gly Leu Arg Gly Ser Pro Gly Ser Arg Gly Leu Pro Gly
            420             425             430

Ala Asp Gly Arg Ala Gly Val Met Gly Pro Pro Gly Ser Arg Gly Ala
            435             440             445

Ser Gly Pro Ala Gly Val Arg Gly Pro Asn Gly Asp Ala Gly Arg Pro
            450             455             460

Gly Glu Pro Gly Leu Met Gly Pro Arg Gly Leu Pro Gly Ser Pro Gly
465             470             475             480

Asn Ile Gly Pro Ala Gly Lys Glu Gly Pro Val Gly Leu Pro Gly Ile
            485             490             495

Asp Gly Arg Pro Gly Pro Ile Gly Pro Ala Gly Ala Arg Gly Glu Pro
```

```
                500              505               510
Gly Asn Ile Gly Phe Pro Gly Pro Lys Gly Thr Gly Asp Pro Gly
            515              520              525

Lys Asn Gly Asp Lys Gly His Ala Gly Leu Ala Gly Ala Arg Gly Ala
            530              535              540

Pro Gly Pro Asp Gly Asn Asn Gly Ala Gln Gly Pro Pro Gly Pro Gln
545              550              555              560

Gly Val Gln Gly Lys Gly Glu Gln Gly Pro Ala Gly Pro Pro Gly
                565              570              575

Phe Gln Gly Leu Pro Gly Pro Ser Gly Pro Ala Gly Glu Val Gly Lys
            580              585              590

Pro Gly Glu Arg Gly Leu His Gly Glu Phe Gly Leu Pro Gly Pro Ala
            595              600              605

Gly Pro Arg Gly Glu Arg Gly Pro Pro Gly Glu Ser Gly Ala Ala Gly
            610              615              620

Pro Thr Gly Pro Ile Gly Ser Arg Gly Pro Ser Gly Pro Pro Gly Pro
625              630              635              640

Asp Gly Asn Lys Gly Glu Pro Gly Val Val Gly Ala Val Gly Thr Ala
            645              650              655

Gly Pro Ser Gly Pro Ser Gly Leu Pro Gly Glu Arg Gly Ala Ala Gly
            660              665              670

Ile Pro Gly Gly Lys Gly Glu Lys Gly Glu Pro Gly Leu Arg Gly Glu
            675              680              685

Ile Gly Asn Pro Gly Arg Asp Gly Ala Arg Gly Ala His Gly Ala Val
            690              695              700

Gly Ala Pro Gly Pro Ala Gly Ala Thr Gly Asp Arg Gly Glu Ala Gly
705              710              715              720

Ala Ala Gly Pro Ala Gly Pro Ala Gly Pro Arg Gly Ser Pro Gly Glu
                725              730              735

Arg Gly Glu Val Gly Pro Ala Gly Pro Asn Gly Phe Ala Gly Pro Ala
            740              745              750

Gly Ala Ala Gly Gln Pro Gly Ala Lys Gly Glu Arg Gly Gly Lys Gly
            755              760              765

Pro Lys Gly Glu Asn Gly Val Val Gly Pro Thr Gly Pro Val Gly Ala
            770              775              780

Ala Gly Pro Ala Gly Pro Asn Gly Pro Pro Gly Pro Ala Gly Ser Arg
785              790              795              800

Gly Asp Gly Gly Pro Pro Gly Met Thr Gly Phe Pro Gly Ala Ala Gly
                805              810              815

Arg Thr Gly Pro Pro Gly Pro Ser Gly Ile Ser Gly Pro Pro Gly Pro
            820              825              830

Pro Gly Pro Ala Gly Lys Glu Gly Leu Arg Gly Pro Arg Gly Asp Gln
            835              840              845

Gly Pro Val Gly Arg Thr Gly Glu Val Gly Ala Val Gly Pro Pro Gly
            850              855              860

Phe Ala Gly Glu Lys Gly Pro Ser Gly Glu Ala Gly Thr Ala Gly Pro
865              870              875              880

Pro Gly Thr Pro Gly Pro Gln Gly Leu Leu Gly Ala Pro Gly Ile Leu
                885              890              895

Gly Leu Pro Gly Ser Arg Gly Glu Arg Gly Leu Pro Gly Val Ala Gly
            900              905              910

Ala Val Gly Glu Pro Gly Pro Leu Gly Ile Ala Gly Pro Pro Gly Ala
            915              920              925
```

```
Arg Gly Pro Pro Gly Ala Val Gly Ser Pro Gly Val Asn Gly Ala Pro
    930             935             940

Gly Glu Ala Gly Arg Asp Gly Asn Pro Gly Asn Asp Gly Pro Pro Gly
945             950             955             960

Arg Asp Gly Gln Pro Gly His Lys Gly Glu Arg Gly Tyr Pro Gly Asn
            965             970             975

Ile Gly Pro Val Gly Ala Ala Gly Ala Pro Gly Pro His Gly Pro Val
            980             985             990

Gly Pro Ala Gly Lys His Gly Asn Arg Gly Glu Thr Gly Pro Ser Gly
        995             1000            1005

Pro Val Gly Pro Ala Gly Ala Val Gly Pro Arg Gly Pro Ser Gly
    1010            1015            1020

Pro Gln Gly Ile Arg Gly Asp Lys Gly Glu Pro Gly Glu Lys Gly
    1025            1030            1035

Pro Arg Gly Leu Pro Gly Phe Lys Gly His Asn Gly Leu Gln Gly
    1040            1045            1050

Leu Pro Gly Ile Ala Gly His His Gly Asp Gln Gly Ala Pro Gly
    1055            1060            1065

Ser Val Gly Pro Ala Gly Pro Arg Gly Pro Ala Gly Pro Ser Gly
    1070            1075            1080

Pro Ala Gly Lys Asp Gly Arg Thr Gly His Pro Gly Thr Val Gly
    1085            1090            1095

Pro Ala Gly Ile Arg Gly Pro Gln Gly His Gln Gly Pro Ala Gly
    1100            1105            1110

Pro Pro Gly Pro Pro Gly Pro Pro Gly Pro Pro Gly Val Ser Gly
    1115            1120            1125

Gly Gly Tyr Asp Phe Gly Tyr Asp Gly Asp Phe Tyr Arg Ala Asp
    1130            1135            1140

Gln Pro Arg Ser Ala Pro Ser Leu Arg Pro Lys Asp Tyr Glu Val
    1145            1150            1155

Asp Ala Thr Leu Lys Ser Leu Asn Asn Gln Ile Glu Thr Leu Leu
    1160            1165            1170

Thr Pro Glu Gly Ser Arg Lys Asn Pro Ala Arg Thr Cys Arg Asp
    1175            1180            1185

Leu Arg Leu Ser His Pro Glu Trp Ser Ser Gly Tyr Tyr Trp Ile
    1190            1195            1200

Asp Pro Asn Gln Gly Cys Thr Met Glu Ala Ile Lys Val Tyr Cys
    1205            1210            1215

Asp Phe Pro Thr Gly Glu Thr Cys Ile Arg Ala Gln Pro Glu Asn
    1220            1225            1230

Ile Pro Ala Lys Asn Trp Tyr Arg Ser Ser Lys Asp Lys Lys His
    1235            1240            1245

Val Trp Leu Gly Glu Thr Ile Asn Ala Gly Ser Gln Phe Glu Tyr
    1250            1255            1260

Asn Val Glu Gly Val Thr Ser Lys Glu Met Ala Thr Gln Leu Ala
    1265            1270            1275

Phe Met Arg Leu Leu Ala Asn Tyr Ala Ser Gln Asn Ile Thr Tyr
    1280            1285            1290

His Cys Lys Asn Ser Ile Ala Tyr Met Asp Glu Glu Thr Gly Asn
    1295            1300            1305

Leu Lys Lys Ala Val Ile Leu Gln Gly Ser Asn Asp Val Glu Leu
    1310            1315            1320
```

-continued

```
Val Ala Glu Gly Asn Ser Arg Phe Thr Tyr Thr Val Leu Val Asp
    1325                1330                1335

Gly Cys Ser Lys Lys Thr Asn Glu Trp Gly Lys Thr Ile Ile Glu
    1340                1345                1350

Tyr Lys Thr Asn Lys Pro Ser Arg Leu Pro Phe Leu Asp Ile Ala
    1355                1360                1365

Pro Leu Asp Ile Gly Gly Ala Asp His Glu Phe Phe Val Asp Ile
    1370                1375                1380

Gly Pro Val Cys Phe Lys
    1385
```

<210> SEQ ID NO 7
<211> LENGTH: 5927
<212> TYPE: DNA
<213> ORGANISM: Homo sapiens

<400> SEQUENCE: 7

| | | | | | |
|---|---|---|---|---|---|
| tcgtcggagc | agacgggagt | ttctcctcgg | ggtcggagca | ggaggcacgc | ggagtgtgag | 60 |
| gccacgcatg | agcggacgct | aaccccctcc | ccagccacaa | agagtctaca | tgtctagggt | 120 |
| ctagacatgt | tcagctttgt | ggacctccgg | ctcctgctcc | tcttagcggc | caccgccctc | 180 |
| ctgacgcacg | gccaagagga | aggccaagtc | gagggccaag | acgaagacat | cccaccaatc | 240 |
| acctgcgtac | agaacggcct | caggtaccat | gaccgagacg | tgtggaaacc | cgagccctgc | 300 |
| cggatctgcg | tctgcgacaa | cggcaaggtg | ttgtgcgatg | acgtgatctg | tgacgagacc | 360 |
| aagaactgcc | ccgcgccga | agtccccgag | ggcgagtgct | gtccgtctg | ccccgacggc | 420 |
| tcagagtcac | ccaccgacca | agaaaccacc | ggcgtcgagg | acccaaggg | agacactggc | 480 |
| ccccgaggcc | caaggggacc | cgcaggcccc | cctggccgag | atggcatccc | tggacagcct | 540 |
| ggacttcccg | gaccccccgg | accccccgga | cctcccggac | cccctggcct | cggaggaaac | 600 |
| tttgctcccc | agctgtctta | tggctatgat | gagaaatcaa | ccggaggaat | ttccgtgcct | 660 |
| ggccccatgg | gtccctctgg | tcctcgtggt | ctccctggcc | cccctggtgc | acctggtccc | 720 |
| caaggcttcc | aaggtccccc | tggtgagcct | ggcgagcctg | gagcttcagg | tcccatgggt | 780 |
| ccccgaggtc | ccccaggtcc | ccctggaaag | aatggagatg | atgggggaagc | tggaaaacct | 840 |
| ggtcgtcctg | gtgagcgtgg | gcctcctggg | cctcagggtg | ctcgaggatt | gcccggaaca | 900 |
| gctggcctcc | ctggaatgaa | gggacacaga | ggtttcagtg | gtttgatgg | tgccaaggga | 960 |
| gatgctggtc | ctgctggtcc | taagggtgag | cctggcagcc | tggtgaaaa | tggagctcct | 1020 |
| ggtcagatgg | gccccgtgg | cctgcctggt | gagagaggtc | gccctggagc | cctggccct | 1080 |
| gctggtgctc | gtggaaatga | tggtgctact | ggtgctgccg | ggcccctgg | tccaccggc | 1140 |
| cccgctggtc | ctcctggctt | ccctggtgct | gttggtgcta | agggtgaagc | tggtcccaa | 1200 |
| gggccccgag | gctctgaagg | tccccaggt | gtgcgtggtg | agcctggccc | cctggccct | 1260 |
| gctggtgctg | ctggccctgc | tggaaaccct | ggtgctgatg | gacagcctgg | tgctaaaggt | 1320 |
| gccaatggtg | ctcctggtat | tgctggtgct | cctggcttcc | ctggtgcccg | aggcccctct | 1380 |
| ggaccccagg | gccccggcgg | ccctcctggt | cccaagggta | acagcggtga | acctggtgct | 1440 |
| cctggcagca | aaggagacac | tggtgctaag | ggagagcctg | ccctgttgg | tgttcaagga | 1500 |
| ccccctggcc | ctgctggaga | ggaaggaaag | cgaggagctc | gaggtgaacc | cggacccact | 1560 |
| ggcctgcccg | gacccctgg | cgagcgtggt | ggacctggta | gcgtggtt | ccctggcgca | 1620 |
| gatggtgttg | ctggtcccaa | gggtcccgct | ggtgaacgtg | gttctcctgg | ccctgctggc | 1680 |

-continued

```
cccaaaggat ctcctggtga agctggtcgt cccggtgaag ctggtctgcc tggtgccaag    1740
ggtctgactg gaagccctgg cagccctggt cctgatggca aaactggccc ccctggtccc    1800
gccggtcaag atggtcgccc cggaccccca ggcccacctg gtgcccgtgg tcaggctggt    1860
gtgatgggat ccctggacct aaaggtgct gctggagagc ccggcaaggc tggagagcga    1920
ggtgttcccg gaccccctgg cgctgtcggt cctgctggca agatggaga ggctggagct    1980
cagggaccc ctggccctgc tggtcccgct ggcgagagag gtgaacaagg ccctgctggc    2040
tcccccggat tccagggtct ccctggtcct gctggtcctc aggtgaagc aggcaaacct    2100
ggtgaacagg gtgttcctgg agaccttggc gcccctggcc cctctggagc aagaggcgag    2160
agaggtttcc ctggcgagcg tggtgtgcaa ggtcccctg gtcctgctgg tccccgaggg    2220
gccaacggtg ctcccggcaa cgatggtgct aagggtgatg ctggtgcccc tggagctccc    2280
ggtagccagg gcgcccctgg ccttcaggga atgcctggta acgtggtgc agctggtctt    2340
ccagggccta aggtgacag aggtgatgct ggtcccaaag gtgctgatgg ctctcctggc    2400
aaagatggcg tccgtggtct gactggcccc attggtcctc ctggccctgc tggtgcccct    2460
ggtgacaagg gtgaaagtgg tcccagcggc cctgctggtc ccactggagc tcgtggtgcc    2520
cccgagacc gtggtgagcc tggtcccccc ggccctgctg gctttgctgg cccccctggt    2580
gctgacggcc aacctggtgc taaaggcgaa cctggtgatg ctggtgctaa aggcgatgct    2640
ggtcccctg gccctgccgg accgctgga ccccctggcc ccattggtaa tgttggtgct    2700
cctggagcca aggtgctcg cggcagcgct ggtcccctg tgctactgg tttccctggt    2760
gctgctggcc gagtcggtcc tcctggcccc tctggaaatg ctggaccccc tggccctcct    2820
ggtcctgctg gcaaagaagg cggcaaaggt ccccgtggtg agactggccc tgctggacgt    2880
cctggtgaag ttggtcccc tggtcccct ggccctgctg gcgagaaagg atcccctggt    2940
gctgatggtc ctgctggtgc tcctggtact cccgggcctc aaggtattgc tggacagcgt    3000
ggtgtggtcg gcctgcctgg tcagagagga gagagaggct tccctggtct tcctggcccc    3060
tctggtgaac ctggcaaaca aggtcccctct ggagcaagtg gtgaacgtgg tccccctggt    3120
cccatgggcc ccctggatt ggctggaccc cctggtgaat ctggacgtga ggggctcct    3180
ggtgccgaag gttccctgg acgagacggt tctcctggcg ccaagggtga ccgtggtgag    3240
accgcccccg ctggaccccc tggtgctcct ggtgctcctg gtgccctggg cccgttggc    3300
cctgctggca agagtggtga tcgtggtgag actggtcctg ctggtccccg cggtcctgtc    3360
ggccctgttg gcgcccgtgg ccccgccgga ccccaaggcc ccgtggtga caagggtgag    3420
acaggcgaac agggcgacag aggcataaag gtcaccgtg gcttctctgg cctccagggt    3480
ccccctggcc ctcctggctc tcctggtgaa caaggtccct ctggagcctc tggtcctgct    3540
ggtcccgag gtcccctgg ctctgctggt gctcctggca agatggact caacggtctc    3600
cctgcccca ttgggccccc tggtcctcgc ggtcgcactg gtgatgctgg tcctgttggt    3660
ccccccggcc ctcctggacc tcctggtccc ctggtcctc ccagcgctgg tttcgacttc    3720
agcttcctgc cccagccacc tcaagagaag gctcacgatg gtggccgcta ctacggggct    3780
gatgatgcca atgtggttcg tgaccgtgac ctcgaggtgg acaccaccct caagagcctg    3840
agccagcaga tcgagaacat ccggagccca gagggcagcc gcaagaaccc gcccgcacc    3900
tgccgtgacc tcaagatgtg ccactctgac tggaagagtg gagagtactg gattgacccc    3960
aaccaaggct gcaacctgga tgccatcaaa gtcttctgca acatggagac tggtgagacc    4020
tgccgtgtacc ccactcagcc cagtgtggcc cagaagaact ggtacatcag caagaacccc    4080
```

```
aaggacaaga ggcatgtctg gttcggcgag agcatgaccg atggattcca gttcgagtat    4140
ggcggccagg gctccgaccc tgccgatgtg gccatccagc tgaccttcct gcgcctgatg    4200
tccaccgagg cctcccagaa catcacctac cactgcaaga acagcgtggc ctacatggac    4260
cagcagactg gcaacctcaa gaaggccctg ctcctccagg gctccaacga gatcgagatc    4320
cgcgccgagg gcaacagccg cttcacctac agcgtcactg tcgatggctg cacgagtcac    4380 accgagcct ggggcaagac agtgattgaa tacaaaacca ccaagacctc ccgcctgccc     4440
atcatcgatg tggcccccctt ggacgttggt gccccagacc aggaattcgg cttcgacgtt    4500
ggccctgtct gcttcctgta aactccctcc atcccaacct ggctccctcc cacccaacca    4560 acttccccc caacccggaa acagacaagc aacccaaact gaaccccctc aaaagccaaa     4620
aaatgggaga caatttcaca tggactttgg aaaatatttt tttcctttgc attcatctct    4680
caaacttagt ttttatcttt gaccaaccga acatgaccaa aaaccaaaag tgcattcaac    4740
cttaccaaaa aaaaaaaaaa aaaagaata aataataac ttttaaaaa aggaagcttg       4800 gtccacttgc ttgaagaccc atgcgggggt aagtccctt ctgcccgttg ggcttatgaa     4860
accccaatgc tgccctttct gctccttct ccacaccccc cttggggcct cccctccact     4920
ccttcccaaa tctgtctccc cagaagacac aggaaacaat gtattgtctg cccagcaatc    4980
aaaggcaatg ctcaaacacc caagtggccc ccaccctcag cccgctcctg cccgcccagc    5040 accccaggc cctgggggac ctggggttct cagactgcca agaagccctt gccatctggc      5100
gctcccatgg ctcttgcaac atctccccctt cgttttgag ggggtcatgc cggggggagcc    5160 accagcccct cactgggttc ggaggagagt caggaagggc cacgacaaag cagaaacatc    5220
ggatttgggg aacgcgtgtc aatcccttgt gccgcagggc tggcgggag agactgttct     5280 gttccttgtg taactgtgtt gctgaaagac tacctcgttc ttgtcttgat gtgtcaccgg    5340
ggcaactgcc tgggggcggg gatgggggca gggtggaagc ggctccccat tttataccaa    5400
aggtgctaca tctatgtgat gggtgggggtg gggagggaat cactggtgct atagaaattg    5460
agatgccccc ccaggccagc aaatgttcct ttttgttcaa agtctatttt tattccttga    5520
tatttttctt ttttttttttt tttttttgtg gatgggact tgtgaatttt tctaaaggtg    5580
ctatttaaca tgggaggaga gcgtgtgcgg ctccagccca gcccgctgct cactttccac    5640
cctctctcca cctgcctctg gcttctcagg cctctgctct ccgacctctc tcctctgaaa    5700
ccctcctcca cagctgcagc ccatcctccc ggctccctcc tagtctgtcc tgcgtcctct    5760
gtccccgggt tcagagaca acttcccaaa gcacaaagca gttttccccc ctaggggtgg    5820
gaggaagcaa aagactctgt acctatttg tatgtgtata ataatttgag atgttttttaa   5880 ttattttgat tgctggaata aagcatgtgg aaatgaccca aacataa                  5927
```

<210> SEQ ID NO 8
<211> LENGTH: 5411
<212> TYPE: DNA
<213> ORGANISM: Homo sapiens

<400> SEQUENCE: 8

```
gtgtcccata gtgtttccaa acttggaaag ggcgggggag ggcgggagga tgcggagggc      60
ggaggtatgc agacaacgag tcagagtttc cccttgaaag cctcaaaagt gtccacgtcc    120
tcaaaaagaa tggaaccaat ttaagaagcc agccccgtgg ccacgtccct tcccccattc    180
gctccctcct ctgcgccccc gcaggctcct cccagctgtg gctgcccggg cccccagccc    240
```

```
cagccctccc attggtggag gcccttttgg aggcacccta gggccaggga aacttttgcc      300
gtataaatag ggcagatccg ggctttatta ttttagcacc acggcagcag gaggtttcgg      360
ctaagttgga ggtactggcc acgactgcat gcccgcgccc gccaggtgat acctccgccg      420
gtgacccagg ggctctgcga cacaaggagt ctgcatgtct aagtgctaga catgctcagc      480
tttgtggata cgcggacttt gttgctgctt gcagtaacct tatgcctagc aacatgccaa      540
tctttacaag aggaaactgt aagaaagggc ccagccggag atagaggacc acgtggagaa      600
aggggtccac caggccccc  aggcagagat ggtgaagatg gtcccacagg ccctcctggt      660
ccacctggtc ctcctggccc ccctggtctc ggtgggaact ttgctgctca gtatgatgga      720
aaaggagttg gacttggccc tggaccaatg ggcttaatgg gacctagagg cccacctggt      780
gcagctggag ccccaggccc tcaaggtttc caaggacctg ctggtgagcc tggtgaacct      840
ggtcaaactg gtcctgcagg tgctcgtggt ccagctggcc ctcctggcaa ggctggtgaa      900
gatggtcacc ctggaaaacc cggacgacct ggtgagagag gagttgttgg accacagggt      960
gctcgtggtt ccctggaac tcctggactt cctggcttca aaggcattag ggacacaat     1020 ggtctggatg gattgaaggg acagcccggt gctcctggtg tgaagggtga acctggtgcc     1080
cctggtgaaa atggaactcc aggtcaaaca ggagcccgtg ggcttcctgg tgagagagga     1140
cgtgttggtg ccctggccc  agctggtgcc cgtggcagtg atggaagtgt gggtcccgtg     1200
ggtcctgctg gtcccattgg gtctgctggc cctccaggct tcccaggtgc ccctggcccc     1260
aagggtgaaa ttggagctgt tggtaacgct ggtcctgctg gtcccgccgg tccccgtggt     1320
gaagtgggtc ttccaggcct ctccggcccc gttggacctc tggtaatcc  tggagcaaac     1380 ggccttactg gtgccaaggg tgctgctggc cttcccggcg ttgctggggc tcccggcctc     1440
cctggacccc gcggtattcc tggccctgtt ggtgctgccg gtgctactgg tgccagagga     1500
cttgttggtg agcctggtcc agctggctcc aaaggagaga gcggtaacaa gggtgagccc     1560
ggctctgctg ggccccaagg tcctcctggt cccagtggtg aagaaggaaa gagaggccct     1620
aatggggaag ctggatctgc cggccctcca ggacctcctg ggctgagagg tagtcctggt     1680
tctcgtggtc ttcctggagc tgatggcaga gctggcgtca tgggccctcc tggtagtcgt     1740
ggtgcaagtg gccctgctgg agtccgagga cctaatggag atgctggtcg ccctggggag     1800
cctggtctca tggacccag  aggtcttcct ggttcccctg gaaatatcgg ccccgctgga     1860
aaagaaggtc ctgtcggcct ccctggcatc gacggcaggc ctggcccaat ggcccagct     1920 ggagcaagag gagagcctgg caacattgga ttccctggac ccaaaggccc cactggtgat     1980
cctggcaaaa acggtgataa aggtcatgct ggtcttgctg gtgctcgggg tgctccaggt     2040
cctgatggaa acaatggtgc tcagggacct cctggaccac aggtgttcaa ggtggaaaa     2100 ggtgaacagg gtccccctgg tcctccaggc ttcagggtc  tgcctggccc ctcaggtccc     2160
gctggtgaag ttggcaaacc aggagaaagg ggtctccatg gtgagtttgg tctccctggt     2220
cctgctggtc aagaggggga acgcggtccc cagggtgaga gtggtgctgc ggtcctact      2280 ggtcctattg gaagccgagg tccttctgga ccccagggc  tgatggaaa  caagggtgaa     2340 cctggtgtg  ttggtgctgt gggcactgct ggtccatctg gtcctagtgg actcccagga     2400 gagagggtg  ctgctggcat acctggaggc aagggagaaa aggtgaacc  tggtctcaga     2460 ggtgaaattg gtaaccctgg cagagatggt gctcgtggtg ctcctggtgc tgtaggtgcc     2520
cctggtcctg ctggagccac aggtgaccgg ggcgaagctg gggctgctgg tcctgctggt     2580
cctgctggtc ctcggggaag ccctggtgaa cgtggtgagg tcggtcctgc tggccccaat     2640
```

```
ggatttgctg gtcctgctgg tgctgctggt caacctggtg ctaaaggaga aagaggagcc   2700
aaagggccta agggtgaaaa cggtgttgtt ggtcccacag gccccgttgg agctgctggc   2760
ccagctggtc caaatggtcc ccccggtcct gctggaagtc gtggtgatgg aggccccccct  2820 ggtatgactg gtttccctgg tgctgctgga cggactggtc ccccaggacc ctctggtatt   2880
tctggccctc ctggtccccc tggtcctgct gggaagaag gcttcgtgg tcctcgtggt      2940 gaccaaggtc cagttggccg aactggagaa gtaggtgcag ttggtccccc tggcttcgct   3000
ggtgagaagg gtccctctgg agaggctggt actgctggac ctcctggcac tccaggtcct   3060
cagggtcttc ttggtgctcc tggtattctg ggtctccctg gctcgagagg tgaacgtggt   3120
ctaccaggtg ttgctggtgc tgtgggtgaa cctggtcctc ttggcattgc cggccctcct   3180
gggccccgtg gtcctcctgg tgctgtgggt agtcctggag tcaacggtgc tcctggtgaa   3240
gctggtcgtg atggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aaggggccca gaggtcttcc tggcttaaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtaca gttggacctg ctggcattcg aggccctcag   3720
ggtcaccaag gccctgctgg cccccctggt ccccctggcc ctcctggacc tccaggtgta   3780
agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agaccttct tactcctgaa ggctctagaa agaacccagc tcgcacatgc   3960
cgtgacttga gactcagcca cccagagtgg agcagtggtt actactggat tgaccctaac   4020
caaggatgca ctatgatgc tatcaaagta tactgtgatt tctctactgg cgaaacctgt   4080
atccgggccc aacctgaaaa catcccagcc aagaactggt ataggagctc caaggacaag   4140 aaaacacgtct ggctaggaga aactatcaat gctggcagcc agtttgaata taatgtagaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac caggaattct tgtggacat tggcccagtc   4560 tgtttcaaat aaatgaactc aatctaaatt aaaaagaaa gaatttgaa aaactttct    4620 ctttgccatt tcttcttctt cttttttaac tgaaagctga atccttccat ttcttctgca   4680
catctacttg cttaaattgt gggcaaaaga gaaaagaag gattgatcag agcattgtgc   4740
aatacagttt cattaactcc ttcccccgct cccccaaaaa tttgaattt ttttcaaca   4800 ctcttacacc tgttatggaa aatgtcaacc tttgtaagaa aaccaaaata aaaattgaaa   4860
aataaaaacc ataaacattt gcaccacttg tggcttttga atatcttcca cagagggaag   4920
tttaaaaccc aaacttccaa aggtttaaac tacctcaaaa cactttccca tgagtgtgat   4980
```

| | |
|---|---|
| ccacattgtt aggtgctgac ctagacagag atgaactgag gtccttgttt tgttttgttc | 5040 |
| ataatacaaa ggtgctaatt aatagtattt cagatacttg aagaatgttg atggtgctag | 5100 |
| aagaatttga gaagaaatac tcctgtattg agttgtatcg tgtggtgtat ttttaaaaa | 5160 |
| atttgattta gcattcatat tttccatctt attcccaatt aaaagtatgc agattatttg | 5220 |
| cccaaatctt cttcagattc agcatttgtt ctttgccagt ctcattttca tcttcttcca | 5280 |
| tggttccaca gaagctttgt ttcttgggca agcagaaaaa ttaaattgta cctattttgt | 5340 |
| atatgtgaga tgtttaaata aattgtgaaa aaatgaaat aaagcatgtt tggttttcca | 5400 |
| aaagaacata t | 5411 |

<210> SEQ ID NO 9
<211> LENGTH: 4467
<212> TYPE: DNA
<213> ORGANISM: Homo sapiens

<400> SEQUENCE: 9

| | |
|---|---|
| atggctcacg ctcgtgttct cctcctcgct ctcgctgttt tggcaacagc tgctgtggct | 60 |
| gtggcttcta gttcttcttt tgctgattca aaccctatta gacctgttac tgatagagca | 120 |
| gcttccactt tggctcaatt gcaagaggag ggccaggttg agggcaagaa tgaggatatc | 180 |
| cctccaatta catgcgtgca aaatggcttg cgttaccacg atagggatgt gtggaaacct | 240 |
| gaaccttgtc gtatctgtgt gtgtgataac ggcaaggtgc tctgcgatga tgttatctgc | 300 |
| gatgagacaa aaaattgccc tggcgctgaa gttcctgagg gcgagtgttg ccctgtgtgc | 360 |
| cctgatggtt ccgagtcccc aactgatcag gaaaactactg gcgtggaggg cccaaaagga | 420 |
| gatactggtc cacgtggtcc taggggtcca gcaggtcctc caggtagaga tggtattcca | 480 |
| ggccagcctg gattgccagg accaccaggc ccacctggcc caccaggacc tcctggtctt | 540 |
| ggtggaaatt tcgctccaca actctcttat ggctatgatg agaagtcaac aggtggtatt | 600 |
| tccgttccag gtcctatggg accatccgga ccaagaggtc tcccaggtcc tcaggtgct | 660 |
| cctggacctc aaggcttttca aggacctcca ggcgaaccag agaaccaggc gcttctgga | 720 |
| ccaatgggcc caaggggacc acctggccca ccaggaaaaaa atggcgatga tggcgaagct | 780 |
| ggaaagcctg gtcgtcctgg agagagaggt cctcctggcc cacagggtgc aagaggcttg | 840 |
| ccaggaactc ctggcttgcc tggaatgaag ggacataggg gcttctccgg cctcgatggc | 900 |
| gctaagggtg atgctggccc tgctggacca aagggcgagc caggttcccc tggagaaaac | 960 |
| ggtgctcctg gacaaatggg tcctcgtgga cttccaggag aaaggggtcg tccaggcgct | 1020 |
| ccaggaccag caggtgctag gggaaacgat ggtgcaacag gcgctgctgg ccctcctggc | 1080 |
| ccaactggtc ctgctggccc tccaggattc ccaggcgcag ttggagctaa aggaagcagca | 1140 |
| ggaccacagg gccctagggg ttctgaagga cctcagggtg ttagaggtga accaggtcct | 1200 |
| ccaggcccag ctggagcagc tggtccagca ggaaatccag gtgctgatgg tcaacctgga | 1260 |
| gctaagggcg ctaatggcgc accaggtatc gcaggcgcac caggttttcc tggcgctaga | 1320 |
| ggcccaagtg gtcctcaagg accaggtgga ccaccaggtc caaaaggcaa ttctggcgaa | 1380 |
| cctggcgctc caggttctaa aggagatact ggtgctaaag gcgaaccagg acctgttggt | 1440 |
| gttcagggtc ctcctggtcc tgctggagaa gaggaaaaa gaggtgctcg tggagaacca | 1500 |
| ggaccaactg gacttcctgg acctcctggt gaacgtggcg gacctggctc aaggggtttc | 1560 |
| cctggagctc atggagtggc aggtccaaaa ggccctgctg agagagagg ttcaccaggt | 1620 |
| ccagctggtc ctaagggctc ccctggtgaa gcaggtagac caggcgaagc aggattgcca | 1680 |

```
ggcgcaaagg gattgacagg ctctcctggt agtcctggcc cagatggaaa aacaggccca    1740
ccaggtccag caggacaaga tggacgtcca ggcccaccag gtcctcctgg agcaaggggn    1800
caagctggcg ttatgggttt tccaggacct aaaggtgctg ctggagagcc aggaaaggca    1860
ggtgaaagag gagttcctgg tccaccagga gcagtgggtc ctgctggcaa agatggtgaa    1920
gctggagcac agggccctcc aggccctgct ggcccagctg gcgaacgtgg agaacaaggc    1980
ccagctggta gtccaggatt tcaaggattg cctggccctg ctggccctcc aggagaagca    2040
ggaaaacctg gagaacaagg agttcctggt gatttgggag cacctggacc ttcaggagca    2100
cgtggtgaaa gaggcttccc tggcgagagg ggtgttcaag gtccaccagg tccagcagga    2160
cctagaggtg ctaatggcgc tcctggcaac gatggagcaa aggtgatgc tggtgctcct    2220 ggcgcacctg gaagtcaggg tgctcctgga ttgcaaggaa tgcctggaga gggggtgct    2280 gctggcttgc caggcccaaa gggcgatagg ggtgatgctg accaaaagg tgctgatgga    2340 tccccaggaa aagatggagt tcgtggtctt actggcccaa tcggacctcc aggccctgct    2400
ggcgctccag gtgataaggg cgaaagtggc ccaagtggac ctgctggacc tactggtgct    2460
agaggtgcac ctggtgatag gggtgaacct ggaccacctg gtccagctgg ttttgctggt    2520
cctcctggag ctgatggaca acctggcgca aagggtgaac caggtgatgc tggcgcaaag    2580
ggagatgctg gtccacctgg acctgctggt ccagcaggcc ccctgggcc aatcggtaat    2640 gttggagcac aggtgctaa gggagctagg ggttccgctg gtccacctgg agcaacagga    2700
tttccaggcg ctgctggtag agttggccca ccaggcccat ccggaaacgc aggccctcct    2760
ggtcctccag gtcctgctgg caaggagggt ggcaaaggac caggggcga aactggcct    2820 gctggtagac ctggcgaagt tggcctct ggaccaccag gtccagcagg agaaaaaggt    2880
tccccaggag ctgatggccc agctggtgct ccaggaactc caggccctca aggtattgct    2940
ggacagagag gcgttgtggg actccctggt caaaggggag agagaggatt ccaggcttg    3000 ccaggaccta gtggagaacc tggaaaacaa ggcccatcag gcgctagtgg agagcgtgga    3060
cctcctggcc ctatgggacc tcctggattg ctggcccac ctggcgaatc aggtcgtgaa    3120
ggcgcaccag gcgcagaagg atcacctgga agagatggat cccctggtgc taaaggcgat    3180
cgtggagaaa ctggtccagc aggcccacca ggcgcaccag gtgcacctgg cgctccagga    3240
cctgtgggac cagctggaaa atccggagat aggggcgaga caggcccagc aggaccagct    3300
ggacctgttg gcctgctgg cgctcgtgga ccagcaggac ctcaaggacc aaggggagat    3360
aagggagaaa caggcgaaca aggcgatagg ggcattaagg gtcatagggg ttttagtggc    3420
ctccagggtc ctcctggccc acctggatca ccaggagaac agggaccatc tggtgcttcc    3480
ggcccagctg gtcaagagg acctccagga tcagctggtg cacctggaaa agatggtctt    3540
aacggtctcc caggaccaat cggccctcca ggacctagag aagaacagg agatgctggc    3600 cctgttggcc ctcaggacc tcctggtcca ccagtccac ctggtcctcc atcagctgga    3660
ttcgattttt catttcttcc acagccacca caagagaaag ctcacgatgg cggcagatat    3720
taccgtgctg atgatgctaa cgttgttagg gatagagatt tggaagtgga tacaactttg    3780
aaatccctct cccagcaaat tgaaaacatt agatctccag aaggttcacg taaaaaccca    3840
gctagaacat gtcgtgattt gaaaatgtgt cactccgatt ggaaaagtgg tgaatactgg    3900
attgatccaa atcagggctg taatctcgat gctatcaaag tttttctgtaa catgaaaca    3960 ggcgaaacat gcgtttatcc tactcaacct tccgtggctc agaaaaattg gtacatctca    4020
```

| | |
|---|---|
| aaaaatccta aagataagag gcacgtttgg ttcggtgaaa gtatgactga tggatttcaa | 4080 |
| tttgagtacg gcggtcaagg tagtgatcca gctgatgtgg ctattcaact cacatttttg | 4140 |
| cgtcttatgt ccacagaggc atcacaaaac atcacttacc actgcaaaaa cagtgtggct | 4200 |
| tatatggatc aacaaacagg aaaccttaag aaggctcttc ttttgaaggg ctcaaacgag | 4260 |
| attgagatta gagcagaggg caactcaagg tttacttatt cagttactgt tgatggctgc | 4320 |
| acttcacata ctggcgcttg gggtaaaaca gttatcgagt ataagactac aaaaacatca | 4380 |
| agactcccaa tcattgatgt tgctcctctc gatgttggcg ctcctgatca agagttcggt | 4440 |
| tttgatgtgg gcccagtttg tttcctc | 4467 |

<210> SEQ ID NO 10
<211> LENGTH: 4167
<212> TYPE: DNA
<213> ORGANISM: Homo sapiens

<400> SEQUENCE: 10

| | |
|---|---|
| atggctcacg ctcgtgttct cctcctcgct ctcgctgttt tggcaacagc tgctgtggct | 60 |
| gtggcttcaa gttctagttt tgctgattcc aacccaattc gtccagttac tgatagagca | 120 |
| gcttccactt tggctcaatt gcttcaagaa gaaactgtga ggaagggccc tgctggcgat | 180 |
| aggggcccta ggggcgaaag gggtccacca ggacctccag gcagggatgg cgaagatggt | 240 |
| ccaactggcc ctcctggacc tcctggccct ccagggccac ccggcttggg cggaaacttc | 300 |
| gcagctcaat acgatggcaa gggtgttggt cttggtcctg gtcctatggg cttgatggga | 360 |
| cctagaggcc cacctggtgc tgctggtgct cctggaccac agggttttca gggaccagct | 420 |
| ggcgagccag gagagccagg ccaaacagga ccagctggtg caaggggacc tgctggacct | 480 |
| cctgaaaaag ctggtgaaga tggtcaccca ggcaaaccag gacgtcctgg cgaaagaggt | 540 |
| gttgttggac acaaggcgc tagggga ttt ccaggtacac ctggattgcc aggttttaag | 600 |
| ggcattcgtg gtcataacgg cctcgatgga ttgaagggac agcctggcgc acctggcgtt | 660 |
| aagggtgaac tggagcacc aggtgaaaac ggtactcctg ccagactgg tgcaagagga | 720 |
| ctcccaggtg aaaggggtag agttggtgct cctggacctg ctggagctag gggtagtgat | 780 |
| ggtagtgttg gtcctgtggg ccctgctggt ccaatcggtt ccgctggccc acctggattc | 840 |
| ccaggcgctc caggacctaa aggagaaatc ggtgctgtgg gtaacgcagg tcctactggt | 900 |
| ccagcaggtc tcgtggaga gtgggattg ccaggacttt ctggtccagt gggccctcca | 960 |
| ggcaaccctg gagctaacgg cttgacagga gctaaaggcg cagcaggact ccctggagtg | 1020 |
| gctggcgcac caggattgcc tggtccaagg ggtatcccag gccctgttgg cgcagctgga | 1080 |
| gctactggtg cacgtggact tgttggcgaa ccaggccctg ctggatcaaa aggcgagtct | 1140 |
| ggaaataagg gagaacctgg ttctgctgga cctcaaggtc ctcctggacc ttctggagaa | 1200 |
| gaaggaaaaa ggggaccaaa tggcgaggct ggatcagcag gtccaccagg accacctgga | 1260 |
| cttcgtggat cccctggtag tagaggactt ccaggcgctg atggtagagc aggcgttatg | 1320 |
| ggaccaccag gaagtagagg agcatccggt ccagcaggag ttagggtcc taacggagat | 1380 |
| gctggtagac aggtgaacc aggtcttatg ggcccaaggg gcctcccagg tagtccagga | 1440 |
| aatatcggcc ctgctggaaa agaaggccct gttggacttc aggtattga tggacgtcct | 1500 |
| ggccctattg gccagcagg tgcaagagga gaacctggca atattggatt ccaggacca | 1560 |
| aagggtccaa caggcgatcc tggaaaaaat ggagataagg gtcatgctgg attggcaggc | 1620 |
| gcaaggggcg ctcctggtcc agatggaaac aacggcgcac agggtccacc tggccctcag | 1680 |

```
ggtgttcaag gcggaaaagg cgaacaaggc ccagctggac caccaggctt tcaaggcttg    1740
ccaggaccaa gtggtccagc aggtgaagtt ggcaagccag gcgagcgtgg acttcatggc    1800
gagtttggac tccctggacc agcaggacca aggggtgaaa gaggccctcc tggagagagt    1860
ggcgctgctg gaccaacagg cccaatcggt agtagaggtc ctagtggacc tccaggccca    1920
gatggaaata agggtgaacc aggagttgtg ggcgctgttg gaacagctgg tccttcagga    1980
ccatcaggac tcccaggcga gagaggcgct gctggcattc ctggaggaaa aggtgaaaaa    2040
ggcgaacctg gcctccgtgg cgaaatcgga atcctggacg tgatggtgc tcgtggtgca    2100 cacggcgctg tgggcgctcc aggccctgct ggtgctactg gtgatagagg agaggctggc    2160
gcagctggcc cagcaggtcc tgctggccca aggggtagtc ctggtgaaag aggcgaagtt    2220
ggacctgctg gccctaacgg ctttgctggc cctgctggag cagcaggtca acctggcgct    2280
aaaggtgaaa ggggcggaaa gggcccaaaa ggtgaaaatg gcgttgtggg accaactggt    2340
ccagtgggcg cagctggacc tgctggtcca aatggaccac caggaccagc aggtagtaga    2400
ggagatggtg gacctccagg aatgacaggt tttccaggtg ctgctggtag aacaggacct    2460
cctggtccta gtggtatttc tggtccacca ggaccaccag gtcctgctgg aaaagaagga    2520
ttgaggggtc cacgtggtga tcaaggacca gtgggcagaa ctggtgaagt tggcgcagtg    2580
ggaccacctg gttttgctgg agaaaagggc ccttctggag aggcaggaac agctggtcct    2640
cctggtacac ctggacctca aggactttg gtgcacctg gtattctcgg attgccagga    2700
agtaggggcg aacgtggact tcctggcgtg caggagcag ttggagaacc tggccctctc    2760
ggaatcgcag gcccaccagg cgcaagagga ccaccaggag ctgttggatc accaggcgtg    2820
aatggtgcac ctggcgaggc tggtcgtgat ggaaacccag gaaatgatgg cccaccagga    2880
agagatggtc aacctggaca caaggcgag aggggctacc caggaaatat tggcccagtt    2940
ggtgctgctg gcgcaccagg cccacacggt ccagttggac cagcaggaaa acacggtaat    3000
cgtggcgaaa caggcccttc aggcccagtg ggacctgctg gtgctgttgg cccaagagga    3060
ccatctggac ctcaaggcat tagaggcgat aagggagagc ctggcgaaaa aggacctaga    3120
ggcttgcctg gtttaaagg acacaacggt ctccaaggac ttccaggtat cgctggtcat    3180
catggagatc agggtgctcc tggatcagtg ggtccagcag gtcctagagg cccagcaggc    3240
ccttccggtc cagcaggaaa ggatggacgt actggccacc ctggaactgt gggccctgct    3300
ggaattagag gtcctcaagg tcatcagggc cctgctggcc ctccaggtcc accaggtcct    3360
ccaggcccac caggagtttc agtggtggt tacgattttg gttacgatgg tgatttttac    3420
cgtgctgatc aacctagaag tgctccttct ctccgtccta agattatga agttgatgct    3480 actttgaaat cacttaacaa ccagattgag actcttctca cacctgaggg atcaagaaag    3540
aatccagcac gtacatgccg tgatctcaga cttagtcacc cagagtggtc aagtggctat    3600
tattggattg atcctaatca gggttgtaca atggaggcta tcaaagttta ctgtgatttt    3660
ccaactggag agacatgtat tagggcacaa cctgagaaca ttccagctaa aaattggtat    3720
cgttcctcta agataagaa acatgtttgg ctcggagaga ctattaacgc tggttctcag    3780
ttcgagtata atgttgaggg cgttacttct aaagagatgg caactcagct cgcttttatg    3840
agattgctcg ctaactacgc atcccaaaac atcacttatc actgcaaaaa ttccattgca    3900
tatatggatg aggagacagg aaatttgaag aaagcagtta ttctccaagg tagtaacgat    3960
gttgagcttg tggctgaggg aaatagtaga ttcacttaca cagtttttgt ggatggatgc    4020
```

```
tcaaagaaaa ctaatgagtg gggcaagaca atcattgagt acaagacaaa taagccttct    4080
aggctcccat ttctcgatat tgcacctctt gatatcggag gagctgatca cgagtttttt    4140
gttgatatcg gacctgtttg ttttaag                                        4167
```

<210> SEQ ID NO 11
<211> LENGTH: 1633
<212> TYPE: DNA
<213> ORGANISM: Artificial sequence
<220> FEATURE:
<223> OTHER INFORMATION: Synthetic sequence containing the coding
   regions of the vascular signal sequence of barley gene for Thiol
   protease aleurain precursor fused to the human Prolyl
   4-hydroxylase beta subunit and flanking regions

<400> SEQUENCE: 11

```
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg     120
actgatagag ctgcttctac tcttgctcaa ttggtcgaca tggatgctcc agaagaggag     180
gatcacgttc ttgtgcttag aagtctaac ttcgctgaag ctcttgctgc tcacaagtac      240
cttcttgtgg agttttatgc tccttggtgc ggacattgca aagctcttgc tccagagtat     300
gctaaggctg ctggaaagtt gaaggctgag ggatctgaaa ttaggcttgc taaagtggat     360
gctactgagc agtctgatct tgctcaacag tacggagtta ggggataccc aactattaag     420
ttcttcagga acggagatac tgcttctcca aaggagtata ctgctggaag ggaggctgat     480
gatattgtga actggcttaa gagagaact ggaccagctg ctactactct tccagatgga     540
gctgctgctg aatctcttgt ggagtcatct gaggtggcag tgattggatt cttcaaggat     600
gtggagtctg attctgctaa gcagttcctt caagctgctg aggctattga tgatattcca     660
ttcggaatta cttctaactc tgatgtgttc tctaagtacc agcttgataa ggatggagtg     720
gtgcttttca gaaaattcga tgagggaagg aacaatttcg agggagaggt gacaaaggag     780
aaccttcttg atttcattaa gcacaaccag cttccacttg tgattgagtt cactgagcag     840
actgctccaa agattttcgg aggagagatt aagactcaca ttcttctttt ccttccaaag     900
tctgtgtctg attacgatgg aaaagttgtct aacttcaaga ctgctgctga gtcttcaag    960 ggaaagattc ttttcatttt cattgattct gatcacactg ataaccagag gattcttgag    1020
ttcttcggac ttaagaagga gagtgccca gctgttaggc ttattactct tgaggaggag    1080
atgactaagt acaagccaga gtctgaagaa cttactgctg agaggattac tgagttctgc    1140
cacagattcc ttgagggaaa gattaagcca caccttatgt ctcaagagct tccagaggat    1200
tgggataagc agccagttaa ggtgttggtg gtaaaaact tcgaggatgt ggcttctcgat    1260 gagaagaaga acgtgttcgt ggagttctac gcaccttggt gtggtcactg taagcagctt    1320
gctccaattt gggataagtt gggagagact acaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca gaagttcct tgagtctgga ggacaagatg gagctggaga tgatgatgat    1560
cttgaggatt tggaagaagc tgaggagcca gatatggagg aggatgatga tcagaaggct    1620
gtgtgatgag ctc                                                       1633
```

<210> SEQ ID NO 12
<211> LENGTH: 1723
<212> TYPE: DNA

<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Prolyl
      4-hydroxylase alpha-1 subunit and flanking regions

<400> SEQUENCE: 12

```
ctcgagtaaa ccatggctca tgctagggtt ttgcttttgg ctcttgctgt tcttgctact      60
gctgctgttg ctgtggcttc ttcttcatct ttcgctgatt ctaacccaat taggccagtg     120
actgatagag ctgcttctac tcttgctcaa ttggtcgaca tgcacccagg attcttcact     180
tctattggac agatgactga tcttattcac actgagaagg atcttgtgac ttctcttaag     240
gattacatta aggctgagga ggataagttg gagcagatta agaagtgggc tgagaagttg     300
gataggctta cttctactgc tacaaaagat ccagagggat tcgttggtca tccagtgaac     360
gctttcaagt tgatgaagag gcttaacact gagtggagtg agcttgagaa ccttgtgctt     420
aaggatatgt ctgatggatt catttctaac cttactattc agaggcagta cttcccaaat     480
gatgaggatc aagtgggagc tgctaaggct cttcttaggc ttcaggatac ttacaacctt     540
gatactgata caatttctaa gggaaacctt ccaggagtta agcacaagtc tttccttact     600
gctgaggatt gcttcgagct tggaaaggtt gcatacactg aggctgatta ctaccacact     660
gagctttgga tggaacaagc tcttaggcaa cttgatgagg gagagatttc tactattgat     720
aaggtgtcag tgcttgatta cctttcttac gctgtgtacc agcagggtga tcttgataag     780
gctcttttgc ttactaagaa gttgcttgag cttgatccag aacatcagag ggctaacgga     840
aaccttaagt acttcgagta cattatggct aaggaaaagg atgtgaacaa gtctgcttct     900
gatgatcagt ctgatcaaaa gactactcca aagaagaagg gagtggctgt tgattatctt     960
cctgagaggc agaagtatga gatgttgtgt aggggagagg gtattaagat gactccaagg    1020
aggcagaaga agttgttctg caggtatcac gatggaaaca ggaacccaaa gttcattctt    1080
gctccagcta agcaagaaga tgagtgggat aagccaagga ttattaggtt ccacgatatt    1140
atttctgatg ctgagattga gattgtgaag gatcttgcta agccaagact taggagggct    1200
actatttcta accctattac tggtgatctt gagactgtgc actacaggat ttctaagtct    1260
gcttggcttt ctggatacga gaacccagtg gtgtctagga ttaacatgag gattcaggat    1320
cttactggac ttgatgtgtc tactgctgag gagcttcaag ttgctaacta cggagttgga    1380
ggacaatatg agccacactt cgatttcgct aggaaggatg agccagatgc ttttaaggag    1440
cttggaactg gaaacaggat tgctacttgg cttttctaca tgtctgatgt ttctgctgga    1500
ggagctactg ttttcccaga agtgggagct tctgtttggc caaagaaggg aactgctgtg    1560
ttctggtaca acctttcgc  ttctggagag ggagattact ctactaggca tgctgcttgc    1620
ccagttcttg ttggaaacaa gtgggtgtca aacaagtggc ttcatgagag gggacaagag    1680
tttagaaggc catgcactct ttctgagctt gagtgatgag ctc                      1723
```

<210> SEQ ID NO 13
<211> LENGTH: 2888
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Lysyl hydroxylase 3
      and flanking regions

<400> SEQUENCE: 13

-continued

```
gcgaattcgc tagctatcac tgaaaagaca gcaagacaat ggtgtctcga tgcaccagaa      60
ccacatcttt gcagcagatg tgaagcagcc agagtggtcc acaagacgca ctcagaaaag     120
gcatcttcta ccgacacaga aaaagacaac cacagctcat catccaacat gtagactgtc     180
gttatgcgtc ggctgaagat aagactgacc ccaggccagc actaaagaag aaataatgca     240
agtggtccta gctccacttt agctttaata attatgtttc attattattc tctgcttttg     300
ctctctatat aaagagcttg tattttcatt tgaaggcaga ggcgaacaca cacacagaac     360
ctccctgctt acaaaccaga tcttaaacca tggctcacgc tagggttttg cttcttgctc     420
ttgctgttct tgctactgct gctgttgctg tggcttcttc aagttctttc gctgattcta     480
acccaattag gccagtgact gatagagctg cttctactct tgctcaattg agatctatgt     540
ctgatagacc aaggggaagg gatccagtta atccagagaa gttgcttgtg attactgtgg     600
ctactgctga gactgaagga taccttagat tccttaggag tgctgagttc ttcaactaca     660
ctgtgaggac tcttggactt ggagaagaat ggaggggagg agatgttgct agaactgttg     720
gaggaggaca gaaagtgaga tggcttaaga aagagatgga gaagtacgct gatagggagg     780
atatgattat tatgttcgtg gattcttacg atgtgattct tgctggatct ccaactgagc     840
ttttgaagaa attcgttcag tctggatcta ggcttctttt ctctgctgag tcttttgttt     900
ggccagaatg gggacttgct gagcaatatc cagaagtggg aactgaaaag agattcctta     960
actctggagg attcattgga ttcgctacta ctattcacca gattgtgagg cagtggaagt    1020
acaaggatga cgatgatgat cagcttttct cactaggct ttaccttgat ccaggactta    1080
gggagaagtt gtctcttaac cttgatcaca agtctaggat ttttccagaac cttaacggtg    1140 ctcttgatga ggttgtgctt aagttcgata ggaacagagt gaggattagg aacgtggctt    1200
acgatactct tcctattgtg gtgcatggaa acggaccaac aaaactccag cttaactacc    1260
ttggaaacta cgttccaaac ggatggactc cagaaggagg atgtggattc tgcaatcagg    1320
ataggagaac tcttccagga ggacaaccac caccaagagt ttttccttgct gtgttcgttg    1380 aacagccaac tccattcctt ccaagattcc ttcagaggct tcttcttttg gattacccac    1440
cagatagggt gacactttttc cttcacaaca acgaggtttt ccacgagcca cacattgctg    1500
attcttggcc acagcttcag gatcatttct ctgctgtgaa gttggttggt ccagaagaag    1560
ctctttctcc aggagaagct agggatatgg ctatggattt gtgcaggcag gatccagagt    1620
gcgagttcta cttctctctt gatgctgatg ctgtgcttac taaccttcag actcttagga    1680
ttcttattga ggagaacagg aaagtgattg ctccaatgct ttctaggcac ggaaagttgt    1740
ggtctaattt ctggggtgct cttttctcctg atgagtacta cgctagatca gaggactacg    1800
tggagcttgt tcagagaaag agagtgggag tttggaacgt tccttatatt tctcaggctt    1860
acgtgattag gggagatact cttaggatgg agcttccaca gagggatgtt ttctctggat    1920
ctgatactga tccagatatg gctttctgca agtctttcag ggataaggga attttccttc    1980 accttttctaa ccagcatgag ttcggaagat tgcttgctac ttcaagatac gatactgagc    2040
accttcatcc tgatctttgg cagatttttcg ataacccagt ggattggaag gagcagtaca    2100
ttcacgagaa ctactctagg gctcttgaag gagaaggaat tgtggagcaa ccatgcccag    2160
atgtttactg gttcccactt ctttctgagc aaatgtgcga tgagcttgtt gctgagatgg    2220
agcattacgg acaatggagt ggaggtagac atgaggattc taggcttgct ggaggatacg    2280
agaacgttcc aactgtggat attcacatga agcaagtggg atacgaggat caatggcttc    2340
```

-continued

```
agcttcttag gacttatgtg ggaccaatga ctgagtctct tttcccagga taccacacta    2400
aggctagggc tgttatgaac ttcgttgtga ggtatcgtcc agatgagcaa ccatctctta    2460
ggccacacca cgattcttct actttcactc ttaacgtggc tcttaaccac aagggacttg    2520
attatgaggg aggaggatgc cgtttcctta gatacgattg cgtgatttct tcaccaagaa    2580
agggatgggc tcttcttcat ccaggaaggc ttactcatta ccacgaggga cttccaacta    2640
cttggggaac tagatatatt atggtgtctt tcgtggatcc atgactgctt taatgagata    2700
tgcgagacgc ctatgatcgc atgatatttg ctttcaattc tgttgtgcac gttgtaaaaa    2760
acctgagcat gtgtagctca gatccttacc gccggtttcg gttcattcta atgaatatat    2820
cacccgttac tatcgtattt ttatgaataa tattctccgt tcaatttact gattgtccag    2880
aattcgcg                                                              2888
```

<210> SEQ ID NO 14
<211> LENGTH: 45
<212> TYPE: PRT
<213> ORGANISM: Artificial Sequence
<220> FEATURE:
<223> OTHER INFORMATION: Vacuolar targeting sequence of the thiol
      protease aleurain precursor (NCBI accession P05167 GI:113603)

<400> SEQUENCE: 14

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala
        35                  40                  45

<210> SEQ ID NO 15
<211> LENGTH: 1469
<212> TYPE: PRT
<213> ORGANISM: Homo sapiens

<400> SEQUENCE: 15

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu Gln
        35                  40                  45

Glu Glu Gly Gln Val Gly Gln Asp Glu Asp Ile Pro Pro Ile Thr
    50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                85                  90                  95

Asp Val Ile Cys Asp Glu Thr Lys Asn Cys Pro Gly Ala Glu Val Pro
            100                 105                 110

Glu Gly Glu Cys Cys Pro Val Cys Pro Asp Gly Ser Glu Ser Pro Thr
        115                 120                 125

Asp Gln Glu Thr Thr Gly Val Glu Gly Pro Lys Gly Asp Thr Gly Pro
    130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly

```
                165                 170                 175
Pro Pro Gly Leu Gly Gly Asn Phe Ala Pro Gln Leu Ser Tyr Gly Tyr
            180                 185                 190
Asp Glu Lys Ser Thr Gly Gly Ile Ser Val Pro Gly Pro Met Gly Pro
            195                 200                 205
Ser Gly Pro Arg Gly Leu Pro Gly Pro Pro Gly Ala Pro Gly Pro Gln
210                 215                 220
Gly Phe Gln Gly Pro Pro Gly Glu Pro Gly Glu Pro Gly Ala Ser Gly
225                 230                 235                 240
Pro Met Gly Pro Arg Gly Pro Pro Gly Pro Pro Gly Lys Asn Gly Asp
                245                 250                 255
Asp Gly Glu Ala Gly Lys Pro Gly Arg Pro Gly Glu Arg Gly Pro Pro
            260                 265                 270
Gly Pro Gln Gly Ala Arg Gly Leu Pro Gly Thr Ala Gly Leu Pro Gly
            275                 280                 285
Met Lys Gly His Arg Gly Phe Ser Gly Leu Asp Gly Ala Lys Gly Asp
290                 295                 300
Ala Gly Pro Ala Gly Pro Lys Gly Glu Pro Gly Ser Pro Gly Glu Asn
305                 310                 315                 320
Gly Ala Pro Gly Gln Met Gly Pro Arg Gly Leu Pro Gly Glu Arg Gly
                325                 330                 335
Arg Pro Gly Ala Pro Gly Pro Ala Gly Ala Arg Gly Asn Asp Gly Ala
            340                 345                 350
Thr Gly Ala Ala Gly Pro Pro Gly Pro Thr Gly Pro Ala Gly Pro Pro
            355                 360                 365
Gly Phe Pro Gly Ala Val Gly Ala Lys Gly Glu Ala Gly Pro Gln Gly
            370                 375                 380
Pro Arg Gly Ser Glu Gly Pro Gln Gly Val Arg Gly Glu Pro Gly Pro
385                 390                 395                 400
Pro Gly Pro Ala Gly Ala Ala Gly Pro Ala Gly Asn Pro Gly Ala Asp
                405                 410                 415
Gly Gln Pro Gly Ala Lys Gly Ala Asn Gly Ala Pro Gly Ile Ala Gly
            420                 425                 430
Ala Pro Gly Phe Pro Gly Ala Arg Gly Pro Ser Gly Pro Gln Gly Pro
            435                 440                 445
Gly Gly Pro Pro Gly Pro Lys Gly Asn Ser Gly Glu Pro Gly Ala Pro
            450                 455                 460
Gly Ser Lys Gly Asp Thr Gly Ala Lys Gly Glu Pro Gly Pro Val Gly
465                 470                 475                 480
Val Gln Gly Pro Pro Gly Pro Ala Gly Glu Glu Gly Lys Arg Gly Ala
                485                 490                 495
Arg Gly Glu Pro Gly Pro Thr Gly Leu Pro Gly Pro Pro Gly Glu Arg
            500                 505                 510
Gly Gly Pro Gly Ser Arg Gly Phe Pro Gly Ala Asp Gly Val Ala Gly
            515                 520                 525
Pro Lys Gly Pro Ala Gly Glu Arg Gly Ser Pro Gly Pro Ala Gly Pro
            530                 535                 540
Lys Gly Ser Pro Gly Glu Ala Gly Arg Pro Gly Glu Ala Gly Leu Pro
545                 550                 555                 560
Gly Ala Lys Gly Leu Thr Gly Ser Pro Gly Ser Pro Gly Pro Asp Gly
                565                 570                 575
Lys Thr Gly Pro Pro Gly Pro Ala Gly Gln Asp Gly Arg Pro Gly Pro
            580                 585                 590
```

```
Pro Gly Pro Pro Gly Ala Arg Gly Gln Ala Gly Val Met Gly Phe Pro
        595                 600                 605
Gly Pro Lys Gly Ala Ala Gly Glu Pro Gly Lys Ala Gly Glu Arg Gly
610                 615                 620
Val Pro Gly Pro Pro Gly Ala Val Gly Pro Ala Gly Lys Asp Gly Glu
625                 630                 635                 640
Ala Gly Ala Gln Gly Pro Pro Gly Pro Ala Gly Pro Ala Gly Glu Arg
                645                 650                 655
Gly Glu Gln Gly Pro Ala Gly Ser Pro Gly Phe Gln Gly Leu Pro Gly
            660                 665                 670
Pro Ala Gly Pro Pro Gly Glu Ala Gly Lys Pro Gly Glu Gln Gly Val
                675                 680                 685
Pro Gly Asp Leu Gly Ala Pro Gly Pro Ser Gly Ala Arg Gly Glu Arg
        690                 695                 700
Gly Phe Pro Gly Glu Arg Gly Val Gln Gly Pro Pro Gly Pro Ala Gly
705                 710                 715                 720
Pro Arg Gly Ala Asn Gly Ala Pro Gly Asn Asp Gly Ala Lys Gly Asp
                725                 730                 735
Ala Gly Ala Pro Gly Ala Pro Gly Ser Gln Gly Ala Pro Gly Leu Gln
                740                 745                 750
Gly Met Pro Gly Glu Arg Gly Ala Ala Gly Leu Pro Gly Pro Lys Gly
            755                 760                 765
Asp Arg Gly Asp Ala Gly Pro Lys Gly Ala Asp Gly Ser Pro Gly Lys
        770                 775                 780
Asp Gly Val Arg Gly Leu Thr Gly Pro Ile Gly Pro Pro Gly Pro Ala
785                 790                 795                 800
Gly Ala Pro Gly Asp Lys Gly Glu Ser Gly Pro Ser Gly Pro Ala Gly
                805                 810                 815
Pro Thr Gly Ala Arg Gly Ala Pro Gly Asp Arg Gly Glu Pro Gly Pro
            820                 825                 830
Pro Gly Pro Ala Gly Phe Ala Gly Pro Pro Gly Ala Asp Gly Gln Pro
        835                 840                 845
Gly Ala Lys Gly Glu Pro Gly Asp Ala Gly Ala Lys Gly Asp Ala Gly
        850                 855                 860
Pro Pro Gly Pro Ala Gly Pro Ala Gly Pro Pro Gly Pro Ile Gly Asn
865                 870                 875                 880
Val Gly Ala Pro Gly Ala Lys Gly Ala Arg Gly Ser Ala Gly Pro Pro
                885                 890                 895
Gly Ala Thr Gly Phe Pro Gly Ala Ala Gly Arg Val Gly Pro Pro Gly
                900                 905                 910
Pro Ser Gly Asn Ala Gly Pro Pro Gly Pro Pro Gly Pro Ala Gly Lys
        915                 920                 925
Glu Gly Gly Lys Gly Pro Arg Gly Glu Thr Gly Pro Ala Gly Arg Pro
        930                 935                 940
Gly Glu Val Gly Pro Pro Gly Pro Pro Gly Pro Ala Gly Glu Lys Gly
945                 950                 955                 960
Gly Gln Arg Gly Val Val Gly Leu Pro Gly Gln Arg Gly Glu Arg Gly
            965                 970                 975
Phe Pro Gly Leu Pro Gly Pro Ser Gly Glu Pro Gly Lys Gln Gly Pro
        980                 985                 990
Ser Gly Ala Ser Gly Glu Arg Gly   Pro Pro Gly Pro Met   Gly Pro Pro
        995                 1000                1005
```

```
Gly Leu Ala Gly Pro Pro Gly Glu Ser Gly Arg Glu Gly Ala Pro
    1010            1015            1020

Gly Ala Glu Gly Ser Pro Gly Arg Asp Gly Ser Pro Gly Ala Lys
    1025            1030            1035

Gly Asp Arg Gly Glu Thr Gly Pro Ala Gly Pro Pro Gly Ala Pro
    1040            1045            1050

Gly Ala Pro Gly Ala Pro Gly Pro Val Gly Pro Ala Gly Lys Ser
    1055            1060            1065

Gly Asp Arg Gly Glu Thr Gly Pro Ala Gly Pro Ala Gly Pro Val
    1070            1075            1080

Gly Pro Ala Gly Ala Arg Gly Pro Ala Gly Pro Gln Gly Pro Arg
    1085            1090            1095

Gly Asp Lys Gly Glu Thr Gly Glu Gln Gly Asp Arg Gly Ile Lys
    1100            1105            1110

Gly His Arg Gly Phe Ser Gly Leu Gln Gly Pro Pro Gly Pro Pro
    1115            1120            1125

Gly Ser Pro Gly Glu Gln Gly Pro Ser Gly Ala Ser Gly Pro Ala
    1130            1135            1140

Gly Pro Arg Gly Pro Pro Gly Ser Ala Gly Ala Pro Gly Lys Asp
    1145            1150            1155

Gly Leu Asn Gly Leu Pro Gly Pro Ile Gly Pro Pro Gly Pro Arg
    1160            1165            1170

Gly Arg Thr Gly Asp Ala Gly Pro Val Gly Pro Pro Gly Pro Pro
    1175            1180            1185

Gly Pro Pro Gly Pro Pro Gly Pro Pro Ser Ala Gly Phe Asp Phe
    1190            1195            1200

Ser Phe Leu Pro Gln Pro Pro Gln Glu Lys Ala His Asp Gly Gly
    1205            1210            1215

Arg Tyr Tyr Arg Ala Asp Asp Ala Asn Val Val Arg Asp Arg Asp
    1220            1225            1230

Leu Glu Val Asp Thr Thr Leu Lys Ser Leu Ser Gln Gln Ile Glu
    1235            1240            1245

Asn Ile Arg Ser Pro Glu Gly Ser Arg Lys Asn Pro Ala Arg Thr
    1250            1255            1260

Cys Arg Asp Leu Lys Met Cys His Ser Asp Trp Lys Ser Gly Glu
    1265            1270            1275

Tyr Trp Ile Asp Pro Asn Gln Gly Cys Asn Leu Asp Ala Ile Lys
    1280            1285            1290

Val Phe Cys Asn Met Glu Thr Gly Glu Thr Cys Val Tyr Pro Thr
    1295            1300            1305

Gln Pro Ser Val Ala Gln Lys Asn Trp Tyr Ile Ser Lys Asn Pro
    1310            1315            1320

Lys Asp Lys Arg His Val Trp Phe Gly Glu Ser Met Thr Asp Gly
    1325            1330            1335

Phe Gln Phe Glu Tyr Gly Gly Gln Gly Ser Asp Pro Ala Asp Val
    1340            1345            1350

Ala Ile Gln Leu Thr Phe Leu Arg Leu Met Ser Thr Glu Ala Ser
    1355            1360            1365

Gln Asn Ile Thr Tyr His Cys Lys Asn Ser Val Ala Tyr Met Asp
    1370            1375            1380

Gln Gln Thr Gly Asn Leu Lys Lys Ala Leu Leu Leu Lys Gly Ser
    1385            1390            1395

Asn Glu Ile Glu Ile Arg Ala Glu Gly Asn Ser Arg Phe Thr Tyr
```

```
                1400                1405                1410
Ser Val Thr Val Asp Gly Cys Thr Ser His Thr Gly Ala Trp Gly
    1415                1420                1425

Lys Thr Val Ile Glu Tyr Lys Thr Thr Lys Thr Ser Arg Leu Pro
    1430                1435                1440

Ile Ile Asp Val Ala Pro Leu Asp Val Gly Ala Pro Asp Gln Glu
    1445                1450                1455

Phe Gly Phe Asp Val Gly Pro Val Cys Phe Leu
    1460                1465

<210> SEQ ID NO 16
<211> LENGTH: 4416
<212> TYPE: DNA
<213> ORGANISM: Homo sapiens

<400> SEQUENCE: 16
atggctcacg ctcgtgttct cctcctcgct ctcgctgttt tggcaacagc tgctgtggct    60
gtggcttcta gttcttcttt tgctgattca aaccctatta gacctgttac tgatagagca   120
gcttccactt tggctcaatt gcaagaggag ggccaggttg agggccaaga tgaggatatc   180
cctccaatta catgcgtgca aaatggcttg cgttaccacg ataggatgt gtggaaacct   240
gaaccttgtc gtatctgtgt gtgtgataac ggcaaggtgc tctgcgatga tgttatctgc   300
gatgagacaa aaaattgccc tggcgctgaa gttcctgagg cgagtgttg ccctgtgtgc   360
cctgatggtt ccgagtcccc aactgatcag gaaactactg cgtggaggg cccaaaagga   420
gatactggtc cacgtggtcc taggggtcca gcaggtcctc caggtagaga tggtattcca   480
ggccagcctg gattgccagg accaccaggc ccacctggcc caccaggacc tcctggtctt   540
ggtgaaaatt cgctccaca actctcttat ggctatgatg agaagtcaac aggtggtatt   600
tccgttccag gtcctatggg accatccgga ccaagaggtc tcccaggtcc tccaggtgct   660
cctgaccctc aaggctttca aggacctcca ggcgaaccag agaaccagg cgcttctgga   720
ccaatgggcc caaggggacc acctggccca ccaggaaaaa atggcgatga tgcgaagct   780
ggaaagcctg tcgtcctggg agagagaggt cctcctggcc cacagggtgc aagaggcttg   840
ccaggaactg ctggcttgcc tggaatgaag ggacataggg gcttctccgg cctcgatggc   900
gctaagggtg atgctggccc tgctggacca aagggcgagc caggttcccc tggagaaaac   960
ggtgctcctg gacaaatggg tcctcgtgga cttccaggag aaagggtcg tccaggcgct  1020
ccaggaccag caggtgctag gggaaacgat ggtgcaacag cgctgctgg ccctcctggc  1080
ccaactggtc ctgctggccc tccaggattc ccaggcgcag ttggagctaa aggagaagca  1140
ggaccacagg gcctagggg ttctgaagga cctcagggtg ttagaggtga accaggtcct  1200
ccaggcccag ctggagcagc tggtccagca ggaaatccag gtgctgatgg tcaacctgga  1260
gctaagggcg ctaatggcgc accaggtatc gcaggcgcac caggtttcc tggcgctaga  1320
ggcccaagtg gtcctcaagg accaggtgga ccaccaggtc caaaaggcaa ttctggcgaa  1380
cctggcgctc aggttctaa aggagatact ggtgctaaag gcgaaccagg acctgttggt  1440
gttcagggtc ctcctggtcc tgctggagaa gaggaaaaa gaggtgctcg tggagaacca  1500
ggaccaactg gacttcctgg acctcctggt gaacgtggcg acctggctc aagggggtttc  1560
cctggagctg atggagtggc aggtccaaaa ggccctgctg agagagagg ttcaccaggt  1620
ccagctggtc ctaagggctc ccctggtgaa gcaggtagac aggcgaagc aggattgcca  1680
ggcgcaaagg gattgacagg ctctcctggt agtcctggcc cagatggaaa aacaggccca  1740
```

```
ccaggtccag caggacaaga tggacgtcca ggcccaccag gtcctcctgg agcaagggga   1800
caagctggcg ttatgggttt tccaggacct aaaggtgctg ctggagagcc aggaaaggca   1860
ggtgaaagag gagttcctgg tccaccagga gcagtgggtc ctgctggcaa agatggtgaa   1920
gctggagcac agggccctcc aggccctgct ggcccagctg gcgaacgtgg agaacaaggc   1980
ccagctggta gtccaggatt tcaaggattg cctggccctg ctggccctcc aggagaagca   2040
ggaaaacctg gagaacaagg agttcctggt gatttgggag cacctggacc ttcaggagca   2100
cgtggtgaaa gaggcttccc tggcgagagg ggtgttcaag gtccaccagg tccagcagga   2160
cctagaggtg ctaatggcgc tcctggcaac gatggagcaa aggtgatgc tggtgctcct   2220 ggcgcacctg gaagtcaggg tgctcctgga ttgcaaggaa tgcctggaga gagggtgct   2280 gctggcttgc caggcccaaa gggcgatagg ggtgatgctg accaaaagg tgctgatgga   2340 tccccaggaa aagatggagt tcgtggtctt actggcccaa tcggacctcc aggccctgct   2400
ggcgctccag gtgataaggg cgaaagtggc ccaagtggac ctgctggacc tactggtgct   2460
agaggtgcac ctggtgatag gggtgaacct ggaccacctg gtccagctgg ttttgctggt   2520
cctcctggag ctgatggaca acctggcgca aagggtgaac aggtgatgc tggcgcaaag   2580 ggagatgctg gtccacctgg acctgctggt ccagcaggcc cccctgggcc aatcggtaat   2640
gttggagcac aggtgctaa gggagctagg ggttccgctg gtccacctgg agcaacagga   2700
tttccaggcg ctgctggtag agttggccca ccaggcccat ccggaaacgc aggccctcct   2760
ggtcctccag gtcctgctgg caaggagggt ggcaaaggac caggggcga aactggccct   2820 gctggtagac ctggcgaagt tggccctcct ggaccaccag gtccagcagg agaaaaaggt   2880
ggacagagag gcgttgtggg actccctggt caaaggggag agagaggatt tccaggcttg   2940
ccaggaccta gtggagaacc tggaaaacaa ggcccatcag gcgctagtgg agagcgtgga   3000
cctcctggcc ctatgggacc tcctggattg gctggcccac ctggcgaatc aggtcgtgaa   3060
ggcgcaccag gcgcagaagg atcacctgga agagatggat cccctggtgc taaaggcgat   3120 cgtgagaaa ctggtccagc aggcccacca ggcgcaccag gtgcacctgg cgctccagga   3180
cctgtgggac cagctggaaa atccggagat aggggcgaga caggcccagc aggaccagct   3240
ggacctgttg gcctgctgg cgctcgtgga ccagcaggac ctcaaggacc aaggggagat   3300
aagggagaaa caggcgaaca aggcgatagg ggcattaagg gtcataggg ttttagtggc   3360 ctccagggtc ctcctggccc acctggatca ccaggagaac agggaccatc tggtgcttcc   3420
ggcccagctg gtccaagagg acctccagga tcagctggtg cacctggaaa agatggtctt   3480
aacggtctcc caggaccaat cggccctcca ggacctagag aagaacagg agatgctggc   3540 cctgttggcc ctcaggacc tcctggtcca ccagtccac ctggtcctcc atcagctgga   3600 ttcgatttt catttcttcc acagccacca caagagaaag ctcacgatgg cggcagatat   3660
taccgtgctg atgatgctaa cgttgttagg gatagagatt tggaagtgga tacaacttg   3720 aaatccctct cccagcaaat tgaaaacatt agatctccag aaggttcacg taaaaaccca   3780
gctagaacat gtcgtgattt gaaaatgtgt cactccgatt ggaaaagtgg tgaatactgg   3840
attgatccaa atcagggctg taatctcgat gctatcaaag ttttctgtaa catggaaaca   3900
ggcgaaacat gcgttttatcc tactcaacct tccgtggctc agaaaaattg gtacatctca   3960
aaaaatccta agataagag gcacgtttgg ttcggtgaaa gtatgactga tggatttcaa   4020
tttgagtacg gcggtcaagg tagtgatcca gctgatgtgg ctattcaact cacattttg   4080
```

-continued

```
cgtcttatgt ccacagaggc atcacaaaac atcacttacc actgcaaaaa cagtgtggct    4140
tatatggatc aacaaacagg aaaccttaag aaggctcttc ttttgaaggg ctcaaacgag    4200
attgagatta gagcagaggg caactcaagg tttacttatt cagttactgt tgatggctgc    4260
acttcacata ctggcgcttg gggtaaaaca gttatcgagt ataagactac aaaaacatca    4320
agactcccaa tcattgatgt tgctcctctc gatgttggcg ctcctgatca agagttcggt    4380
tttgatgtgg gcccagtttg tttcctctaa tgagct                              4416
```